(12) United States Patent
Evarts et al.

(10) Patent No.: US 8,440,677 B2
(45) Date of Patent: May 14, 2013

(54) ATROPISOMERS OF 2-PURINYL-3-TOLYL-QUINAZOLINONE DERIVATIVES AND METHODS OF USE

(75) Inventors: Jerry B. Evarts, Foster City, CA (US); Roger G. Ulrich, Foster City, CA (US)

(73) Assignee: Gilead Calistoga LLC, Foster City, CA (US)

( * ) Notice: Subject to any disclaimer, the term of this patent is extended or adjusted under 35 U.S.C. 154(b) by 331 days.

(21) Appl. No.: 12/731,089

(22) Filed: Mar. 24, 2010

(65) Prior Publication Data

US 2010/0249155 A1    Sep. 30, 2010

Related U.S. Application Data

(60) Provisional application No. 61/162,980, filed on Mar. 24, 2009, provisional application No. 61/231,550, filed on Aug. 5, 2009.

(51) Int. Cl.
*C07D 473/34* (2006.01)
*A61K 31/52* (2006.01)
*A61P 19/02* (2006.01)

(52) U.S. Cl.
USPC .................................. 514/263.21; 544/277

(58) Field of Classification Search .............. 544/277; 514/263.21
See application file for complete search history.

(56) References Cited

U.S. PATENT DOCUMENTS

| | | | |
|---|---|---|---|
| 3,322,756 A | 5/1967 | Ruschig et al. | |
| 3,691,016 A | 9/1972 | Patel | |
| 3,897,432 A | 7/1975 | Shen et al. | |
| 3,969,287 A | 7/1976 | Jaworek et al. | |
| 3,984,555 A | 10/1976 | Amschler et al. | |
| 4,179,337 A | 12/1979 | Davis et al. | |
| 4,183,931 A | 1/1980 | Wolfe et al. | |
| 4,195,128 A | 3/1980 | Hildebrand et al. | |
| 4,225,489 A | 9/1980 | Rolf et al. | |
| 4,229,537 A | 10/1980 | Hodgins et al. | |
| 4,247,642 A | 1/1981 | Hirohara et al. | |
| 4,289,872 A | 9/1981 | Denkewalter et al. | |
| 4,301,144 A | 11/1981 | Iwashita et al. | |
| 4,330,440 A | 5/1982 | Ayers et al. | |
| 4,496,689 A | 1/1985 | Mitra | |
| 4,640,835 A | 2/1987 | Shimizu et al. | |
| 4,670,417 A | 6/1987 | Iwasaki et al. | |
| 4,791,192 A | 12/1988 | Nakagawa et al. | |
| 4,925,673 A | 5/1990 | Steiner et al. | |
| 5,013,556 A | 5/1991 | Woodle et al. | |
| 5,225,347 A | 7/1993 | Goldberg et al. | |
| 5,229,490 A | 7/1993 | Tam | |
| 5,378,725 A | 1/1995 | Bonjouklian et al. | |
| 5,480,906 A | 1/1996 | Creemer et al. | |
| RE35,862 E | 7/1998 | Steiner et al. | |
| 5,858,753 A | 1/1999 | Chantry et al. | |
| 5,882,910 A | 3/1999 | Chantry et al. | |
| 5,948,664 A | 9/1999 | Williams et al. | |
| 5,985,589 A | 11/1999 | Chantry et al. | |
| 6,046,049 A | 4/2000 | Monia et al. | |
| 6,048,970 A | 4/2000 | Lal et al. | |
| 6,277,981 B1 | 8/2001 | Tu et al. | |
| 6,291,220 B1 | 9/2001 | Williams et al. | |
| 6,369,038 B1 | 4/2002 | Blumenfeld et al. | |
| 6,380,204 B1 | 4/2002 | Chenard et al. | |
| 6,410,224 B1 | 6/2002 | Stinchcomb et al. | |
| 6,482,623 B1 | 11/2002 | Vanhaesebroeck et al. | |
| 6,518,277 B1 | 2/2003 | Sadhu et al. | |
| 6,667,300 B2 | 12/2003 | Sadhu et al. | |
| 6,696,250 B1 | 2/2004 | Cech et al. | |
| 6,800,620 B2 | 10/2004 | Sadhu et al. | |
| 6,949,535 B2 | 9/2005 | Sadhu et al. | |
| 7,932,260 B2 | 4/2011 | Fowler et al. | |

(Continued)

FOREIGN PATENT DOCUMENTS

| EP | 0364598 A1 | 4/1990 |
|---|---|---|
| EP | 0 525 960 A1 | 2/1993 |

(Continued)

OTHER PUBLICATIONS

International Search Report and Written Opinion for PCT/US2010/028554, mailed Jul. 28, 2010, 8 pages.
Berge et al., J. Pharm. Sci. (1977) 66:1.
Chantry et al., J. Biol. Chem. (1997) 272:19236-19241.
Fuwa et al., Tetrahedron (2005) 61:4297-4312.
Lee et al., FASEB J. (2006) 20:455-465.
Newell et al., J. Chem. Soc., Perkin Trans (2001) 2:961-963.
Oki, "Recent Advances in Atropisomerism" Topics in Stereochemistry (1983) 14:1-81.

(Continued)

*Primary Examiner* — Mark Berch
(74) *Attorney, Agent, or Firm* — Morrison & Foerster LLP

(57) ABSTRACT

The invention provides compounds, compositions and methods to treat certain inflammatory conditions and/or oncology by administering a compound that inhibits PI3K isoforms, particularly the delta isoform. It further provides specific stereoisomers of a compound useful for these methods. In particular, the compound is an optically active atropisomer of 2-((6-amino-9H-purin-9-yl)methyl)-5-methyl-3-o-tolylquinazolin-4(3H)-one.

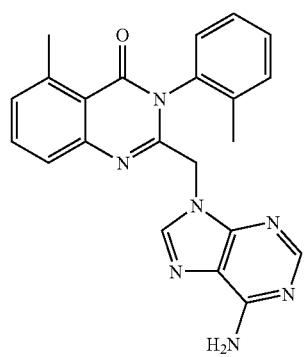

14 Claims, 15 Drawing Sheets

U.S. PATENT DOCUMENTS

| | | | |
|---|---|---|---|
| 8,138,195 | B2 | 3/2012 | Sadhu et al. |
| 2004/0023390 | A1 | 2/2004 | Davidson et al. |
| 2004/0092561 | A1 | 5/2004 | Ruckle et al. |
| 2004/0121996 | A1 | 6/2004 | Barvian et al. |
| 2004/0138199 | A1 | 7/2004 | Goglietti et al. |
| 2004/0242631 | A1 | 12/2004 | Garlich et al. |
| 2004/0248953 | A1 | 12/2004 | Gogliotti et al. |
| 2004/0248954 | A1 | 12/2004 | Gogliotti et al. |
| 2004/0259926 | A1 | 12/2004 | Bruendle et al. |
| 2005/0004195 | A1 | 1/2005 | Para et al. |
| 2005/0020630 | A1 | 1/2005 | Connolly et al. |
| 2005/0020631 | A1 | 1/2005 | Gogliotti et al. |
| 2005/0043239 | A1 | 2/2005 | Douangpanya et al. |
| 2005/0054614 | A1 | 3/2005 | Diacovo et al. |
| 2005/0239809 | A1* | 10/2005 | Watts et al. ............ 514/263.21 |
| 2005/0261317 | A1 | 11/2005 | Sadhu et al. |
| 2006/0079538 | A1 | 4/2006 | Hallahan et al. |
| 2006/0106038 | A1 | 5/2006 | Bouscary et al. |
| 2008/0275067 | A1 | 11/2008 | Fowler et al. |
| 2008/0287469 | A1 | 11/2008 | Diacovo et al. |
| 2010/0029693 | A1 | 2/2010 | Douangpanya et al. |
| 2010/0152211 | A1 | 6/2010 | Sadhu et al. |
| 2010/0168139 | A1 | 7/2010 | Sadhu et al. |
| 2010/0202963 | A1 | 8/2010 | Gallatin et al. |
| 2010/0249155 | A1 | 9/2010 | Evarts et al. |
| 2010/0256167 | A1 | 10/2010 | Fowler et al. |
| 2010/0256168 | A1 | 10/2010 | Fowler et al. |
| 2012/0015964 | A1* | 1/2012 | Fowler et al. ............ 514/263.21 |
| 2012/0172591 | A1* | 7/2012 | Sadhu et al. ................ 544/118 |

FOREIGN PATENT DOCUMENTS

| | | | |
|---|---|---|---|
| EP | 0 525 960 B1 | 2/1993 | |
| EP | 0 675 124 A2 | 10/1995 | |
| EP | 0 675 124 A3 | 10/1995 | |
| EP | 0 716 857 A1 | 6/1996 | |
| EP | 0 716 875 B1 | 6/1996 | |
| EP | 0 884 310 A1 | 12/1998 | |
| EP | 0 884 310 B1 | 12/1998 | |
| EP | 0 900 568 A2 | 3/1999 | |
| EP | 0 900 568 A3 | 3/1999 | |
| EP | 1939203 A2 | 7/2008 | |
| EP | 1939203 A3 | 7/2008 | |
| GB | 1356763 A | 6/1974 | |
| GB | 2 017 097 A | 10/1979 | |
| JP | 55 118917 A2 | 9/1980 | |
| JP | 55 118918 A2 | 1/1981 | |
| JP | 56 002322 A2 | 1/1981 | |
| WO | WO-93/21259 A1 | 10/1993 | |
| WO | WO-94/17090 A1 | 8/1994 | |
| WO | WO-95/24379 A1 | 9/1995 | |
| WO | WO-96/04923 A1 | 2/1996 | |
| WO | WO-96/25488 A1 | 8/1996 | |
| WO | WO-96/32478 A1 | 10/1996 | |
| WO | WO-97/34631 A1 | 9/1997 | |
| WO | WO-97/41097 A2 | 11/1997 | |
| WO | WO-97/43276 A1 | 11/1997 | |
| WO | WO-97/46688 A1 | 12/1997 | |
| WO | WO-98/33802 A1 | 8/1998 | |
| WO | WO-98/38173 A1 | 9/1998 | |
| WO | WO-99/08501 A2 | 2/1999 | |
| WO | WO-99/08501 A3 | 2/1999 | |
| WO | WO-99/34804 A1 | 7/1999 | |
| WO | WO-01/00881 A1 | 1/2001 | |
| WO | WO-01/30768 A1 | 5/2001 | |
| WO | WO-01/30768 C2 | 5/2001 | |
| WO | WO-01/53266 A1 | 7/2001 | |
| WO | WO-01/57034 A1 | 8/2001 | |
| WO | WO-01/81346 A2 | 11/2001 | |
| WO | WO-01/81646 A3 | 11/2001 | |
| WO | WO-2011/153514 A9 | 12/2001 | |
| WO | WO-2011/153514 C2 | 12/2001 | |
| WO | WO-03/035075 | 5/2003 | |
| WO | WO-03/035075 A1 | 5/2003 | |
| WO | WO-03/106622 A2 | 12/2003 | |
| WO | WO-03/106622 A3 | 12/2003 | |
| WO | WO-2004/007491 A1 | 1/2004 | |
| WO | WO-2004/012768 A1 | 2/2004 | |
| WO | WO-2004/026285 A2 | 4/2004 | |
| WO | WO-2004/026285 A3 | 4/2004 | |
| WO | WO-2004/029055 A1 | 4/2004 | |
| WO | WO-2004/052373 A1 | 6/2004 | |
| WO | WO-2004/056820 A1 | 7/2004 | |
| WO | WO-2004/089925 A1 | 10/2004 | |
| WO | WO-2004/108708 A1 | 12/2004 | |
| WO | WO-2004/108709 A1 | 12/2004 | |
| WO | WO-2004/108713 A1 | 12/2004 | |
| WO | WO-2004/108713 C1 | 12/2004 | |
| WO | WO-2004/108715 A1 | 12/2004 | |
| WO | WO-2004/108715 C1 | 12/2004 | |
| WO | WO-2005/016348 A1 | 2/2005 | |
| WO | WO-2005/016349 A1 | 2/2005 | |
| WO | WO-2005/067901 A1 | 7/2005 | |
| WO | WO-2005/067901 A3 | 7/2005 | |
| WO | WO-2005/113556 A1 | 12/2005 | |
| WO | WO-2005/117889 A1 | 12/2005 | |
| WO | WO-2005/120511 A1 | 12/2005 | |
| WO | WO-2006/089106 A2 | 8/2006 | |
| WO | WO-2006/089106 A3 | 8/2006 | |
| WO | WO-2007/076085 A2 | 7/2007 | |
| WO | WO-2007/076085 A3 | 7/2007 | |
| WO | WO-2008/064018 A1 | 5/2008 | |
| WO | WO-2008/064018 C1 | 5/2008 | |
| WO | WO-2009/046448 A1 | 4/2009 | |
| WO | WO-2009/058361 A1 | 5/2009 | |
| WO | WO-2009/088986 A1 | 7/2009 | |
| WO | WO-2009/088990 A1 | 7/2009 | |
| WO | WO-2010/057048 A1 | 5/2010 | |
| WO | WO-2010/065923 A2 | 6/2010 | |
| WO | WO-2010/065923 A3 | 6/2010 | |
| WO | WO-2010/123931 A1 | 10/2010 | |
| WO | WO 2011011550 A1 * | 1/2011 | |
| WO | WO-2011/153514 A2 | 12/2011 | |

OTHER PUBLICATIONS

Prescott, (ed.), Methods in Cell Biology, vol. XIV, p. 33, Academic Press, New York (1976).
Sakamoto et al., Angew. Chem. (2003) 115:4496-4499.
White et al., Bioorganic & Medicinal Chemistry (2004) 12:5711-5717.
Williams et al., Chemistry & Biology (2010) 17:123-134.
Zhang and Franco, "Method development with CHIRALPAK IA: The new Diacel column with broad solvent versatility" Chiral Technologies Europe, Apr. 2004.
"Acute Congestive Heart Failure", Thomas N. Levin, Postgraduate Medicine, vol. 101, No. 1, 1997.
"Cardiovascular Disease: Treatment for Stroke", Stanford Hospital & Clinics, 2003.
"Heart Disease", Charlotte E. Grayson, WebMD, 2004.
"NIH Heart Disease & Stroke Research: Fact Sheet", American Heart Association, 2004.
"Chemia Lekow", ed. E. Pawelczyk, PZWL, Warszawa 1986, see, part 1.2.2.
"Preparatyka Organiczna", ed. A.I. Vogel, WNT, Warszawa 1984, page e.g. 83.
Abramson and Shipp, Blood (2005) 106(4):1164-1174.
Abu-Duhier et al., Br. J. Haematol. (2001) 113:983-988.
Adamkiewicz, "Tumor Angiogenesis: Mechanisms" IMT Marburg—Research Group, retrieved from the internet on Apr. 13, 2004, URL: <http://www.imt.uni-marburg.de/_adamkiew/mechanism.html>.
Advisory Action from U.S. Appl. No. 11/596,092, mailed on Jul. 27, 2010.
Ager et al., J. Med. Chem. (1977) 20:379-386.
Ali et al., Nature (2004) 431:1007-1011.
Alon et al., "The molecular basis of leukocyte adhesion to and migration through vascular endothelium," Mirelman et al. (eds.), Life Sciences Open Day Book 2002, Weizmann Institute of Science, Life Sciences Department, Chapter 8, vol. 2:206-207 (2002), retrieved from the internet on Sep. 2, 2005, URL: <www.weizmann.ac.ll/Biology/open_day_2002/book/ronen_alon.pdf>.
Amendment from U.S. Appl. No. 09/841,341, filed Aug. 21, 2002.
Amendment from U.S. Appl. No. 10/027,591, filed Jun. 3, 2003.

Amendment in Response to Final Office Action from U.S. Appl. No. 11/596,092, filed Jul. 19, 2010.
Amendment in Response to Non-Final Office Action / Restriction Requirement from U.S. Appl. No. 11/884,566, filed Jun. 7, 2010.
Amendment in Response to Non-Final Office Action from U.S. Appl. No. 10/918,803, filed Oct. 1, 2008.
Amendment in Response to Non-Final Office Action from U.S. Appl. No. 10/918,803, filed Sep. 4, 2009.
Amendment in Response to Non-Final Office Action from U.S. Appl. No. 11/110,204, filed Dec. 31, 2008.
Amendment in Response to Non-Final Office Action from U.S. Appl. No. 11/110,204, filed Sep. 4, 2009.
Amendment in Response to Non-Final Office Action from U.S. Appl. No. 11/110,204, filed Jun. 4, 2010.
Amendment in Response to Non-Final Office Action from U.S. Appl. No. 11/596,092, filed Nov. 10, 2009.
Amendment in Response to Non-Final Office Action from U.S. Appl. No. 11/596,092, filed Mar. 24, 2010.
Amendment Under 37 C.F.R. § 1.111 from U.S. Appl. No. 11/129,006, filed Apr. 12, 2010.
Amendment Under 37 C.F.R. § 1.111/Restriction Requirement from U.S. Appl. No. 11/110,204, filed Apr. 10, 2008.
Amendment with Request for Continued Examination from U.S. Appl. No. 11/596,092, filed Sep. 1, 2010. (8.00).
Amin et al., Circ Res (2003) 93(4):321-329.
Angel, Activities of Phosphoinositide Kinase-3 (PI3K) (1999) retrieved from the internet on May 22, 2003, URL: http://www.chem.csustan.edu/chem4400/SJBR/angel99.htm.
Angio World, "How Angiogenesis Complicates Psoriasis" (2001) retrieved from the internet on Apr. 13, 2004, URL: <http://www.angioworld.com/psoriasis.htm>.
Annabi et al., J. Cell. Biochem. (2004) 91:1146-1158.
Aoki et al., PNAS USA (2001) 98:136-141.
Aoudjit et al., J. Immunol. (1998) 161:2333-2338.
Arcaro et al., Biochem. J. (1994) 298:517-520.
Asti et al., Pulm. Pharmacol. Ther. (2000) 13:61-69.
Ausprunk et al., Microvasc. Res. (1977) 14:53-65.
Bader, A.G. et al. (2005). "Oncogenic PI3K Deregulates Transcription and Translation," Nature Reviews Cancer 5(12):921-922 (abstract and introduction).
Barakat et al., Chemical Abstracts (1996) 124(21):1334.
Barakat, S.E-S. et al. (Dec. 1994). "Synthesis and CNS Depressant Activity of Some New Quinazoline Derivatives," Az. J. Pharm. Sci. 14:239-246.
Bardet et al., 9th Congress of the European Hematology Association Geneva Palexpo, Switzerland, Jun. 10-13, 2004, View Abstract data, Abstract nr.: 620.
Barker, Lancet (1991) 338:227-230.
Benekli et al., Blood (2002) 99:252-257.
Benekli et al., Blood (2003) 101:2940-2954.
Bennett et al., Ann. Intern. Med. (1985) 103:620-625.
Bennett et al., J. Pharmacol. Exp. Ther. (1997) 280:988-1000.
Bergers et al., Science (1999) 284:808-812.
Bharadwaj et al., J. Immunol. (2001) 166:6735-6741.
Binetruy-Tournaire et al., EMBO J. (2000) 19:1525-1533.
Bloemen et al., Am. J. Respir. Crit. Care Med. (1996) 153:521-529.
Boehm et al., Nature (1997) 390:404-407.
Borregaard et al., Blood (1997) 89:3503-3521.
Boudewijn et al., Nature (1995) 376:599-602.
Bouscary et al., Blood (2003) 101:3436-3443.
Bouscary et al., Oncogene (2001) 20:2197-2204.
Bowes et al., Exp. Neurol. (1993) 119:215-219.
Brennan et al., Arthritis Res. (2002) 4(Suppl. 3):S177-S182.
Brown et al., 44th Annual Meeting of the American Society of Hematology, Philadelphia, PA, Dec. 6-10, 2002, Abstract No. 3012, p. 761A.
Brown, J. et al. (2010). "Clinical Activity in a Phase 1 Study of Cal-101, an Isoform-Selective Inhibitor of Phosphatidylinositol 3-Kinase P110Delta, in Patients with B-Cell Malignancies," Haematologica 95(s2):466, Abstract No. 1130.
Brunn et al., EMBO J. (1996) 15:5256-5267.

Burger, J.A. et al. (Dec. 12, 2008). "High-Level Expression of the T-Cell Chemokines CCL3 and CCL4 by Chronic Lymphocytic Leukemia B Cells in Nurselike Cell Cocultures and after BCR Stimulation," Blood 113(13):3050-3058.
Burkle, A. et al. (Nov. 1, 2007). "Overexpression of the CXCR5 Chemokine Receptor, and its Ligand, CXCL13 in B-Cell Chronic Lymphocytic Leukemia," Blood 110(9): 3316-3325.
Butcher et al., Science (1996) 272:60-66.
Cadwallader et al., J. Immunol. (2002) 169:3336-3344.
Cantley et al., PNAS USA (1999) 96:4240-4245.
Cantley et al., Science (2002) 296:1655-1657.
Cardone et al., Science (1998) 282:1318-1321.
Carnero et al., FEB Letters (1998) 422:155-159.
CAS Abstract, Accession No. DN 86:83505 [1977] pp. 112-118.
Castillo, J.J. et al. (Jan. 2012). "CAL-101: A Phosphatidylinositol-3-Kinase p110-Delta Inhibitor for the Treatment of Lymphoid Malignancies," Expert Opinion on Investigational Drugs 21(1): 15-22.
Cebon et al., Cancer Immun. (2003) 3:7-25.
Chang et al., Exp. Opin. Ther. Patents (2001) 11:45-59.
Chang, BioMed. Eng. Online (2003) 2:12.
Chen et al., Blood (2000) 96:3181-3187.
Chern et al., Chem. Pharm. Bull. (1998) 46(6):928-933.
Chopp et al., Stroke (1994) 25:869-876.
Choy et al., Arthritis & Rheumatism (2002) 46:3143-3150.
Clark et al., J. Neurosurg. (1991) 75:623-627.
Clavel et al., Joint Bone Spine (2003) 70:321-326.
Clayton et al., J. Exp. Med. (2002) 196:753-763.
Cleary, J.M. et al. (2010). "Development of Phosphoinositide-3 Kinase Pathway Inhibitors for Advanced Cancer," Curr. Oncol. Rep. 12:87-94.
Cosimi et al., J. Immunol. (1990) 144:4604-4612.
Coxon, Immunity (1996) 5:653-666.
Creamer et al., Angiogenesis (2002) 5:231-236.
Cross et al., Inflamm. Res. (1999) 48:255-261.
Curnock et al., Immunology (2002) 105:125-136.
Dahia et al., Hum. Mol. Genet. (1999) 8:185-193.
Dallegri et al., Inflamm. Res. (1997) 46:382-391.
Das et al., Prog. Retin. Eye Res. (2003) 22:721-748.
Datta et al., Cell (1997) 91:231-241.
Datta et al., Genes & Dev. (1999) 13:2905-2927.
Davies et al., Biochem. J. (2000) 351:95-105.
De Benedetti et al., Clin. Exper. Reheum. (1992) 10:493-498.
Deininger et al., Blood (2000) 96:3343-3356.
Demeester et al., Transplantation (1996) 62:1477-1485.
Descamps et al., J. Immunol. (2004) 173:4953-4959.
Devos, S. et al. (Nov. 2011). "A Phase 1 Study of the Selective Phosphatidylinositol 3-Kinase-Delta (PI3K) Inhibitor, CAL-101 (GS-1101), in Combination with Rituximab and/or Bendamustine in Patients with Previously Treated, Indolent Non-Hodgkin Lymphoma (iNHL)," Blood 118(21):1160.
Doggett et al., Biophys. J. (2002) 83:194-205.
Dorland's Illustrated Medical Dictionary (2003), retrieved Oct. 21, 2005 from Xreferplus, http://www.xreferplus.com/entry/4196914.
Downward, Nature (1995) 376:553-554.
Drakesmith et al., Immunol. Today (2000) 21:214-217.
Druker et al., New England Journal of Medicine (2001) 344:1038-1042.
Dunne et al., Blood (2002) 99:336-341.
Edwards et al., Canc. Res. (2002) 62:4671-4677.
Eichholtz et al., J. Biol. Chem. (1993) 268:1982-1986.
El-Fattah et al., Indian J Hetercyclic Chemistry (1995) 4:199-202.
El-Feky et al., Chemical Abstracts (1987) 106(13):650.
El-Feky et al., Chemical Abstracts (1999) 131(23):497.
El-Feky, S.A. (Aug. 1998). "Novel Quinazolinones From 2-Cyanomethyl-3-Phenyl-4(3H) Quinazolinone," Bollettino Chimico Farmaceutico 137(7):286-289.
Engelman et al., Nature Reviews (2006) 7:606-619.
Environmental Protection Agency, EPA-Radiation Information (EPA's Radiation Protection Program:Information) "Ionizing Radiation Fact Sheet Series No. 1" (May 1998) Retrieved on Apr. 21, 2004: http://www.epa.gov/radiation/docs/ionize/ionize.htm.
Erbagci et al., Clin. Biochem. (2001) 34:645-650.
Estey, Cancer (2001) 92:1059-1073.

Etzioni, Pediatr. Res. (1996) 39:191-198.
European Search Report mailed Mar. 29, 2011, for EP Patent Application No. 10163434.3, filed on Apr. 24, 2001, 9 pages.
Faffe et al., Eur. Respir. J. (2000) 15:85-91.
Fantl et al., Ann. Rev. Biochem. (1993) 62:453-481.
Faust et al., Blood (2000) 96:719-726.
Final Office Action from U.S. Appl. No. 10/918,803, mailed on Jan. 8, 2009.
Final Office Action from U.S. Appl. No. 11/129,006, mailed on Oct. 5, 2010.
Final Office Action from U.S. Appl. No. 11/596,092, mailed on May 18, 2010.
Final Office Action mailed on Oct. 24, 2011, for U.S. Appl. No. 12/732,128, filed Mar. 25, 2010, 8 pages.
Final Office Action mailed on Feb. 15, 2012, for U.S. Appl. No. 12/732,124, filed Mar. 25, 2010, 12 pages.
Final Office Action mailed on Jun. 7, 2012, for U.S. Appl. No. 11/129,006, filed May 12, 2005, 14 pages.
First Preliminary Amendment from U.S. Appl. No. 12/538,748, filed Apr. 1, 2010.
Flinn, I.W. et al. (2009). "Preliminary Evidence of Clinical Activity in a Phase 1 Study of CAL-101, a Selective Inhibitor of the p110δ Isoform of Phosphatidylinositol 3-Kinase (PI3K), in Patients with Select Hematologic Malignancies," Journal of Clinical Oncology 27:156s, Abstract 3543.
Flinn, I.W. et al. (Nov. 20, 2009). "Evidence of Clinical Activity in a Phase 1 Study of CAL-101, an Oral P110Δ Isoform-Selective Inhibitor of Phosphatidylinositol 3-Kinase, in Patients with Relapsed or Refractory B-Cell Malignancies," *Blood* 114(22):380, Abstract 922.
Flinn, W. et al. (Jun. 4-7, 2009). "Preliminary Evidence of Clinical Activity in a Phase 1 Study of CAL-101, A Potent Selective Inhibitor of the P110Delta Isoform of Phosphatidylinositol 3-Kinase, in Patients with B-Cell Maglignancies," Haematologica 94(s2):303, Abstract 0744.
Flinn, I.W. et al. (Nov. 2010). "A Phase 1 Study of CAL-101, An Isoform-Selective Inhibitor of Phosphatidylinositol 3-Kinase P110 Delta, in Combination with Rituximab and/or Bendamustine in Patients with Relapsed or Refractory B-Cell Malignancies," Blood 116(21):1168.
Folkman, Curr. Mol. Med. (2003) 3:643-651.
Folkman, Nat. Med. (1995) 1:27-31.
Frey et al., Lancet (2008) 372(9643):1088-1099 (abstract).
Freyssinier et al., Br. J. Haematol. (1999) 106:912-922.
Fruman et al., Semin. Immunol. (2002) 14:7-18.
Furman, R.R. (Jul. 2010). "New Agents in Early Clinical Trials for CLL Therapy," *Clinical Advances in Hematology & Oncology* 8(7):475-476.
Garcia-Barros et al., Science (2003) 300:1155-1159.
Genbank Accession No. AK040867, last updated Sep. 19, 2008, located at <http://www.ncbi.nlm.nih.gov.nuccore/26334014>, last visited on Apr. 16, 2010, 6 pages.
GenBank Accession No. AR255866, last updated Dec. 20, 2002, located at <http://www.ncbi.nlm.nih.gov.nuccore/27305059>, last visited on Apr. 16, 2010, 2 pages.
GenBank Accession No. BC035203, last updated Aug. 11, 2006, located at <http://www.ncbi.nlm.nih.gov.nuccore/23270986>, last visited on Apr. 16, 2010, 5 pages.
GenBank Accession No. NM_005026, last updated Apr. 11, 2010, located at <http://www.ncbi.nlm.nih.gov.nuccore/15654404>, last visited Apr. 16, 2010, 7 pages.
GenBank Accession No. NM_008840, last updated on Mar. 5, 2010, located at <http://www.ncbi.nlm.nih.gov.nuccore/255708435>, last visited on Apr. 16, 2010, 5 pages.
GenBank Accession No. U57843, last updated on May 9, 1997, located at <http://www.ncbi.nlm.nih.gov.nuccore/U57843>, last visited on Aug. 9, 2011, 2 pages.
GenBank Accession No. U86453, last updated on Jul. 7, 1998, located at <http://www.ncbi.nlm.nih.gov.nuccore/2317893>, last visited on Apr. 16, 2010, 3 pages.
GenBank Accession No. U86587, last updated Jul. 7, 1998, located at <http://www.ncbi.nlm.nih.gov/nuccore/2331237>, last visited on Apr. 16, 2010, 3 pages.

GenBank Accession No. XM_345606, last updated Jun. 22, 2006, located at <http://www.ncbi.nlm.nih.gov/nuccore/109475856?report=genbank>, last visited on Apr. 16, 2010, 3 pages.
GenBank Accession No. Y10055, last updated Oct. 7, 2008, located at <http://www.ncbi.nlm.nih.gov/nuccore/37496958>, last visited on Apr. 16, 2010, 3 pages.
Geng et al., Cancer Research (2001) 61:2413-19.
Geng et al., Cancer Research (2004) 64:4893-4899.
Geng et al., Cancer Research (2004) 64:8130-8133.
Gibson, (ed.), Antisense and Ribozyme Methodology, "Laboratory Companion" (1997) Table of Contents.
Gilliland et al., Blood (2002) 100:1532-1542.
Gilliland et al., Cancer Cell (2002) 1:417-420.
Gingras et al., Genes Dev. (2001) 15:2852-2864.
Gingras et al., Genes Dev. (2001) 15:807-826.
Glenjen et al., Int. J. Cancer (2002) 101:86-94.
Gorczynski et al., J. Immunol. (1994) 152:2011-2019.
Gorski et al., Cancer Research (1999) 59:3374-3378.
Gouilleux-Gruart et al., Blood (1996) 87:1692-1697.
Grant et al., Drugs of Today (2002) 38:783-791.
Gross et al., Science (1998) 281:703-706.
Gu et al., Mol. Cell. Biol. (2000) 20:7109-7120.
Gupta et al., Int'l J Radiation Oncology Biology Physics (2003) 56(3):846-853.
Gute et al., Mol. Cell. Biochem. (1998) 179:169-187.
Guzman et al., Blood (2001) 98:2301-2307.
Guzman et al., Proc. Natl. Acad. Sci. (USA) (2002) 99:16220-16225.
Hadden, Int. Immunopharmacol. (2003) 3:1061-1071.
Hallahan et al., Proc. Natl. Acad. Sci (USA) (1997) 94:6432-6437.
Halloran et al., Arthritis Rheum. (1996) 39:810-819.
Hanamoto et al., Am. J. Pathol. (2004) 164(3):997-1006.
Hannigan et al., Proc. Natl. Acad. Sci. U.S.A. (2002) 99:3603-3608.
Hardma et al. (eds.), Goodman and Gilman's The Pharmacological Basis of Therapeutics (1996) 9th ed., pp. 11-16.
Harlan, Haematology 96, the Education Program Book of the 26th Congress of the International Society of Haematology. Singapore, 1996.
Harning et al., Transplantation (1991) 52:842-845.
Hartley et al., Cell (1995) 82:849-856.
Hartman et al., Cardiovasc. Res. (1995) 30:47-54.
Hasagawa et al., Int. Immunol. (1994) 6:831-838.
Hassan et al., Chinese Journal of Chemistry (1991) 9:262-269.
Hattori, H. et al. (May/Jun. 2010). "Reactive Oxygen Species as Signaling Molecules in Neutrophil Chemotaxis," *Communicative and Integrative Biology* 3(3):278-281.
He et al., Opthalmol. Vis. Sci. (1994) 35:3218-3225.
Healy et al., Hum. Reprod. Update (1998) 4:736-740.
Healy et al., Pharma. Res. (Dec. 2004) 21:2234-2246.
Heit et al., J. Cell Biol. (2002) 159:91-102.
Hellman, Cancer: Principles and Practice of Oncology (1993) 4th ed., vol. 1:248-275.
Herman, S.E.M. et al. (Sep. 23, 2010). "Phosphatidylinositol 3-Kinase-δ Inhibitor CAL-101 Shows Promising Preclinical Activity in Chronic Lymphocytic Leukemia by Antagonizing Intrinsic and Extrinsic Cellular Survival Signals," *Blood* 116(12):2078-2088.
Herman, S.E.M. et al. (Mar. 4, 2011). "The Role of Phosphatidylinositol 3-Kinase-Delta in the Immunomodulatory Effects of Lenalidomide in Chronic Lymphocytic Leukemia," Blood 117(16):4323-4327.
Herold et al., Cell Immunol. (1994) 157:489-500.
Higuchi, Prodrugs as Novel Delivery Systems, vol. 14, ASCD Symposium Series, and in Roche (ed.), Bioreversible Carriers in Drug Design, American Pharmaceutical Association and Pergamon Press (1987) Chapter 1, pp. 1-12.
Hilbert et al., J. Exper. Med. (1995) 182:243-248.
Hiles et al., Cell (1992) 70:419-429.
Hilmas et al., Rad. Res. (1975) 61:128-143.
Hirsch et al., Science (2000) 287:1049-1053.
Hoellenriegel, J. et al. (Nov. 2010). "Phosphoinositide 3'-Kinase (PI3K) Delta Inhibition with CAL-101 Blocks B-Cell Receptor (BCR) Signaling and the Prosurvival Actions of Nurselike Cells (NLC), in Chronic Lymphocytic Leukemia," Blood 116(21):27-28.

Hoellenriegel, J. et al. (Jul. 29, 2011). "The Phosphoinositide 3'-Kinase Delta Inhibitor, CAL-101, Inhibits B-Cell Receptor Signaling and Chemokine Networks in Chronic Lymphocytic Leukemia," Blood 118(13): 3603-3612.
Horgan et al., Am. J. Physiol. (1991) 261:H1578-H1584.
Hu et al., Mol. Cell. Biol. (1993) 13:7677-7688.
Hu et al., Science (1995) 268:100-102.
Hussong et al., Blood (2000) 95:309-313.
Ikeda, H. et al. (Feb. 2009). "CAL-101: A Selective Inhibitor of P13K p110δ for the Treatment of Multiple Myeloma," Clinical Lymphoma and Myeloma 9(Supp. 1):S98-S99.
Ikeda, H. et al. (Nov. 16, 2008). "CAL-101, a Specific Inhibitor of the p110δ Isoform of Phosphatidylinositide 3-Kinase Induces Cytotoxicity in Multiple Myeloma (MM)," Blood 112(11):950, Abstract No. 2753.
Ikeda, H. et al. (Sep. 2, 2010). "PI3K/p110δ is a Novel Therapeutic Target in Multiple Myeloma," Blood 116(9):1460-1468.
International Preliminary Report on Patentability for PCT/US2006/005621, issued on Aug. 21, 2007, 8 pages.
International Preliminary Report on Patentability mailed on Jan. 24, 2012, for PCT Application No. PCT/US2010/042801, filed on Jul. 21, 2010, 14 pages.
International Preliminary Report on Patentability for PCT/US2010/028554, mailed on Oct. 6, 2011, 6 pages.
International Search Report for International (PCT) Patent Application Serial No. PCT/US2004/026436, dated Dec. 2, 2004.
International Search Report for International (PCT) Patent Application Serial No. PCT/US2004/029561, dated May 25, 2005.
International Search Report for International (PCT) Patent Application Serial PCT/US2004/026834, dated Nov. 29, 2004.
International Search Report for International (PCT) Patent Application Serial No. PCT/US2004/037860, dated May 6, 2005.
International Search Report mailed on Aug. 29, 2005, for PCT Application No. PCT/US2005/016778, filed on May 12, 2005, 4 pages.
International Search Report mailed on Sep. 15, 2006 for PCT Application No. PCT/US2006/005621, filed on Feb. 16, 2006, 4 pages.
International Search Report for PCT/US2009/064471, mailed on Feb. 12, 2010, 4 pages.
International Search Report mailed on Oct. 22, 2010 for PCT Application No. PCT/US2010/042801, filed on Jul. 21, 2010, 8 pages.
International Search Report mailed on Aug. 29, 2011, for PCT Application No. PCT/US2011/040051, filed Jun. 10, 2011, 6 pages.
International Search Report mailed on Dec. 5, 2011, for PCT Application No. PCT/US2011/053102, filed on Sep. 23, 2011, 4 pages.
International Search Report mailed on Jun. 14, 2012 for PCT Application No. PCT/US2012/028654, filed on Mar. 9, 2012, 7 pages.
Interview Summary from U.S. Appl. No. 10/918,825, mailed on Jun. 14, 2006.
Ismail et al., Chemical Abstracts (1983) vol. 98, No. 1, p. 406.
Isobe et al., Science (1992) 255:1125-1127.
Johnson et al., Intl. J. Rad. One. Biol. Phys. (1976) 1:659-670.
Johnson et al., J. Endourol. (2003) 17:557-562.
Jou et al., Mol. Cell. Biol. (2002) 22:8580-8591.
Kahl, B.S. (May 2010). "Novel Agents for Non-Hodgkin Lymphoma," Clinical Advances in Hematology & Oncology 8(5)(Suppl. 10):10-12.
Kakimoto et al., Cell. Immunol. (1992) 142:326-337.
Kallman et al., Canc. Res. (1972) 32:483-490.
Kandel et al., Exp. Cell Res. (1999) 253:210-229.
Kawasaki et al., J. Immunol. (1993) 150:1074-1083.
Kim et al., Endocrin. (2000) 141:1846-1853.
Kim, Retrieved from the Internet on Apr. 13, 2004: URL: http://www.math.umn.edu/~yjkim/biopaper/timy,html.
Kishimoto et al., Cell (1987) 50:193-202.
Klein et al., Cell. Signal. (2001) 13:335-343.
Klippel et al., Mol. Cell. Biol. (1994) 14:2675-2685.
Knall et al., Proc. Natl. Acad. Sci. (USA) (1997) 94:3052-3057.
Knight and Shokat, Chemistry and Biology (2005) 12:621-637.
Knight et al., Bioorganic & Medicinal Chemistry (Jul. 2004) 12:4749-4759.
Knoerzer et al., Toxicol. Pathol. (1997) 25:13-19.
Kolonin et al., Nature Medicine (2004) 10:625-632.
Kong et al., J. Biol. Chem. (2000) 275:36035-36042.
Kopf et al., Nature (1994) 368:339-342.
Krugmann et al., J. Biol. Chem. (1999) 274:17152-17158.
Kumar et al., Blood (2003) 101(10):3960-3968.
Kunkel et al., Circ. Res. (1996) 79:1196-1204.
Lannutti, B.J. et al. (Apr. 2009). "CAL-101, a Specific PI3K p110δ Inhibitor for the Treatment of Hematological Maglignancies," Proceedings of the American Association for Cancer Research 50:1400, Abstract No. #SY32-2.
Lannutti, B.J. et al. (Nov. 16, 2008). "CAL-101, a Potent Selective Inhibitor of the p110d Isoform of Phosphatidylinositol 3-Kinase, Attenuates PI3K Signaling and Inhibitos Proliferation and Survival of Acure Lumpoblastic Leukemia in Addition to a Range of Other Hematological Malignancies," Blood 112(11):12, Abstract No. 16.
Lannutti, B.J. et al. (Nov. 20, 2009). "CAL-101, An Oral P110δ Selective Phosphatidylinositol-3-Kinase (PI3K) Inhibitor for the Treatment of B Cell Malignancies Inhibits PI3K Signaling, Cellular Viability and Protective Signals of the Microenvironment," Blood 114(22):120-121, Abstract No. 286.
Lannutti, J. et al. (2010). "Demonstration of Pharmacodynamic Target Inhibition and Chemokine Modulation in Patients with CLL Following Treatment with CAL-101, a Selective Inhibitor of the P110 Delta Isoform of PI3K," Haematologica 95(S2):45-46, Abstract No. 0113.
Lannutti, J. et al. (Jun. 4-7, 2009). "CAL-101, A Specific Inhibitor of the P11-Delta Isoform of Phosphatidylinositide 3-Kinase, for the Treatment of Non-Hodgkins Lymphomas," Haematologica 94(S2):272-273, Abstract No. 0668.
Lecoq-Lafon et al., Blood (1999) 93:2578-2585.
Lemmon et al., Trends Cell. Biol. (1997) 7:237-242.
Letter from Polish Patent Law Firm "Patpol" translating Office Action from Polish Patent Application No. P-358590, dated Feb. 27, 2008.
Li et al., Trends Biochem. Sci. (Jan. 2004) 29:32-38.
Liang et al., Molecular Cancer Therapeutics (2003) 2(4):353-360.
Liekens et al., Biochem. Pharmacol. (2001) 61:253-270.
Liu et al., J. Immunol. (Jan. 2004) 172 :7-13.
Lowell et al., J. Cell Biol. (1996) 133:895-910.
Luo et al., Cancer Cell (2003) 4:257-262.
Luo et al., Leukemia (2003) 17:1-8.
Luster, N. Engl. J. Med. (1998) 338:436-445.
Madge et al., J. Biol. Chem. (2000) 275:15458-15465.
Manning et al., Mol. Cell (2002) 10:151-162.
Marley et al., Br. J. Haematol. (May 2004) 125:500-511.
May, S.E. et al. (Nov. 16, 2008). "CAL-101, a Selective Inhibitor of the p110δ Isoform of Phosphatidylinositol 3-Kinase, Effectively Induces Apoptosis in Primary Chronic Lymphocytic Leukemia Cells Providing a Novel Therapeutic Strategy for the Treatment of this Disease," Blood 112(11):1085-1086, Abstract No. 3165.
Meneses et al., Gene Ther. (2001) 8:646-648.
Milella et al., J. Clin. Invest. (2001) 108:851-859.
Miller et al., Nucleic Acids Res. (1988) 16:1215.
Moehler et al., Ann. Hematol. (2001) 80:695-705.
Moore, J. Clin. Invest. (2002) 109:313-315.
Moulton et al., Circ. (1999) 99:1726-1732.
Mulligan et al., J. Immunol. (1995) 154:1350-1363.
Mulligan et al., Proc. Natl. Acad. Sci. (USA) (1993) 90:11523-11527.
Nagase et al., Am. J. Respir. Crit. Care Med. (1996) 154:504-510.
Nakao et al., Leukemia (1996) 10:1911-1918.
Nakao et al., Muscle Nerve (1995) 18:93-102.
Neshat et al., Proc. Natl. Acad. Sci. (USA) (2001) 98:10314-10319.
Ninomiya et al., J. Biol. Chem. (1994) 269:22732-22737.
Non Final Office Action from U.S. Appl. No. 11/596,092, mailed on Dec. 24, 2009.
Non-Final Office Action from U.S. Appl. No. 09/841,341, mailed on Apr. 25, 2002.
Non-Final Office Action from U.S. Appl. No. 10/027,591, mailed on Feb. 26, 2003.
Non-Final Office Action from U.S. Appl. No. 10/918,803, mailed on Apr. 1, 2008.
Non-Final Office Action from U.S. Appl. No. 10/918,803, mailed on Mar. 16, 2010.

Non-Final Office Action from U.S. Appl. No. 10/918,825, mailed on Nov. 7, 2005.
Non-Final Office Action from U.S. Appl. No. 11/110,204, mailed on Aug. 5, 2008.
Non-Final Office Action from U.S. Appl. No. 11/110,204, mailed on Feb. 4, 2010.
Non-Final Office Action from U.S. Appl. No. 11/110,204, mailed on Jun. 17, 2009.
Non-Final Office Action from U.S. Appl. No. 11/129,006, mailed on Dec. 15, 2009.
Non-Final Office Action mailed on Jan. 20, 2012 for U.S. Appl. No. 13/163,597, filed Jun. 17, 2011, 14 pages.
Non-Final Office Action mailed on Oct. 17, 2011 for U.S. Appl. No. 12/732,124, filed Mar. 25, 2010, 8 pages.
Non-Final Office Action from U.S. Appl. No. 11/596,092, mailed on Jun. 10, 2009.
Non-Final Office Action from U.S. Appl. No. 11/884,566, mailed on Aug. 3, 2010.
Non-Final Office Action mailed on Jun. 28, 2011, for U.S. Appl. No. 12/732,124, filed Mar. 25, 2010, 11 pages.
Notice of Allowance from U.S. Appl. No. 09/841,341, mailed on Oct. 7, 2002.
Notice of Allowance from U.S. Appl. No. 10/027,591, mailed on Jul. 29, 2003.
Notice of Allowance from U.S. Appl. No. 10/337,192, mailed on Mar. 11, 2004.
Notice of Allowance from U.S. Appl. No. 10/697,912, mailed on Dec. 30, 2004.
Notice of Allowance mailed on Nov. 8, 2010, for U.S. Appl. No. 11/110,204, filed Apr. 20, 2005, 6 pages.
Notice of Reexamination for Chinese Patent Application No. 0811654.X, mailed Nov. 5, 2009; 7 pages.
Notice Regarding Non-Compliant Amendment from U.S. Appl. No. 10/918,803, mailed on Nov. 19, 2009.
Notification of Reasons for Rejection for Japanese Patent Application No. 2003-537642, mailed on May 26, 2009, 4 pages.
Office Action for European Patent Application No. 04 816 855.3, mailed on Oct. 21, 2008, 4 pages.
Ohno-Matsui et al., Invest. Ophthalmol. Vis: Sci. (2003) 44:5370-5375.
Okkenhaug et al., Science (2002) 297:1031-1034.
Oppenheimer-Marks et al., J. Clin. Invest. (1998) 101:1261-1272.
Oshiro et al., Stroke (1997) 28:2031-2038.
Otsu et al., Cell (1991) 65:91-104.
Paez et al., Frank (ed.), Cancer Treatment and Research (2003) 115:146 Kluwer Academic Publishers.
Pages et al., Nature (1994) 369:327-329.
Palanki, Curr. Med. Chem. (2002) 9:219-227.
Paleolog et al., Angiogenesis (1998/1999) 2:295-307.
Panayotou et al., Trends in Cell Biol. (1992) 2:358-360.
Panes et al., Gastroenterology (1995) 108:1761-1769.
Parasharya and Parikh, J. Inst. Chemists (1992) 64(5):184-185.
Park, S. et al. (2010). "Role of the PI3K/AKT and mTOR Signaling Pathways in Acute Myeloid Leukemia," *Haematologica* 95(5):819-829.
Parker, Current Biology (1995) 5:577-579.
Passegue et al., Proc. Natl. Acad. Sci., (USA) (2003) 100 Supp. 1:11842-11849.
Patani, G.A. et al. (1996), "Bioisosterism: A Rational Approach in Drug Design," *Chem Rev.* 96(8):3147-3176.
Pierce et al., J. Biol. Chem. (1997) 272:21096-21103.
Plows et al., J. Immunol. (1999) 162(2):1018-1023.
Podsypanina et al., Proc. Natl. Acad. Sci. (USA) (2001) 98:10320-10325.
Psychoyos et al., J. Immunol. Methods (1991) 137:37-46.
Puri et al., Blood (2005) 106(1):150-157, 144.
Puri et al., Blood (May 2004) 103:3448-3456.
Puri, K. et al. (Jul. 18-23, 2004). "A Role for Phosphoinositide 3-Kinase δ in Neutrophil Trafficking," Immunology 2004: Cytokine Network, Regulatory Cells, Signaling, and Apoptosis: Collection of Free Papers *Presented at the 12$^{th}$ International Congress of Immunology and 4$^{th}$ Annual Conference of FOCIS Medimond International Proceedings in Montreal, Canada* on Jul. 18, 23, 2004, pp. 303-307.
Quirici et al., Br. J. Haematol. (2001) 115:186-194.
Rameh et al., Cell (1995) 83:821-830.
Rameh et al., J. Biol. Chem. (1999) 274:8347-8350.
Rathman et al., J. Org. Chem. (1980) 45:2169-2176.
Remington's Pharmaceutical Sciences (1990) 18th Ed., Chapter 89, pp. 1435-1712 Table of Contents Only.
Ren et al., Curr. Drug Targets Inflamm. Allergy (2003) 2(3):242-256.
Request for Continued Examination and Amendment Under 37 C.F. R. § 1.116 from U.S. Appl. No. 10/918,803, filed May 7, 2009.
Response to Election of Species Requirement from U.S. Appl. No. 10/918,803, filed Jun. 27, 2007 (5.00).
Response to Non-Final Office Action from U.S. Appl. No. 10/918,803, filed Dec. 18, 2009.
Response to Non-Final Office Action filed on Sep. 16, 2010, for U.S. Appl. No. 10/918,803, filed Aug. 13, 2004, 25 pages.
Response to Restriction Requirement from U.S. Appl. No. 10/918,803, filed Jan. 4, 2008.
Response to Restriction Requirement from U.S. Appl. No. 11/129,006, filed May 12, 2009.
Response to Restriction Requirement from U.S. Appl. No. 11/137,901, filed Feb. 6, 2008.
Response to Restriction Requirement from U.S. Appl. No. 11/596,092, filed May 27, 2009.
Restriction Requirement from U.S. Appl. No. 10/918,803, mailed on Jun. 12, 2009.
Restriction Requirement from U.S. Appl. No. 10/918,803, mailed on Mar. 13, 2007.
Restriction Requirement from U.S. Appl. No. 10/918,803, mailed on Sep. 7, 2007.
Restriction Requirement from U.S. Appl. No. 11/110,204, mailed on Mar. 10, 2008.
Restriction Requirement from U.S. Appl. No. 11/129,006, mailed on Nov. 12, 2008.
Restriction Requirement from U.S. Appl. No. 11/137,901, mailed on Aug. 6, 2007.
Restriction Requirement from U.S. Appl. No. 11/137,901, mailed on May 23, 2008.
Restriction Requirement from U.S. Appl. No. 11/596,092, mailed on Jan. 28, 2009.
Restriction Requirement from U.S. Appl. No. 11/884,566, mailed on Apr. 5, 2010.
Restriction Requirement mailed on Oct. 14, 2010, for U.S. Appl. No. 12/732,124, filed Mar. 25, 2010, 9 pages.
Restriction Requirement mailed on Dec. 1, 2011, for U.S. Appl. No. 13/163,597, filed Jun. 17, 2011, 7 pages.
Restriction Requirement mailed on Feb. 9, 2012, for U.S. Appl. No. 12/618,612, filed Nov. 13, 2009, 7 pages.
Restriction Requirement mailed on Jun. 7, 2012, for U.S. Appl. No. 13/399,828, filed Feb. 17, 2012, 5 pages.
Reyes et al., J. Clin. Invest. (2002) 109:337-346.
Rickert et al., Trends Cell Biol. (2000) 10:466-473.
Riesterer, Int'l J Radiation Oncology Biology Physics (2004) 361-368.
Roberts et al., Immunity (1999) 10:183-196.
Rodrigues et al., Mol. Cell. Biol. (2000) 20:1448-1459.
Rodriguez-Viciana et al., EMBO J. (1996) 15:2442-2451.
Roth et al., J. Immunol. Methods (1995) 188:97-116.
Rudd, Immunity (1996) 4:527-534.
Rupnick et al., Proc. Nat'l. Acad. Sci. (USA) (2002) 99:10730-35.
Sadhu et al., J. Immunol. (2003) 170:2647-2654.
Salven et al., Blood (1999) 94:3334-3339.
Salvesen et al., Cell (1997) 91:443-446.
Sasaki et al., Science (2000) 287:1040-1046.
Sauder et al., J. Am. Acad. Dermatol. (2002) 47:535-541.
Schimmer et al., J. Immunol. (1998) 160:1466-1471.
Schuch et al., Blood (2002) 100:4622-4628.
Schueneman et al., Canc. Res. (2003) 63:4009-4016.
Second Preliminary Amendment and Response to Notice to File Missing Parts of Nonprovisional Application from U.S. Appl. No. 12/575,277, filed Jan. 20, 2010.

Second Preliminary Amendment and Response to Notice to File Missing Parts of Nonprovisional Application from U.S. Appl. No. 12/575,367, filed Jan. 20, 2010.
Second Preliminary Amendment from U.S. Appl. No. 11/110,204, filed Aug. 24, 2007.
Second Preliminary Amendment from U.S. Appl. No. 11/884,566, filed May 13, 2008.
Sengupta et al., Circulation (2003) 107:2955-2961.
Sharman J. et al. (Nov. 2011). "A Phase I Study of the Selective Phosphatidylinositol 3-Kinase-Delta (PI3K Delta) Inhibitor, CAL-101 (GS-1101), in Combination with Rituximab and/or Bendamustine in Patients with Relapsed or Refractory Chronic Lymphocytic Leukemia (CLL)," Blood 118(21):779-780.
Shimamoto et al., Leukemia Res. (2003) 27:783-788.
Shiojima et al., Circ. Res. (2002) 90:1243-1250.
Shvidel et al., Hematol. J. (2002) 3:32-37.
Smith et al., Am. J. Respir. Cell Mol. Biol. (1996) 15(6):693-702.
Song et al., Canc. Res. (1974) 34:2344-2350.
Springer, Cell (1994) 76:301-314.
Stein et al., Mol. Med. Today (2000) 6:347-357.
Stenmark et al., J. Cell. Sci. (1999) 112:4175-4183.
Stennicke et al., Biochim. Biophys. Acta. (2000) 1477:299-306.
Stephens et al., Current Biology (1994) 4:203-214.
Stirewalt et al., Nat. Rev. Cancer (2003) 3:650-665.
Stoyanov et al., Science (1995) 269:690-693.
Su et al., Cancer Research (2003) 63:3585-3592.
Sumariwalla et al., Arthritis Res. Ther. (2002) 5:R32-R39.
Sunil et al., Respir. Res. (2002) 3:21.
Supplemental Amendment from U.S. Appl. No. 11/110,204, filed Oct. 27, 2009.
Supplemental Notice of Allowance from U.S. Appl. No. 10/337,192, mailed on Jun. 29, 2004.
Reeder, C.B. et al. (Oct. 26, 2010). "Novel Therapeutic Agents for B-Cell Lymphoma: Developing Rational Combinations," Blood 117(5): 1453-1462.
Tager et al., J. Exp. Med. (2000) 192:439-446.
Talento et al., Transplantation (1993) 55:418-422.
Tamiya et al., Immunopharmacology (1995) 29:53-63.
Tan et al., Cancer Research (2003) 63:7663-7667.
Tan et al., J. Immunol. Meths. (2000), 238:59-68.
Tan, J. et al. (Sep. 1, 2004). "A Specific Antagonist of the p110-Delta Catalytic Component of P13 Kinase, IC486068, Enhances Radiation-Induced Tumor Vascular Destruction," *International Journal of Radiation: Oncology Biology Physics* 60(1):S195.
Tanaka et al., J. Immunol. (1993) 151:5088-5095.
Tang et al., J. Biol. Chem. (1999) 274:16741-16746.
Taylor et al., Curr. Opin. Rheumatol. (2005) 17(3):293-298.
Tesar et al., Med. Sc. Monit. (2002) 8:BR24-BR29.
The Merck Manual on "arthritis" (2008).
The Merck Manual on "rheumatoid arthritis" (2008).
The Merck Manual, 17th ed, (1999) p. 1001.
Thelan et al., Proc. Natl. Acad. Sci. (USA) (1994) 91:4960-4964.
Ting et al., Int. J. Rad. Biol. (1991) 60:335-339.
U.S. Appl. No. 12/732,124, filed by Fowler et al. on Mar. 25, 2010.
U.S. Appl. No. 12/732,128, filed by Fowler et al. on Mar. 25, 2010.
Vacca et al., Blood (1999) 9:3064-3073.
Van Dijk et al., Blood (2000) 96:3406-3413.
Vanhaesebroeck et al., FASEB J. (1996) 10:A1395, Abst. No. 2280.
Vanhaesebroeck et al., Proc. Natl. Acad. Sci., (USA) (1997) 94:4330-4335.
Vanhaesebroeck et al., TIBS (1997) 22:267-272.
Vippagunta, S.R. et al. (2001). "Crystalline Solids," *Advanced Drug Delivery* 48:3-26.
Vivanco et al., Nat. Rev. Cancer (2002) 2:489-501.
Vlahos et al., J. Immunol. (1995) 154:2413-2422.
Volinia et al., EMBO J. (1995) 14:3339-3348.
Volinia et al., Genomics (1994) 24:472-477.
Volinia et al., Oncogene (1992) 7:789-793.
Webb, H.K. et al. (Apr. 2009). "CAL-101, a Potent and Selective Inhibitor of the Class 1 Phosphatidylinositol 3 Kinase (PI3K) p110δ: Preclinical Summary," *Proceedings of the American Association for Cancer Research* 50:894-895, Abstract No. #3703.
Wegner et al., Lung (1992) 170:267-279.

Wegner et al., Science (1990) 247:456-459.
Weiner et al., Nat. Cell Biol. (1999) 1:75-81.
Weyand et al., Arthritis & Rheumatism (2000) 43:1041-1048.
Williams, D.A. et al. (2002). *Foye's Principles of Medicinal Chemistry*, Lippincott, Williams & Wilkins, Baltimore MD, Fifth Edition, pp. 50 and 59-61.
Williams, Methods Mol. Med. (2004) 98:207-216.
Wolff, ed., Burger's Medicinal Chemistry and Drug Discovery, 5th edition (1996) vol. 1, New York: John Wiley & Sons, pp. 975-977.
Written Opinion of the International Searching Authority for PCT/US2009/064471, Mailed on Feb. 12, 2010, 5 pages.
Written Opinion mailed on Dec. 5, 2011, for PCT Application No. PCT/US2011/053102, filed on Sep. 23, 2011, 6 pages.
Written Opinion mailed on Jan. 21, 2012 for PCT Application No. PCT/US2010/042801, filed on Jul. 21, 2010, 10 pages.
Written Opinion mailed on Jun. 14, 2012 for PCT Application No. PCT/US2012/028654, filed on Mar. 9, 2012, 11 pages.
Wymann et al., Biochem. Biophys. Acta. (1998) 1436:127-150.
Wymann et al., Biochem. J. (1994) 298:517-520.
Wymann et al., Trends Immunol. Today (2000) 21:260-264.
Xing et al., Am. J. Pathol. (1993) 143:1009-1015.
Xu et al., Blood (2003) 102:972-980.
Yamasawa et al., Inflammation (1999) 23:263-274.
Yamaura et al., Int. J. Rad. Biol. (1976) 30:179-187.
Yao et al., Science (1995) 267:2003-2006.
Yum et al., J. Immunol. (2001) 167:6601-6608.
Zeng et al., Transplantation (1994) 58:681-689.
Zhao et al., Leukemia (2004) 18:267-75.
Anonymous. (2006). "Cardiovascular Disease: Treatment for Stroke", Stanford Hospital & Clinics, located at <httpL//www.stanfordhospital.com/healthLib/atoz/cardiac/stktreat.html>, last visited on Sep. 19, 2006, 2 pages.
Marchione, M. et al. (2006). "Drugs hold promise in kidney cancer fight", located at <http://www.ledger-enquirer.com/mld/ledgerenquirer/living/health/14744763.htm, last visited on Sep. 2, 2006, 3 pages.
Anonymous. (2006). "Heart Disease", WebMD, located at <http://www.wedmd.com/content/pages/9/1675_57842.htm> as retrieved on Sep. 14, 2006, 1 page.
Anonymous. (2010). "Multiple Sclerosis", located at <http://www.health.nytimes.com/health/guides/disease/multiple-sclerosis/overview.html>, last visited Aug. 1, 2010, 4 pages
Anonymous. (2004). "NIH Heart Disease & Stroke Research: Fact Sheet", American Heart Association, located at <http://www.americanheart.org/presenter.jhtml?identifier=3010188>, last visited Feb. 17, 2004, 1 page.
Anonymous. (2010). "Spinal Cord Injury", located at <http://www.medicinenet.com/spinal_cord_injury/page5.htm>, last visited on Aug. 1, 2010, 3 pages.
Anonymous. (2010) "Systemic Lupus Erythematosus", located at <http://www.nim.nih.gov/medlineplus/ency/article/000435.htm>, last visited Aug. 1, 2010, 4 pages.
Anonymous. (Mar. 16, 2010). "Study to Investigate CAL-101 in Combination with Chemotherapeutic Agents and CD20 mAb in Patients with Relapsed and Rituximab or Refractory Indolent B-Cell Non-Hodgkin's Lymphoma, Mantle Cell Lymphoma or Chronic Lymphocytic Leukemia," <http://clinicaltrials.gov/ct2/show/study/NCT01088048>, last visited Jul. 24, 2012, 4 pages.
Anonymous. (Sep. 16, 2010). "A Phase 2 Single Arm Study to Investigate the Safety and Clinical Activity of CAL-101 in Combination with Rituximab in Elderly Patients with Previously Untreated Chronic Lymphocytic Leukemia or Small Lymphocytic Lymphoma," located at <http://clinicaltrials.gov/archive/NCT01203930/2010_09_16>, last visited Jul. 24, 2012, 4 pages.
Burgering, B.M. et al. (Aug. 17, 1995). "Protein Kinase B (c-Akt) in Phosphatidylinositol3-Oh Kinase Signal Transduction," *Nature* 376:599-602.
Chern et al., Chemical Abstracts (1998) 129(16):676.
Cheson et al., *The New England Journal of Medicine* (2008) 359(6):613-626.
Chiba, K. et al. (Jun. 1, 2009). "Multiple Osteolytic Bone Lesions with High Serum Levels of Interleukin-6 and CCL Chemokines in a Patient with Adult T Cell Leukemia," *International Journal of Laboratory Hematology* 31(3):368-371.

Coligan et al., *Current Protocols in Protein Science* (2002) 3:15-20.

Constantin et al., *Immunity* (2000) 13:759-769.

Eisenkraft, A. et al. (Oct. 1, 2006, e-published Mar. 3, 2006). "MCP-1 in the Cerebrospinal Fluid of Children with Acute Lymphoblastic Leukemia," *Leukemia Research* 30(10): 1259-1261.

El-Feky, S.A. et al. (1985). "Synthesis of Certain New Sulfur-Containing Quinazolinone Derivatives Likely to Possess CNS Depressant Action," *Egyptian Journal of Pharmaceutical Sciences* 24(1-4):39-47.

Fraser et al., *Science* (1991) 251:313-316.

Fruman et al., *Ann. Rev. Biochem.* (1998) 67:481-507.

Hattori, N. et al. (May 1, 2010). "Over-Expression of CCL3??MIP-1[Alpha] in a Blastoid Mantle Cell Lymphoma with Hypercalcemia," *European Journal of Haematology* 84(5):448452.

Hsieh, S.N. (2003). "Identification of PI3Kγ in Endothelial Cells and Its Involvement in Sphingosine 1-Phosphate Mediated Endothelial Cell Migration," Dissertation, Friedrick Schiller University, Jena, Germany, 104 pages.

Hunter, *Cell* (1995) 83:1-4.

Ismail and Sayed, *Indian Journal of Chemistry* (1982) 21B(5):461-462.

Jares et al., *Nat. Rev. Cancer* (2007) 7(10):750-762.

Jordan, *Nature Reviews: Drug Discovery* (2003) 2:205-213.

Mazur, G. et al. (Jan. 1, 2007). "Increased Monocyte Chemoattractant Protien 1 (MCP-1/CCL-2) Serum Level in Acute Myeloid Leukemia," *Neoplasma* 54(5):285-289.

Mori, N. (Sep. 10, 2004). "Elevated Expression of CCL5/RANTES in Adult T-Cell Leukemia Cells: Possible Transactivation of the CCL5 Gene by Human T-Cell Leukemia Virus Type I Tax," *International Journal of Cancer* 111(4): 548-557.

Morton et al., *Blood* (2006) 107(1):265-276.

Niens, M. et al. (Mar. 1, 2008). "Serum Chemokine Levels in Hodgkin Lymphoma Patients: Highly Increased Levels of CCL17 and CCL22," *British Journal of Haematology* 140(5):527-536.

Okada, Y. et al. (Mar. 15, 2004). "Macrophage Inflammatory Protein-1[Alpha] Induces Hypercalcemia in Adult T-Cell Leukemia," *Journal of Bone and Mineral Research* 19(7):1105-1111.

Olsnes, A.M. et al. (Jul. 1, 2006). "T Lymphocyte Chemotactic Chemokines in Acute Myelogenous Leukemia (AML): Local Release by Native Human AML Blasts and Systemic Levels of CXCL10 (IP-10), CCL5 (RANTES) and CCL17 (TARC)," *Cancer Immunology, Immunotherapy* 55(7):830-840.

Parasharya et al., Chemical Abstracts (1994) vol. 121, No. 9, p. 1065.

Pietersz et al., *Immunol. Rev.* (1992) 129:57-80.

Rowlinson-Busza et al., *Curr. Opin. Oncol.* (1992) 4:1142-1148.

Schrottner, P. et al. (May 1, 2010). "The Role of Chemokines in B Cell Chronic Lymphocytic Leukaemia: Pathophysiological Aspects and Clinical Impact," *Annals of Hematology* 89(5):437-446.

Sujobert et al., *Blood* (2005) 106(3):1063-1066.

Sutton, a. (Jun. 9, 2006). "Baylor, St. Luke's study uses gene therapy as pancreatic cancer", located at <http://www.bcm.edu/news/item.cfm%3FnewsID=640>, last visited on Sep. 2, 2006, 2 pages.

Trail et al., *Science* (1993) 261:212-215.

Wierda, *Hematology* (2006) 285-294.

Williams et al., *Chemistry & Biology* (2010) 17:123-134.

\* cited by examiner

| Diluent | Sample | Solubility (mg/mL) | % of Compound 1 |
|---|---|---|---|
| H₂O | 1 | 0.005525 | |
| | 1 (R) | 0.007540 | 136 |
| | 1 (S) | 0.006393 | 116 |
| pH 2 | 1 | 0.2898 | |
| | 1 (R) | 0.4818 | 166 |
| | 1 (S) | 0.3524 | 122 |
| pH 4 | 1 | 0.01290 | |
| | 1 (R) | 0.01987 | 154 |
| | 1 (S) | 0.01473 | 114 |
| pH 6 | 1 | 0.005527 | |
| | 1 (R) | 0.009384 | 170 |
| | 1 (S) | 0.006368 | 115 |
| pH 8 | 1 | 0.005176 | |
| | 1 (R) | 0.009213 | 178 |
| | 1 (S) | 0.006114 | 118 |
| PEG 400 | 1 | 4.554 | |
| | 1 (R) | 4.073 | 89 |
| | 1 (S) | 4.430 | 87 |

*FIG. 4*

| Compound | | 1 | 1 (S) | 1 (R) |
|---|---|---|---|---|
| BioChemical IC$_{50}$ (nM) | p110α | 100,000 | 72,300 | 72,400 |
| | p110β | 20,400 | 3,175 | 2,490 |
| | p110δ | 18.4 | 19.3 | 21.6 |
| | p110γ | 4,410 | 895 | 1,040 |

*FIG. 5A*

| Compound | | 1 | 1 (S) | 1 (R) |
|---|---|---|---|---|
| Cell-based assay EC$_{50}$ (nM) | p110α | >20,000 | >20,000 | >20,000 |
| | p110δ | 2,500 | 1,600 | 800 |
| | p110γ | 20,000 | ND | ND |

*FIG. 5B*

ATROPISOMERS OF 2-PURINYL-3-TOLYL-QUINAZOLINONE DERIVATIVES AND METHODS OF USE

CROSS-REFERENCE TO RELATED APPLICATIONS

This application claims priority from U.S. provisional application Nos. 61/162,980 filed Mar. 24, 2009; and 61/231,550 filed Aug. 5, 2009. The contents of these documents are incorporated herein by reference.

TECHNICAL FIELD

The invention is in the field of therapeutics and medicinal chemistry for the treatment of inflammatory conditions and/or oncology disorders using compounds that inhibit phosphatidylinositol-3,4,5-triphosphate kinase δ (PI3Kδ) enzymes in vivo. In particular, the invention concerns compounds, compositions, and methods of treatment of inflammatory conditions and/or oncology disorders with enantiomerically enriched 2-((6-amino-9H-purin-9-yl)methyl)-5-methyl-3-o-tolylquinazolin-4(3H)-one.

Cell signaling via 3'-phosphorylated phosphoinositides has been implicated in a variety of cellular processes, e.g., malignant transformation, growth factor signaling, inflammation, and immunity. The enzyme responsible for generating these phosphorylated signaling products, phosphatidylinositol 3-kinase (PI 3-kinase; PI3K), was originally identified as an activity associated with viral oncoproteins and growth factor receptor tyrosine kinases that phosphorylates phosphatidylinositol (PI) and its phosphorylated derivatives at the 3'-hydroxyl of the inositol ring. Furthermore, PI3K activation, is believed to be involved in a range of cellular responses including cell growth, differentiation, and apoptosis.

Identification of the p110δ isoform of phosphatidylinositol 3-kinases (PI 3-kinases; PI3Ks) is described in Chantry, et al., *J Biol Chem* (1997) 272:19236-19241. It was observed that the human p110δ isoform is expressed in a tissue-restricted fashion. It is expressed at high levels in lymphocytes and lymphoid tissues, suggesting that the protein might play a role in PI 3-kinase-mediated signaling in the immune system. In addition particular isoforms of PI3K may also play a role in PI3K-mediated signaling in certain cancers.

Inflammatory responses are notably associated with the influx of leukocytes and/or leukocyte chemotaxis. Inflammatory responses may result from infection with pathogenic organisms and viruses, noninfectious means such as trauma or reperfusion following myocardial infarction or stroke, immune responses to foreign antigens, and autoimmune diseases. Leukocytes provide a first line of immune defense against many common microorganisms.

Lee, et al., *FASEB J.* (2006) 20:455-465 describes evidence that inhibition of PI3Kδ attenuates allergic airway inflammation and hyperresponsiveness in murine asthma models, demonstrating that selective inhibitors of PI3Kδ are useful to treat asthma and allergic reactions as well as immune disorders.

With regards to cancer, compounds that express relatively high levels of p110δ may be useful for treating mainly hematologic cancers. The p110β isoform of PI3K may also play a role in PI3K-mediated signaling in certain cancers, such as solid tumors.

There is a need for a treatment of PI3K-mediated disorders relating to cancers and inflammatory conditions. The present invention provides a specific isomer of one quinazolinone compound that is particularly useful for the treatment of inflammatory conditions and cancer.

DISCLOSURE OF THE INVENTION

The invention relates to selective PI3Kδ inhibitors and methods to treat inflammatory conditions and cancers with compounds that are selective PI3Kδ inhibitors. In particular, compounds of the invention exist as separable atropisomers and the invention provides separated atropisomers having unexpected advantages over mixtures of atropisomers for use in treatment of inflammation. The compounds, compositions, and methods of the invention are therapeutically beneficial in treating inflammatory conditions.

In one aspect, the invention provides an optically active compound comprising an atropisomer of formula 1(S)

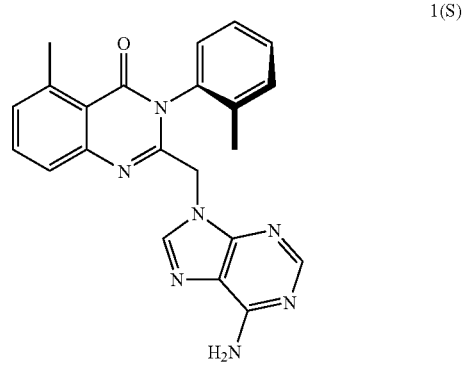

1(S)

or a pharmaceutically acceptable salt or solvate thereof; wherein the atropisomer of formula 1(S) is present in excess of its corresponding enantiomer of formula 1(R)

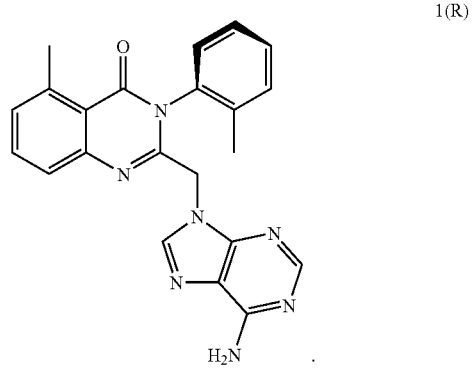

1(R)

In another aspect, the invention provides an optically active compound comprising an atropisomer of formula 1(R)

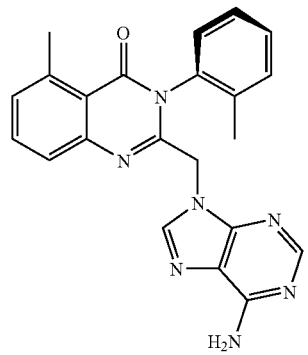

1(R)

or a pharmaceutically acceptable salt or solvate thereof; and wherein the atropisomer of formula 1(R) is present in excess of its corresponding enantiomer of formula 1(S)

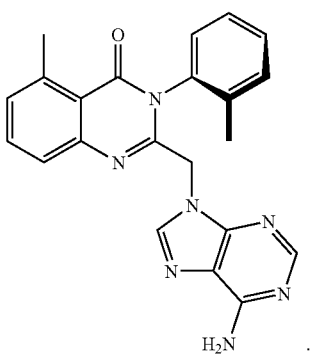

1(S)

In another aspect, the invention provides a composition comprising an optically active compound described herein, and a pharmaceutically acceptable carrier. In another aspect, the invention provides a method of treating a condition in a mammal, wherein the condition is characterized by inflammation. In some embodiments, the condition is selected from the group consisting of chronic inflammatory diseases, tissue or organ transplant rejections, graft versus host disease (GVHD), multiple organ injury syndromes, acute glomerulonephritis, reactive arthritis, hereditary emphysema, chronic obstructive pulmonary disease (COPD), cystic fibrosis, adult respiratory distress syndrome (ARDS), ischemic-reperfusion injury, stroke, rheumatoid arthritis (RA), osteoarthritis (OA), asthma, allergic rhinitis, lupus nephritis, Crohn's disease, ulcerative colitis, necrotizing enterocolitis, pancreatitis, *Pneumocystis carinii* pneumonia (PCP), inflammatory bowel disease (IBD), severe acute respiratory syndrome (SARS), sepsis, community acquired pneumonia (CAP), multiple sclerosis (MS), myocardial infarction, respiratory syncytial virus (RSV) infection, dermatitis, acute purulent meningitis, thermal injury, granulocyte transfusion associated syndromes, cytokine-induced toxicity, and spinal cord injury; which comprises administering to said mammal a therapeutically effective amount of an optically active atropisomer described herein. In certain embodiments, the optically active compound is represented by formula 1(S). In other embodiments, the optically active compound is represented by formula 1(R).

In another aspect, the invention provides an optically active atropisomer obtained by chiral chromatographic separation of a racemic mixture, of formula 1

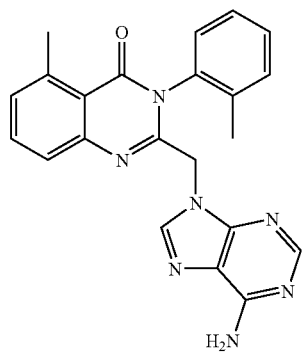

(1)

or a pharmaceutically acceptable salt or solvate thereof; wherein a racemic of formula 1 is separated using a normal phase chiral column, and two peaks, A and B, are resolved, wherein peak A and peak B represent the atropisomers, 1(S) and 1(R), respectively,

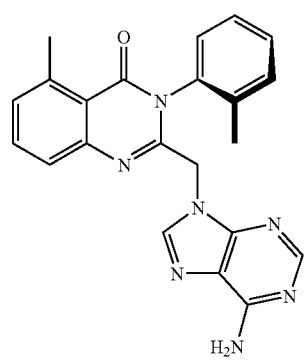

1(S)

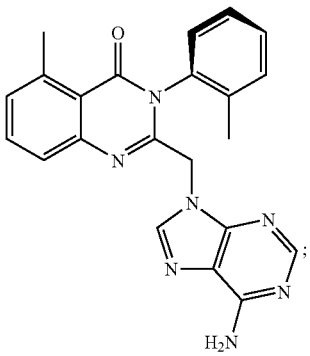

1(R)

and wherein the optically active atropisomer obtained consists predominantly of the first isomer to elute from the column. In certain embodiments, the optically active atropisomer obtained consists of the compound of formula 1(S) substantially free of the compound of formula 1(R).

In another embodiment, the optically active atropisomer obtained consists of the compound of formula 1(R) substantially free of the compound of formula 1(S).

In yet another aspect, the invention provides an optically active atropisomer obtained by chiral chromatographic separation of a racemic of formula 1

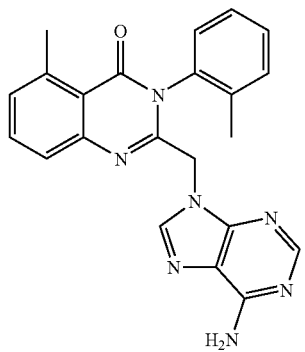 [SMILES: Cc1ccccc1-n1c(Cn2cnc3c(N)ncnc32)nc2cccc(C)c2c1=O]

(1)

or a pharmaceutically acceptable salt or solvate thereof; wherein a racemic mixture of formula 1 is separated using a normal phase chiral column, and two peaks, A and B, are resolved, wherein peak A and peak B represent the atropisomers, 1(S) and 1(R), respectively,

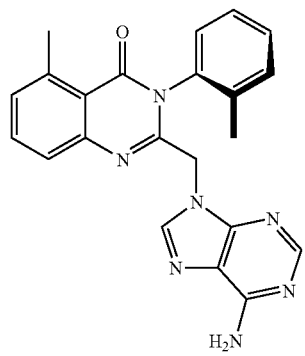

1(S)

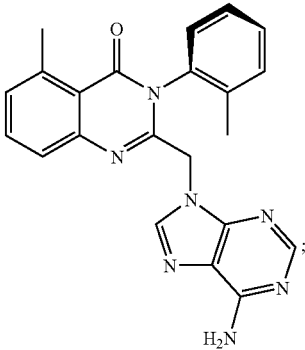

1(R)

and wherein the optically active atropisomer obtained consists predominantly of the second isomer to elute from the column.

In another aspect, the invention provides pharmaceutical compositions comprising any of the optically active compounds described herein, and at least one pharmaceutically acceptable excipient.

BRIEF DESCRIPTION OF THE DRAWINGS

FIG. 4 shows solubility data of compound 1 and the resolved atropisomers, 1(S) and 1(R), in a series of aqueous solvents.

FIG. 5 shows the differences in p110 activity of different isoforms between racemic compound 1 and the atropisomers 1(S) and 1(R) in biochemical (FIG. 5A) and cell-based assays (FIG. 5B).

DETAILED DESCRIPTION

Figure 1:
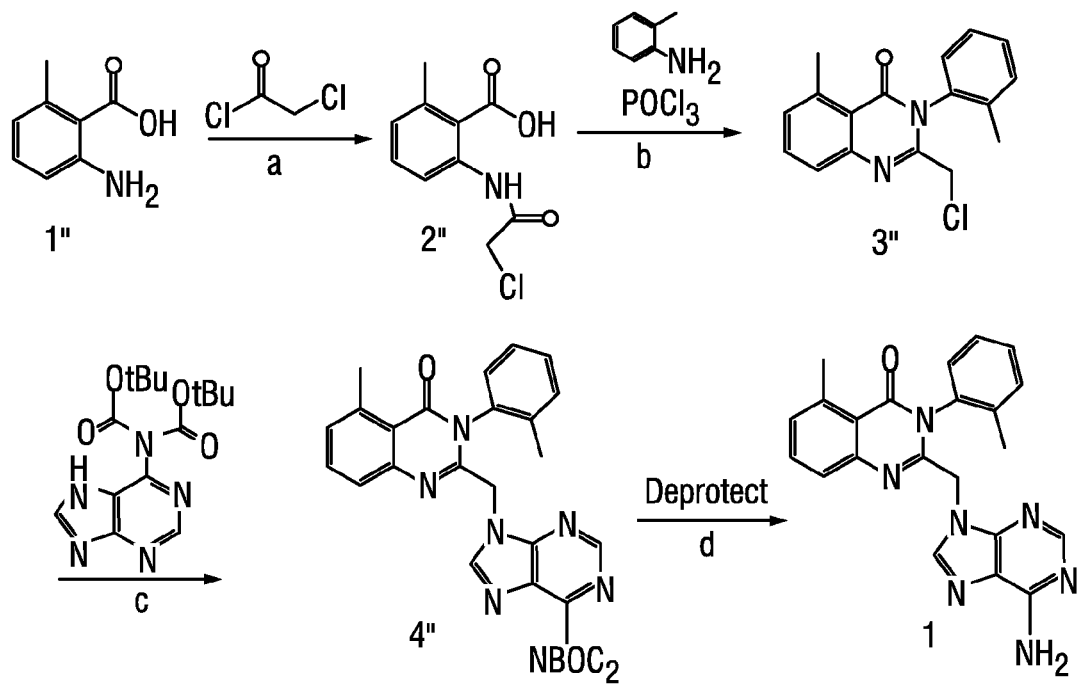
FIG. 1 shows a synthetic scheme of the preparation of racemic compound 1.

Many organic compounds exist in optically active forms, i.e., they have the ability to rotate plane-polarized light. The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these compounds, called stereoisomers, are identical except that they are mirror images of one another. Stereoisomers that are mirror images of one another may also be referred to as enantiomers, and a mixture of such isomers is often called an enantiomeric mixture. A 50:50 mixture of enantiomers is referred to as a racemic mixture or a racemate. The terms "racemic mixture" and "racemate" refer to an equimolar mixture of two enantiomeric species, which is devoid of optical activity.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

The term "enantiomers" as used herein, refers to two stereoisomers of a compound.

The term "atropisomers" refers to conformational stereoisomers which occur when rotation about a single bond in the molecule is prevented, or greatly slowed, as a result of steric interactions with other parts of the molecule and the substituents at both ends of the single bond are asymmetrical, i.e., they do not require a stereocenter. Where the rotational barrier about the single bond is high enough, and interconversion between conformations is slow enough, separation and isolation of the isomeric species may be permitted. Atropisomers are enantiomers without a single asymmetric atom.

The energy barrier to thermal racemization of atropisomers may be determined by the steric hindrance to free rotation of one or more bonds forming a chiral axis. Certain biaryl compounds exhibit atropisomerism where rotation around an interannular bond lacking C2 symmetry is restricted. The free energy barrier for isomerization (enantiomerization) is a measure of the stability of the interannular bond with respect to rotation. Optical and thermal excitation can promote racemization of such isomers, dependent on electronic and steric factors.

Ortho-substituted biphenyl compounds may exhibit this type of conformational, rotational isomerism. Such biphenyls are enantiomeric, chiral atropisomers where the sp2-sp2 carbon-carbon, interannular bond between the phenyl rings has a sufficiently high energy barrier to prevent free rotation, and where substituents X≠Y and U≠V render the molecule asymmetric.

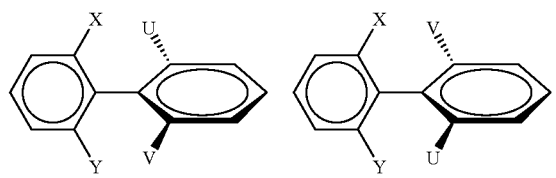

The steric interaction between X:U, X:V, and/or Y:V, Y:U is large enough to make the planar conformation an energy maximum. Two non-planar, axially chiral enantiomers then exist as atropisomers when their interconversion is slow enough such that they can be isolated free of each other. By one definition, atropisomerism is defined to exist where the isomers have a half-life, $t_{1/2}$, of at least 1,000 seconds, which is a free energy barrier of 22.3 kcal mol$^{-1}$ (93.3 kJ mol$^{-1}$) at 300K (Oki, M. "Recent Advances in Atropisomerism," *Topics in Stereochemistry* (1983) 14:1). Bold lines and dashed lines in the figures shown above indicate those moieties, or portions of the molecule, which are sterically restricted due to a rotational energy barrier. Bolded moieties exist orthogonally above the plane of the page, and dashed moieties exist orthogonally below the plane of the page. The 'flat' part of the molecule (the left ring in each of the two depicted biphenyls) is in the plane of the page.

Compounds with axial chirality, such as chiral biphenyl rings, can be described using configurational nomenclature. For example, 2,2'; 6,6'-tetra substituted biphenyls are assigned the configurational descriptors as other axially chiral molecules. The molecules can be viewed from either end of the chiral axis and it leads to the same configurational descriptor (R or S). When, for instance, the molecule 2 is viewed from the left hand side along the 1-1' bond, one arrives at projection 2.1 while the projection 2.2 is reached when the same molecule is now viewed from the right hand end along the 1'-1 bond. These projections conform to (S) configuration.

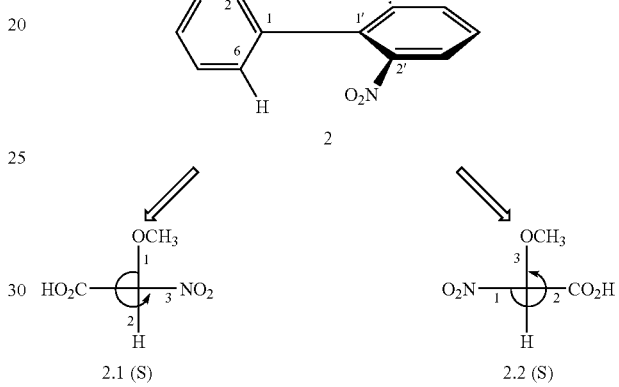

The S designation is assigned by applying sequence rules to name compounds with axial chirality. These rules are applied to primarily the ortho substituents of the biphenyl ring. The two linked rings may be represented by a horizontal and a vertical line. The lines represent the two orthogonal rings; and the ends of the lines represent the substituents at the four ortho positions of the two linked rings. These lines thus join each pair of ortho substituents. The two groups on the nearest ring (the 'front' line) take precedence over the two far groups. Within the pair, substituents are assigned priorities using the same priority rules used for describing R and S enantiomers of a chiral center. For example, in the projection formula 2.1 above, the perspective is viewing the molecule from the left side, looking down the axis from 1 to 1'. The near ring is represented by the bold vertical line connecting —OCH$_3$ and H, which are numbered 1 and 2, respectively, since —OCH$_3$ has a higher priority over H. The horizontal line represents the ring containing NO$_2$ and CO$_2$H, which are numbered 3 and 4, respectively, based on their priority. Thus, the sequence 1->2->3, reveals the configurational descriptor, which in this example is S, because following the numerical sequence in order requires going counter clockwise around the center of the diagram. As done for enantiomers, the numbered substituents are then taken in sequence by traveling either clockwise or counterclockwise around the point where the two lines intersect. If the path around the center point had been clockwise, the atropisomer would be designated R, just as it is for enantiomers of a stereocenter.

The same S configuration is deduced from viewing the molecule from the opposite end of the 1-1' axis, as shown in FIG. 3.2. From this perspective, the ring containing the ortho NO$_2$ and ortho CO$_2$H is closer to the viewer and is represented by the bold horizontal line. The ring containing ortho OCH$_3$ and ortho H is further from the viewer and is represented by the vertical line.

In this biphenyl example, only the four ortho substituents are selected for nomenclature purposes. In the case wherein two ortho substituents in a ring are identical, the priority is given by considering meta substituents in the same ring.

This type of nomenclature assignment will be applied to the atropisomers described herein. For instance, compound 3, which is representative of a portion of the some of the compounds herein, such as compound 1(S), is assigned an absolute configuration of S as shown below.

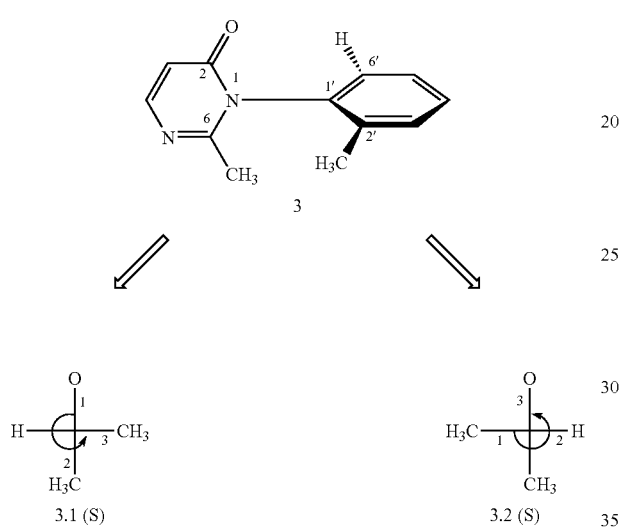

For purposes of the invention, the atropisomers are preferably sufficiently stable to be stored and used without substantial thermal interconversion. Typically, the atropisomers have a half-life of greater than 1 week when in solid form at room temperature.

In one embodiment, the compound of formula 1,2-((6-amino-9H-purin-9-yl)methyl)-5-methyl-3-o-tolylquinazolin-4(3H)-one, has two atropisomers represented by formulas 1(S) and 1(R). Formula 1 represents a mixture of equal amounts of the two atropisomers 1(S) and 1(R). Formula 1(R) is the corresponding enantiomer of formula 1(S) and vice versa.

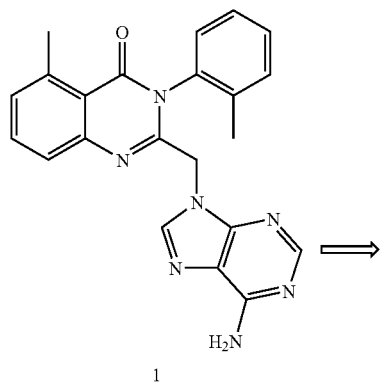

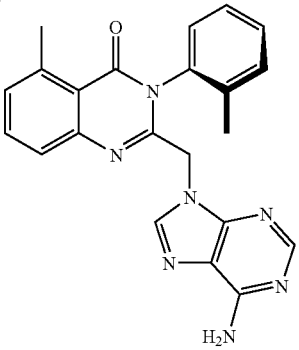

1(S)

Atropisomers

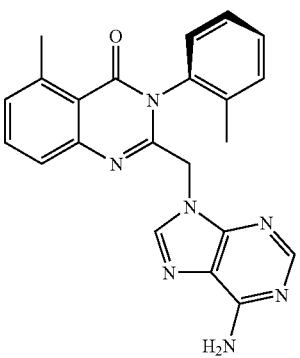

1(R)

As used herein, an atropisomer "substantially free" of its corresponding enantiomer means that the composition contains at least 90% by weight of one atropisomer, and 10% by weight or less of its stereoisomeric atropisomer. In some embodiments, the composition contains at least 95% by weight of one atropisomer and 5% by weight or less of its stereoisomer. In some embodiments, the composition contains at least 98% by weight of one atropisomer and 2% by weight or less of its stereoisomer. Alternatively, the relative amounts of the predominant isomer and any of the minor enantiomer is at least 9:1, or at least 19:1, or at least 98:2. In some embodiments, the composition contains at least 99% by weight of one atropisomer and 1% by weight or less of its stereoisomer. In some embodiments, the composition contains at least 99.5% by weight of one atropisomer and 0.5% by weight or less of its stereoisomer.

The atropisomeric compounds of the invention are typically solid materials, and are optionally purified to greater than about 90% purity, even if they exist as a mixture of atropisomers. In certain embodiments, the atropisomeric compound of the invention is substantially free of proteinaceous materials, or any materials having a molecular weight over about 1000 amu. Typically, they are at least 90% pure (chemically pure, regardless of optical purity), and preferably at least 95% chemically pure.

In some embodiments, the compositions and methods of the invention utilize an optically active form of the compounds described, meaning in each instance, the compound is optically active and contains predominantly the S-stereoisomer, such as 1(S), although it may contain the R-stereoisomer, such as 1(R), as a minor component. In other embodiments, the compound is optically active and contains predominantly the R-stereoisomer, such as 1(R), although it may contain the S-stereoisomer, such as 1(S), as a minor component. For clarity, where a dosage of a compound is described herein, the dosage refers to the weight of the compound including each stereoisomer that is present. Thus, a dosage of 100 mg of compound 1(S) as used herein, for example, refers to the weight of the mixture of stereoisomers rather than the weight of the S-stereoisomer specifically. It could, for example, refer to 100 mg of a 9:1 mixture of S and R stereoisomers, which would contain about 90 mg of the S stereoisomer, or to 100 mg of a 19:1 mixture of S and R stereoisomers, which would contain about 95 mg of the S stereoisomer.

In certain embodiments, the compound is preferably a non-racemic mixture wherein the S isomer is the major component of the mixture. Typically such mixture will contain no more than about 10% of the R isomer, meaning the ratio of S to R isomers is at least about 9:1, and preferably less than 5% of the R-isomer, meaning the ratio of S to R enantiomers is at least about 19:1. In some embodiments the compound has less than 2% R enantiomer, meaning it has an enantiomeric excess of at least about 96%. In some embodiments, the compound has an enantiomeric excess of at least 98%. In some embodiments, the compound has an enantiomeric excess of at least 99%.

In certain embodiments, the compound is preferably a non-racemic mixture wherein the R isomer is the major component of the mixture. Typically such mixture will contain no more than about 10% of the S isomer, meaning the ratio of R to S isomers is at least about 9:1, and preferably less than 5% of the S-isomer, meaning the ratio of R to S enantiomers is at least about 19:1. In some embodiments the compound has less than 2% S enantiomer, meaning it has an enantiomeric excess of at least about 96%. In some embodiments, the compound has an enantiomeric excess of at least 98%. In some embodiments, the compound has an enantiomeric excess of at least 99%.

An atropisomer which is present "in excess" of its corresponding enantiomer or an "enantioenriched mixture" means that the atropisomer is present in an amount greater than its enantiomer, making the atropisomer mixture optically active. Typically this means the compound present "in excess" predominates by at least a 60/40 ratio over its enantiomer.

The invention relates to selective PI3Kδ inhibitors and methods to treat inflammatory conditions and/or oncology disorders with compounds that are selective PI3Kδ inhibitors. In particular, compounds of the invention exist as separable atropisomers and the invention provides separated atropisomers having unexpected advantages over mixtures of atropisomers for use in treatment of inflammation. The compounds, compositions, and methods of the invention are therapeutically beneficial in treating inflammatory conditions.

In one aspect, the invention provides an optically active compound comprising an atropisomer of formula 1(S)

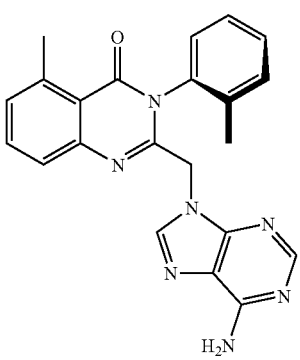

or a pharmaceutically acceptable salt or solvate thereof; and wherein the atropisomer of formula 1(S) is present in excess of its corresponding enantiomer of formula 1(R)

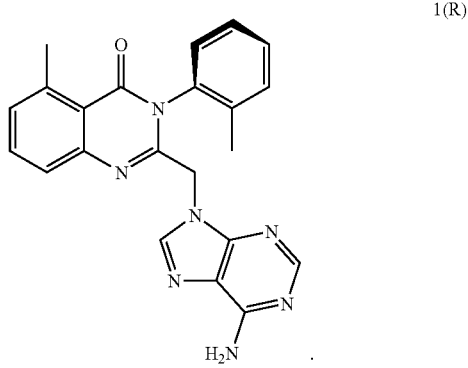

In one embodiment, the atropisomer of formula 1(S) is substantially free of its corresponding atropisomer of formula 1(R).

In another aspect, the invention provides an optically active compound comprising an atropisomer of formula 1(R)

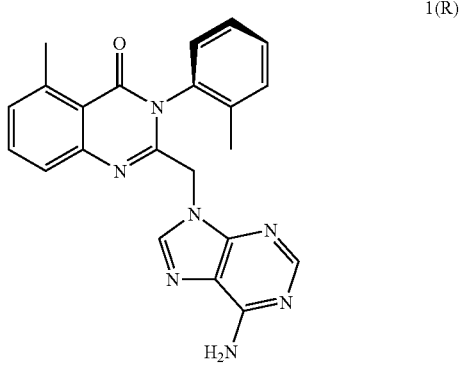

or a pharmaceutically acceptable salt or solvate thereof; and wherein the atropisomer of formula 1(R) is present in excess of its corresponding enantiomer of formula 1(S)

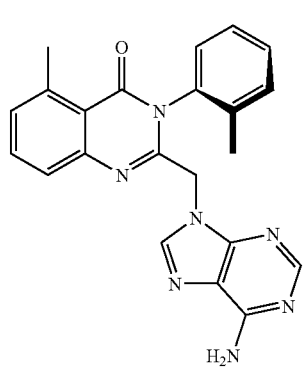

In certain embodiments, the atropisomer of formula 1(R) is substantially free of its corresponding atropisomer of formula 1(S).

In another aspect, the invention provides a pharmaceutical composition comprising any of the optically active compounds described herein, and at least one pharmaceutically acceptable excipient. In particular embodiments, the optically active compound is 1(S) or 1(R). In other embodiments, the optically active compound is 1(S). In yet other embodiments, the optically active compound is 1(R).

In one embodiment, the composition comprises a therapeutically effective amount of the optically active atropisomer for the treatment of a condition, wherein the condition is characterized by inflammation. In some embodiments, the condition is selected from the group consisting of chronic inflammatory diseases, tissue or organ transplant rejections, graft versus host disease (GVHD), multiple organ injury syndromes, acute glomerulonephritis, reactive arthritis, hereditary emphysema, chronic obstructive pulmonary disease (COPD), cystic fibrosis, adult respiratory distress syndrome (ARDS), ischemic-reperfusion injury, stroke, rheumatoid arthritis (RA), osteoarthritis (OA), asthma, allergic rhinitis, diabetes, lupus nephritis, Crohn's disease, ulcerative colitis, necrotizing enterocolitis, pancreatitis, *Pneumocystis carinii* pneumonia (PCP), inflammatory bowel disease (IBD), severe acute respiratory syndrome (SARS), sepsis, community acquired pneumonia (CAP), multiple sclerosis (MS), myocardial infarction, respiratory syncytial virus (RSV) infection, dermatitis, acute purulent meningitis, thermal injury, granulocyte transfusion associated syndromes, cytokine-induced toxicity, and spinal cord injury. In certain embodiments, the optically active compound is represented by formula 1(S). In other embodiments, the optically active compound is represented by formula 1(R).

In another aspect, the invention provides a method of treating a condition in a mammal, wherein the condition is characterized by inflammation. In some embodiments, the condition is selected from the group consisting of chronic inflammatory diseases, tissue or organ transplant rejections, graft versus host disease (GVHD), multiple organ injury syndromes, acute glomerulonephritis, reactive arthritis, hereditary emphysema, chronic obstructive pulmonary disease (COPD), cystic fibrosis, adult respiratory distress syndrome (ARDS), ischemic-reperfusion injury, stroke, rheumatoid arthritis (RA), osteoarthritis (OA), asthma, allergic rhinitis, diabetes, lupus nephritis, Crohn's disease, ulcerative colitis, necrotizing enterocolitis, pancreatitis, *Pneumocystis carinii* pneumonia (PCP), inflammatory bowel disease (IBD), severe acute respiratory syndrome (SARS), sepsis, community acquired pneumonia (CAP), multiple sclerosis (MS), myocardial infarction, respiratory syncytial virus (RSV) infection, dermatitis, acute purulent meningitis, thermal injury, granulocyte transfusion associated syndromes, cytokine-induced toxicity, and spinal cord injury; which comprises administering to said mammal a therapeutically effective amount of an optically active atropisomer described herein. In certain embodiments, the optically active compound is represented by formula 1(S). In other embodiments, the optically active compound is represented by formula 1(R). In some embodiments, the mammal is one identified as in need of treatment for the disorder. In some embodiments, the mammal is one at risk of the condition and the compound or composition is administered to reduce or prevent the occurrence of inflammation. A method of the present invention can be employed to treat subjects therapeutically or prophylactically who have or can be subject to an inflammatory condition.

In some embodiments, the invention provides a method of treating a condition in a mammal, wherein the condition is selected from the group consisting of allergic rhinitis, asthma, atopic dermatitis, chronic obstructive pulmonary disease (COPD), multiple sclerosis (MS), rheumatoid arthritis (RA), and diabetes, which comprises administering to a mammal in need thereof a therapeutically effective amount of the atropisomer 1(S) or a pharmaceutically acceptable salt thereof.

In some embodiments, the invention provides a method of treating a condition in a mammal, wherein the condition is selected from the group consisting of allergic rhinitis, asthma, atopic dermatitis, chronic obstructive pulmonary disease (COPD), multiple sclerosis (MS), rheumatoid arthritis (RA), and diabetes, which comprises administering to a mammal in need thereof a therapeutically effective amount of the atropisomer 1(S) or a pharmaceutically acceptable salt thereof, wherein the atropisomer is substantially free of its corresponding enantiomer.

In some embodiments, the invention provides a method of treating a condition in a mammal, wherein the condition is selected from the group consisting of allergic rhinitis, asthma, atopic dermatitis, chronic obstructive pulmonary disease (COPD), multiple sclerosis (MS), rheumatoid arthritis (RA), and diabetes, which comprises administering to a mammal in need thereof a therapeutically effective amount of the atropisomer 1(S) or a pharmaceutically acceptable salt thereof, wherein the atropisomer is substantially free of its corresponding enantiomer and has an enantiomeric excess of at least 90%.

In some embodiments, the invention provides a method of treating a condition in a mammal, wherein the condition is selected from the group consisting of allergic rhinitis, asthma, atopic dermatitis, chronic obstructive pulmonary disease (COPD), multiple sclerosis (MS), rheumatoid arthritis (RA), and diabetes, which comprises administering to a mammal in need thereof a therapeutically effective amount of the atropisomer 1(S) or a pharmaceutically acceptable salt thereof, wherein the atropisomer is substantially free of its corresponding enantiomer and has an enantiomeric excess of at least 98%.

In some embodiments, the invention provides a method of treating a condition in a mammal, wherein the condition is selected from the group consisting of allergic rhinitis, asthma, atopic dermatitis, chronic obstructive pulmonary disease (COPD), multiple sclerosis (MS), rheumatoid arthritis (RA), and diabetes, which comprises administering to a mammal in need thereof a therapeutically effective amount of the atropisomer 1(S) or a pharmaceutically acceptable salt thereof, wherein the atropisomer is substantially free of its corresponding enantiomer and has an enantiomeric excess of at least 99%.

In some embodiments, the invention provides a method of treating allergic rhinitis in a human, which comprises administering to a human in need thereof a therapeutically effective amount of optically active atropisomer 1(S) or a pharmaceutically acceptable salt thereof, wherein the atropisomer is substantially free of its corresponding enantiomer.

In some embodiments, the invention provides a method of treating asthma in a human, which comprises administering to a human in need thereof a therapeutically effective amount of optically active atropisomer 1(S) or a pharmaceutically acceptable salt thereof, wherein the atropisomer is substantially free of its corresponding enantiomer.

In some embodiments, the invention provides a method of treating chronic obstructive pulmonary disease (COPD) in a human, which comprises administering to a human in need thereof a therapeutically effective amount of optically active atropisomer 1(S) or a pharmaceutically acceptable salt thereof, wherein the atropisomer is substantially free of its corresponding enantiomer.

In some embodiments, the invention provides a method of treating multiple sclerosis in a human, which comprises administering to a human in need thereof a therapeutically effective amount of optically active atropisomer 1(S) or a pharmaceutically acceptable salt thereof, wherein the atropisomer is substantially free of its corresponding enantiomer.

In some embodiments, the invention provides a method of treating rheumatoid arthritis in a human, which comprises administering to a human in need thereof a therapeutically effective amount of optically active atropisomer 1(S) or a pharmaceutically acceptable salt thereof, wherein the atropisomer is substantially free of its corresponding enantiomer.

In some embodiments, the invention provides a method of treating diabetes in a human, which comprises administering to a human in need thereof a therapeutically effective amount of optically active atropisomer 1(S) or a pharmaceutically acceptable salt thereof, wherein the atropisomer is substantially free of its corresponding enantiomer.

In some embodiments, the invention provides a method of treating a condition in a human, wherein the condition is selected from the group consisting of allergic rhinitis, asthma, atopic dermatitis, chronic obstructive pulmonary disease (COPD), multiple sclerosis (MS), rheumatoid arthritis (RA), and diabetes, which comprises administering to a human in need thereof a therapeutically effective amount of an optically active atropisomer having the formula

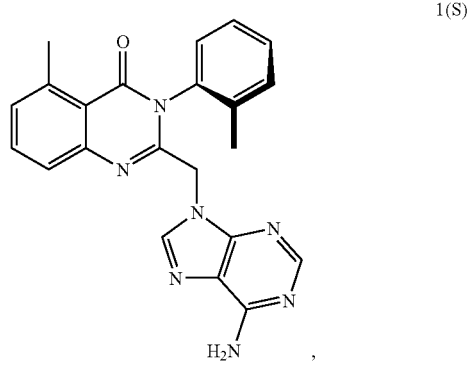

1(S)

or a pharmaceutically acceptable salt thereof.

Examples of inflammatory conditions include but are not limited to arthritic diseases such as rheumatoid arthritis (RA), osteoarthritis (OA), gouty arthritis, spondylitis, and reactive arthritis; Behçet's syndrome; sepsis; septic shock; endotoxic shock; gram negative sepsis; gram positive sepsis; toxic shock syndrome; multiple organ injury syndrome secondary to septicemia, trauma, or hemorrhage; ophthalmic disorders including but not limited to allergic conjunctivitis, vernal conjunctivitis, uveitis, and thyroid-associated opthalmopathy; eosinophilic granuloma; pulmonary or respiratory conditions including but not limited to asthma, chronic bronchitis, allergic rhinitis, adult respiratory distress syndrome (ARDS), severe acute respiratory syndrome (SARS), chronic pulmonary inflammatory diseases (e.g., chronic obstructive pulmonary disease), silicosis, pulmonary sarcoidosis, pleurisy, alveolitis, vasculitis, pneumonia, bronchiectasis, hereditary emphysema, and pulmonary oxygen toxicity; ischemic-reperfusion injury, e.g., of the myocardium, brain, or extremities; fibrosis including but not limited to cystic fibrosis; keloid formation or scar tissue formation; atherosclerosis; autoimmune diseases including but not limited to systemic lupus erythematosus (SLE), lupus nephritis, autoimmune thyroiditis, multiple sclerosis, some forms of diabetes, and Reynaud's syndrome; tissue or organ transplant rejection disorders including but not limited to graft versus host disease (GVHD) and allograft rejection; chronic or acute glomerulonephritis; inflammatory bowel diseases including but not limited to Crohn's disease, ulcerative colitis and necrotizing enterocolitis; inflammatory dermatitis including but not limited to contact dermatitis, atopic dermatitis, psoriasis, and urticaria; fever and myalgias due to infection; central or peripheral nervous system inflammatory conditions including but not limited to meningitis (e.g., acute purulent meningitis), encephalitis, and brain or spinal cord injury due to minor trauma; Sjögren's syndrome; diseases involving leukocyte diapedesis; alcoholic hepatitis; bacterial pneumonia; community acquired pneumonia (CAP); *Pneumocystis carinii* pneumonia (PCP); antigen-antibody complex mediated diseases; hypovolemic shock; Type 1 diabetes mellitus; acute and delayed hypersensitivity; disease states due to leukocyte dyscrasia and metastasis; thermal injury; granulocyte transfusion associated syndromes; cytokine-induced toxicity; stroke; pancreatitis; myocardial infarction, respiratory syncytial virus (RSV) infection; and spinal cord injury.

In some embodiments, the condition is selected from the group consisting of allergic rhinitis, asthma, atopic dermatitis, chronic obstructive pulmonary disease (COPD), multiple sclerosis (MS), rheumatoid arthritis (RA), and diabetes. In specific embodiments, diabetes is type I diabetes or type II diabetes.

In another aspect, the invention provides a method of treating a condition in a mammal, wherein the condition is cancer, which comprises administering to a mammal in need thereof a therapeutically effective amount of a compound described herein. In some embodiments, the cancer is a hematological malignancy. In a particular embodiment, the hematological malignancy is leukemia, lymphoma, or multiple myeloma. In other embodiments, the cancer is a solid tumor.

In some embodiments, lymphoma is a mature (peripheral) B-cell neoplasm. In specific embodiments, the mature B-cell neoplasm is selected from the group consisting of B-cell chronic lymphocytic leukemia/small lymphocytic lymphoma; B-cell prolymphocytic leukemia; Lymphoplasmacytic lymphoma; Marginal zone lymphoma, such as Splenic marginal zone B-cell lymphoma (+/− villous lymphocytes), Nodal marginal zone lymphoma (+/− monocytoid B-cells), and Extranodal marginal zone B-cell lymphoma of mucosa-associated lymphoid tissue (MALT) type; Hairy cell leukemia; Plasma cell myeloma/plasmacytoma; Follicular lymphoma, follicle center; Mantle cell lymphoma; Diffuse large cell B-cell lymphoma (including Mediastinal large B-cell lymphoma, Intravascular large B-cell lymphoma, and Primary effusion lymphoma); and Burkitt's lymphoma/Burkitt's cell leukemia.

In some embodiments, lymphoma is selected from the group consisting of multiple myeloma (MM) and non-Hodgkin's lymphoma (NHL), mantle cell lymphoma (MCL), follicular lymphoma, Waldenstrom's macroglobulinemia (WM) or B-cell lymphoma and diffuse large B-cell lymphoma (DLBCL).

In a further particular embodiment, leukemia is selected from the group consisting of acute lymphocytic leukemia (ALL), acute myeloid leukemia (AML), chronic lymphocytic leukemia (CLL), and small lymphocytic lymphoma (SLL). Acute lymphocytic leukemia is also known as acute lymphoblastic leukemia and may be used interchangeably herein.

Both terms describe a type of cancer that starts from the white blood cells, lymphocytes, in the bone marrow.

In specific embodiments, the hematological malignancy is selected from the group consisting of acute lymphocytic leukemia (ALL), acute myeloid leukemia (AML), chronic lymphocytic leukemia (CLL), multiple myeloma (MM), and non-Hodgkin lymphoma (NHL). In certain embodiments, the non-Hodgkin lymphoma is selected from the group consisting of large diffuse B-cell lymphoma (LDBCL), mantle cell lymphoma (MCL), Waldenstrom's macroglobulinemia (WM) and lymphoplasmacytic lymphoma.

In some embodiments, the invention provides a method of treating a hematological malignancy in a mammal, which comprises administering to a mammal in need thereof a therapeutically effective amount of optically active atropisomer 1(S) or a pharmaceutically acceptable salt thereof.

In further preferred embodiments, the invention provides a method of treating a condition in a mammal, wherein the condition is selected from the group consisting of acute lymphocytic leukemia (ALL), acute myeloid leukemia (AML), chronic lymphocytic leukemia (CLL), multiple myeloma (MM), and non-Hodgkin lymphoma (NHL), which comprises administering to a mammal in need thereof a therapeutically effective amount of optically active atropisomer 1(S) or a pharmaceutically acceptable salt thereof.

In some embodiments, the invention provides a method of treating cancer in a human, wherein the cancer is leukemia, lymphoma, or multiple myeloma, which comprises administering to a human in need thereof a therapeutically effective amount of an optically active atropisomer having the formula

1(S)

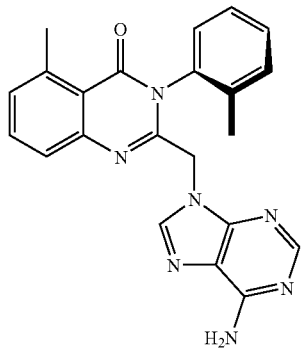

or a pharmaceutically acceptable salt thereof.

In some embodiments, the invention provides a method of treating a condition in a mammal, wherein the cancer is a solid tumor, which comprises administering to a mammal in need thereof a therapeutically effective amount of the optically active atropisomer 1(S) or a pharmaceutically acceptable salt thereof.

In specific embodiments, the cancer is breast, lung, colon, or prostate cancer. In certain embodiments, the invention provides methods to treat a solid tumor that is associated with abnormal or undesirable cellular signaling activity mediated by PI3Kβ. In certain embodiments, a solid tumor is selected from the group consisting of pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma.

In specific embodiments, the cancer is breast, ovarian, lung, colon, or prostate cancer.

In preferred embodiments, the mammal is a human.

In another aspect, the invention provides an optically active atropisomer obtained by chiral chromatographic separation of a racemic mixture of formula 1

(1)

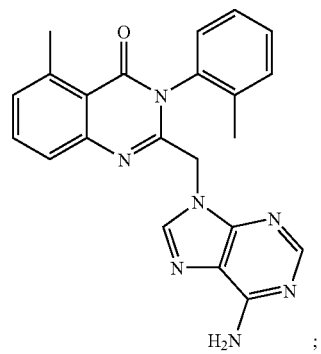

or a pharmaceutically acceptable salt or solvate thereof; wherein the mixture of formula 1 is separated using a normal phase chiral column, and two peaks, A and B, are resolved, wherein peak A and peak B represent the atropisomers, 1(S) and 1(R), respectively,

1(S)

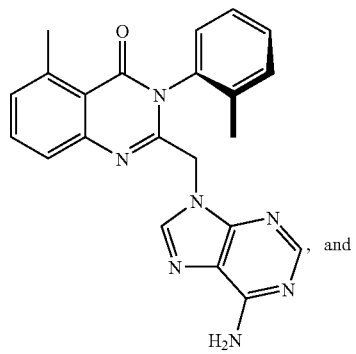

, and

1(R)

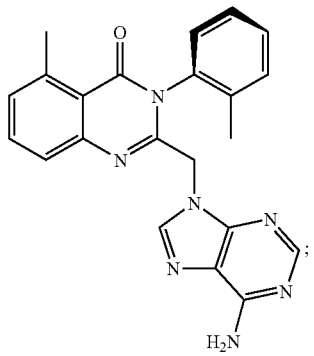

;

wherein the predominant isomer in the optically active atropisomer obtained is the first isomer to elute from the column In certain embodiments, the optically active atropisomer obtained consists predominantly of the compound of formula 1(S) substantially free of the compound of formula 1(R). In another embodiment, the optically active atropisomer obtained consists predominantly of the compound of formula 1(R) substantially free of the compound of formula 1(S).

In yet another aspect, the invention provides an optically active atropisomer obtained by chiral chromatographic separation of a racemic mixture of formula 1

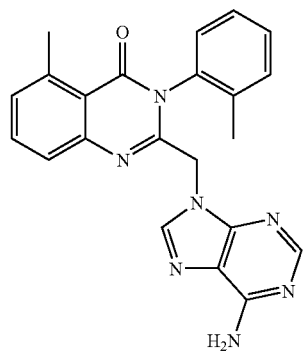

(1)

or a pharmaceutically acceptable salt or solvate thereof; wherein the racemic mixture of formula 1 is separated using a normal phase chiral column, and two peaks, A and B, are resolved, wherein peak A and peak B represent the atropisomers, 1(S) and 1(R), respectively,

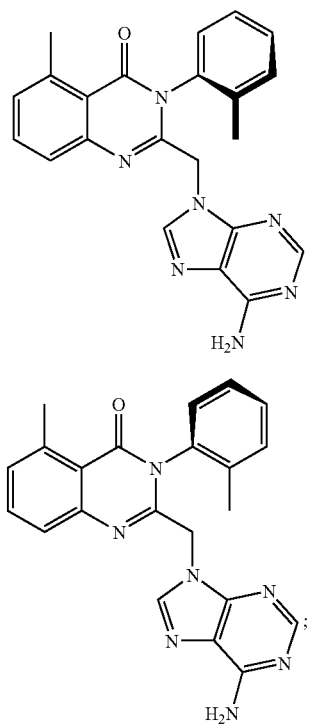

1(S)

1(R)

and
wherein the optically active atropisomer obtained consists predominantly of the second isomer to elute from the column In specific embodiments, the optically active atropisomer obtained consists predominantly of the compound of formula 1(S) substantially free of the compound of formula 1(R). In certain embodiments, the predominant optically active atropisomer obtained consists predominantly of the compound of formula 1(R) substantially free of the compound of formula 1(S).

In another aspect, the invention provides an optically active atropisomer obtained by separation of a racemic mixture of formula 1

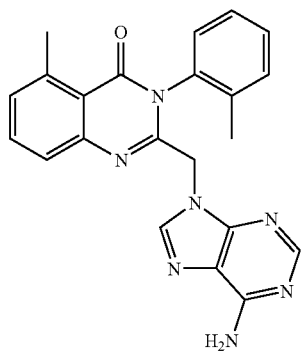

(1)

or a pharmaceutically acceptable salt or solvate thereof; wherein the optically active atropisomer is characterized by a shorter retention time on a normal phase chiral column when compared to its enantiomer. In some embodiments, the optically active atropisomer obtained consists predominantly of the compound of formula 1(S) substantially free of the compound of formula 1(R). In other embodiments, the optically active atropisomer obtained is the slower eluting isomer (longer retention time), and consists mostly of compound of formula 1(R) substantially free of the compound of formula 1(S).

In another aspect, the invention provides an optically active atropisomer obtained by separation of a racemic mixture of formula 1

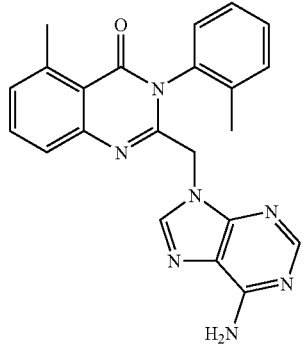

(1)

or a pharmaceutically acceptable salt or solvate thereof; wherein the optically active atropisomer is characterized by a longer retention time on a normal phase chiral column when compared to its enantiomer. In some embodiments, the predominant optically active atropisomer obtained is the compound of formula 1(S) substantially free of the compound of formula 1(R). In other embodiments, the optically active atropisomer obtained is the faster eluting isomer (shorter retention time), and consists mostly of the compound of formula 1(R) substantially free of the compound of formula 1(S).

In one embodiment, the compound of the invention is separated using a chiral chromatographic column. In certain embodiments, the chiral column has a normal phase. In alternative embodiments, the chiral column has a reverse phase.

The atropisomers of formula 1 were separated by normal phase HPLC methods resulting in two resolved peaks. See Example 2 and FIG. 2A for column and solvent conditions. The peak to elute first at 7.4 minutes has been labeled 1(S) and the second peak to elute at 12.3 minutes has been labeled 1(R). The absolute configuration of each isolated compound has been elucidated from x-ray crystallographic data. The first peak to elute has been assigned the S configuration, shown as compound 1(S), and the second peak to elute has been assigned the R configuration, shown as compound 1(R). The elution order of the peaks is reversed when a reverse phase column is used, as described in Example 2.

The in vitro activity of 1 and atropisomers, 1(S) and 1(R), have similar profiles in various isoforms of p110 inhibition as shown in FIGS. 5A and 5B. All three compounds exhibit selective p110δ inhibition in either biochemical (FIG. 5A) or cell-based assays (FIG. 5B). Although their in vitro potency appears to be similar, there are surprising in vivo differences observed between 1(S) and 1(R) as discovered in pharmacokinetic studies, mainly relating to the increased exposure of 1(S) and decreased exposure of 1(R) in the subject.

In order to perform the pharmacokinetic studies, compound I was radiolabeled using $^{14}C$ at the ortho-methyl group of the phenyl at position 3 of the quinazolinone ring. Radiolabeled 1

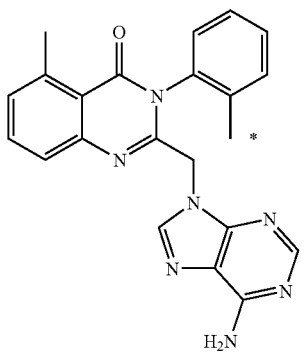

*denotes $^{14}C$ label

The tagged racemic mixture or separated atropisomers were administered to rats, dogs, and human subjects through oral and i.v. routes. The compounds were dissolved in PEG 100 such that any difference in dissolution rates would not play a role in the pharmacokinetic profile of the compounds. Modest solubility differences between 1(S) and 1(R) were observed in a variety of aqueous solutions as summarized in FIG. 4. After administration of the compound, blood plasma of the subjects were sampled over time and evaluated by analytical HPLC methods developed to identify and measure concentrations of compound 1(S) or 1(R) present in the sample. It was observed that the most abundant isomer measured in the plasma is compound 1(S), which accounts for 70-80% of exposure to the subject.

Figure 6:
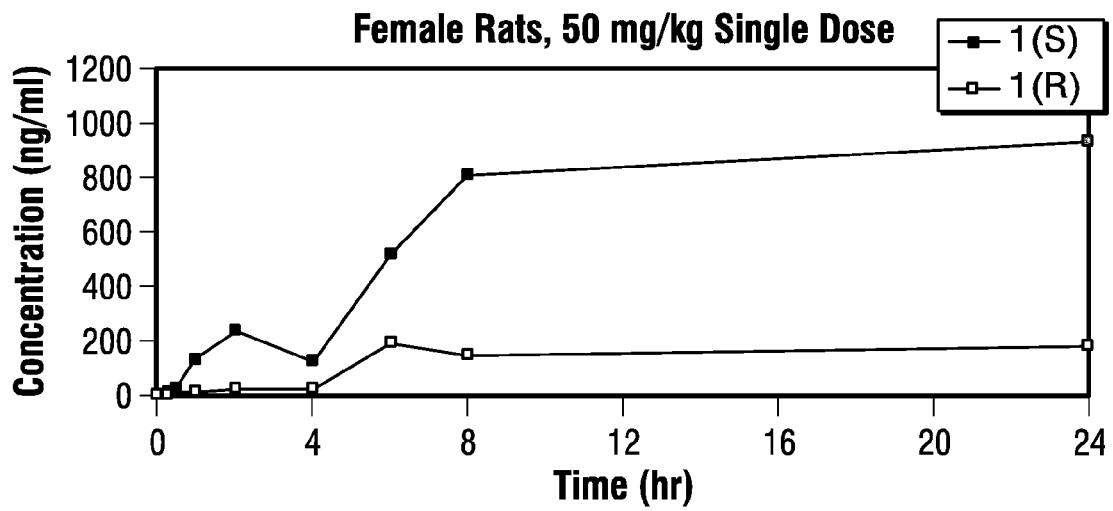
FIG. 6 shows the plasma concentration of atropisomers 1(S) and 1(R) in rats after oral dosing with racemic compound 1.

FIG. 6 shows the blood plasma concentration of 1(S) and 1(R) over 24 hours after a single 50 mg/kg dose of racemic 1 was orally administered to female rats. Four hours after dosing, the concentration of 1(S) steadily increases in the blood and 8 hours after dosing the average concentration of 1(R) is approximately one-fourth the concentration of 1(R). This demonstrates an in vivo difference in exposure between 1(S) and 1(R) when orally administered to rats, wherein the subject has increased exposure to 1(S) than 1(R).

Figure 7:
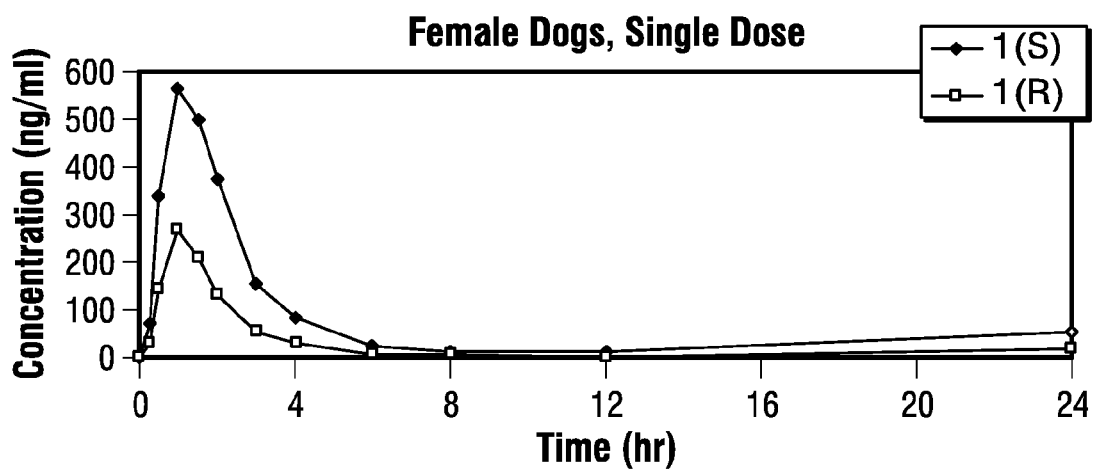
FIG. 7 shows the plasma concentration of atropisomers 1(S) and 1(R) in dogs after oral dosing with racemic compound 1.

FIG. 7 shows the blood plasma concentration of 1(S) and 1(R) over 24 hours after a single 50 mg/kg dose of racemic 1 was orally administered to female dogs. In approximately 1 hour after dosing the maximum concentration of 1(S) and 1(R) is reached. At that point, the concentration of 1(R) is less than half the concentration of 1(S). This demonstrates an in vivo difference in exposure between 1(S) and 1(R) when orally administered to dogs, wherein the subject has increased exposure to 1(S) than 1(R). These large differences in pharmacokinetic behavior were not predictable.

Figure 8:
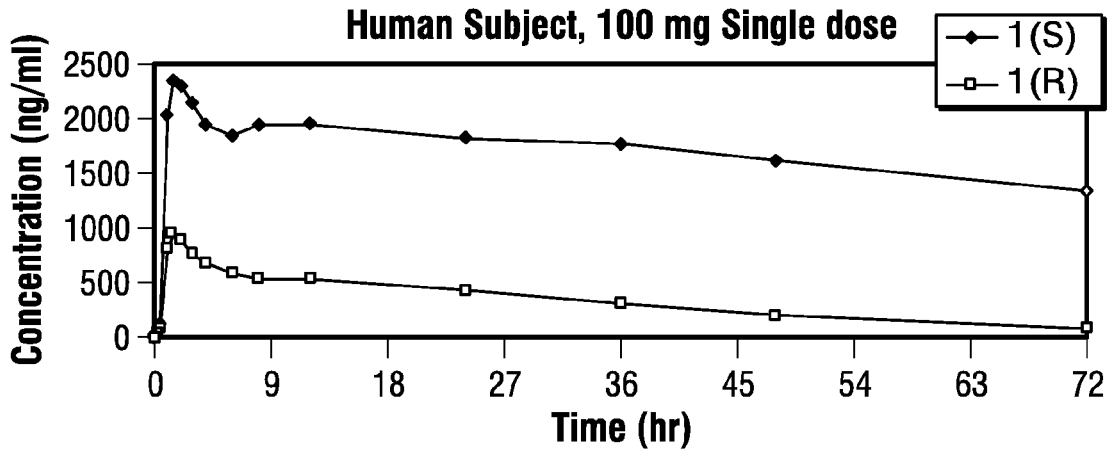
FIG. 8 shows the plasma concentration of atropisomers 1(S) and 1(R) in human subjects after oral dosing with racemic compound 1.

FIG. 8 shows the blood plasma concentration of 1(S) and 1(R) over 72 hours after a single 100 mg dose of racemic 1 was orally administered to human subjects. Within 2 hours, the maximum concentration of 1(S) and 1(R) is reached. At the maximum concentration point, the concentration of 1(R) is less than half the concentration of compound 1(S), which accounts for approximately 70% of the exposure in the animal. Although the concentrations of both compounds steadily decrease thereafter, at 72 hours post-dosing, the concentration of 1(S) is well over 10 times the concentration of 1(R). This demonstrates a surprising in vivo difference in exposure between 1(S) and 1(R) when orally administered to humans, wherein the subject has increased exposure to 1(S) relative to 1(R). Furthermore, it appears that the half-life of 1(S) is past the 72 hour time point. The half-life of 1(S) of several days in humans is greater than the half-life in dogs. The long half-life of 1(S) in humans allows for a lower dosage of administration. Reduced administrative dosages may also reduce, if any, undesired side-effects of the compound in the subject and provides an advantage over administration of the racemic mixture, or over 1(R).

Figure 9A:
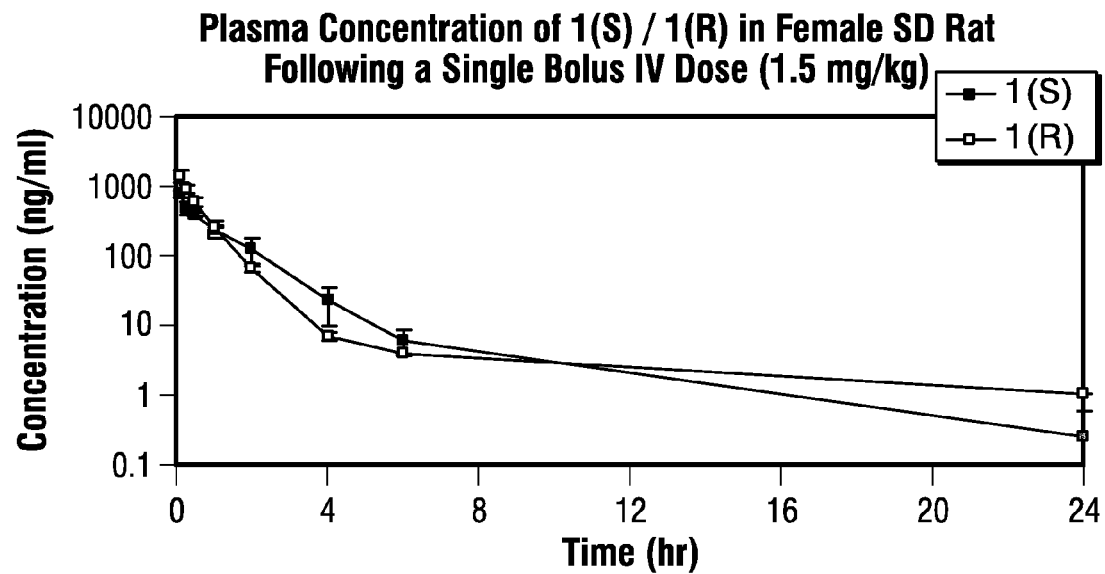
(FIG. 9A) or oral (FIG. 9B) dosing with compounds 1(S) or 1(R).
Figure 9B:
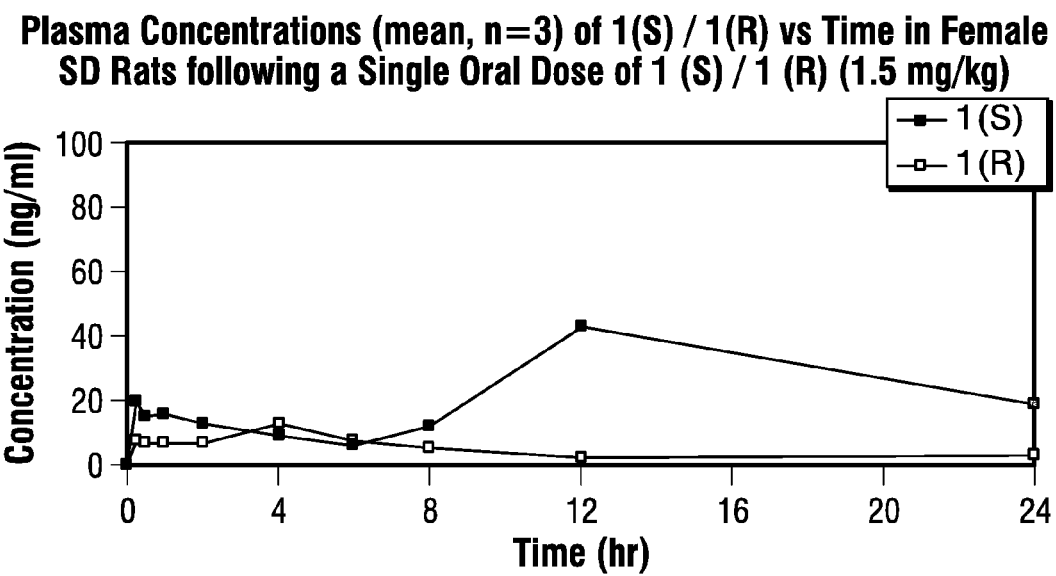
FIG. 9 shows a comparison of the plasma concentration of atropisomers 1(S) and 1(R) in rats subjects after either i.v.

FIG. 9 shows the blood plasma concentration of 1(S) and 1(R) over a period of 24 hours after a single dose of 1(S) or 1(R) (1.5 mg/kg) administered either via a single bolus i.v. dose (FIG. 9A) or an oral dose (FIG. 9B) to female rat subjects. In the intravenously administered study at the 4 hour time point, the exposure level of 1(R) is approximately one-fifth the concentration of 1(S). At 24 hours, the concentration of both compounds is very low and within experimental error. The concentration of 1(S) in blood plasma of rats that were orally administered the compounds was shown to greatly exceed the concentration of 1(R) at the 12 hour time point. This demonstrates an in vivo difference in exposure between 1(S) and 1(R) when either intravenously or orally administered to rats, wherein the subject has increased exposure to 1(S) relative to 1(R).

Table 1 summarizes the major pharmacokinetic parameters of 1(S) and 1(R) following a single bolus i.v. dose in female Sprague Dawley (SD) rats. Most notable is the half life of compound 1(R), which is about 2.8 times greater than the half life of either atropisomer 1(S) or the racemic mixture 1. Compound 1(R) has a volume of the terminal phase (Vz) value of 14,833 mL/kg, which is about 2.6 times greater than the Vz for either 1(S) or the racemic mixture.

TABLE 1

| Parameter | Compound 1(S) (1.5 mg/kg) | Compound 1(R) (1.5 mg/kg) | Compound 1 (3 mg/kg) |
|---|---|---|---|
| T½ (hr) | 2.5 ± 1.6 | 7.0 ± 1.1 | 2.5 ± 0.7 |
| CL (ml/hr/kg) | 1838 ± 503 | 1476 ± 85 | 1560 ± 180 |
| Vz (ml/kg) | 5773 ± 2740 | 14883 ± 2034 | 5397 ± 1568 |
| AUCall (ng/ml × hr) | 865 ± 212 | 1010 ± 55 | 1971 ± 243 |

Figure 10A:
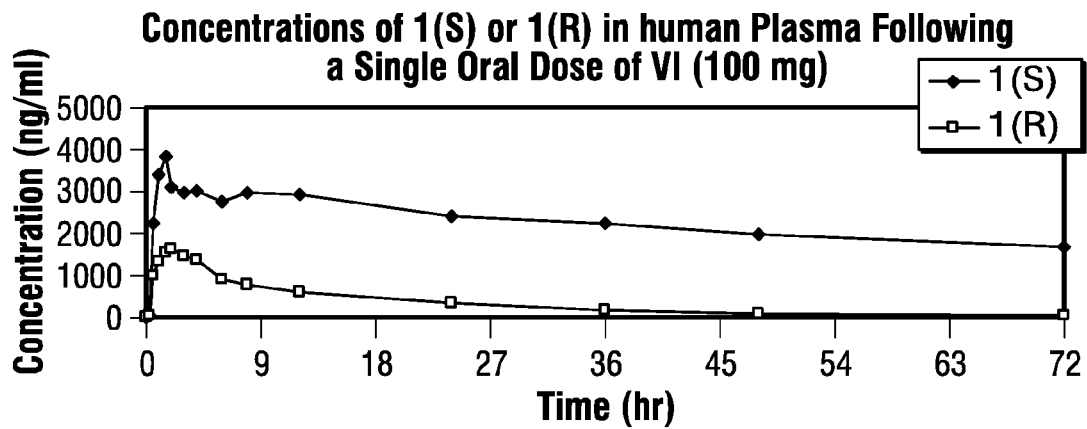
FIG. 10 shows a comparison of the plasma concentration of atropisomers 1(S) and 1(R) in human subjects after a single oral dose of 100 mg (FIG. 10A, 10B) or 10 mg (FIG. 10C, 10D) of 1(S) or 1(R).
Figure 10B:
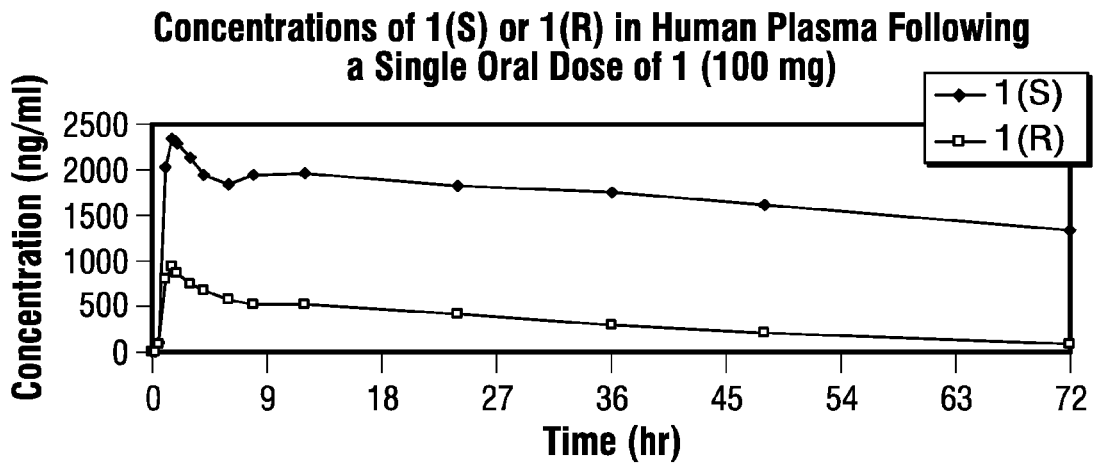

The in vivo differences between compounds 1(S) and 1(R) are examined in human subjects. FIGS. 10A and 10B show graphs of the blood plasma concentration of 1(S) and 1(R) plotted against a period of 72 hours after administration of a single, oral dose of 100 mg of the atropisomers. The maximum concentration of 1(S) is over 2 times as great as the maximum concentration for 1(R). Although the concentration of the compounds in the blood plasma decreases over the 72 hour period, the difference in concentration of the two compounds maintained, if not further broadened. This difference in compound concentration in the blood appears to broaden because compound 1(S) decreases more gradually over time whereas compound 1(R) appears to be removed from the blood relatively more quickly. At a dose of 10 mg, the maximum blood plasma concentration of compound 1(S) is still about double the maximum concentration of compound 1(R), see FIGS. 10C and 10D.

Figure 11:
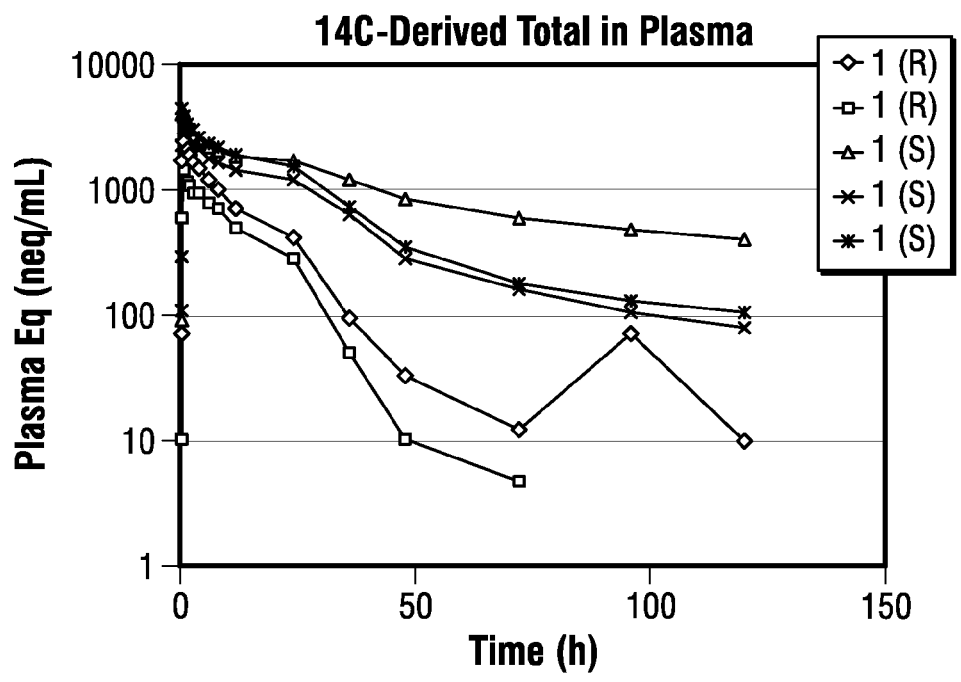
FIG. 11 shows a comparison of plasma concentration of radiolabeled $^{14}C$ atropisomers 1(S) and 1(R) in human subjects over 120 hours during daily administration of 25 mg of racemic compound 1.

FIG. 11 depicts the concentration of $^{14}C$ radiolabeled compound 1(S) and 1(R) in total blood plasma. Subjects were dosed with 25 mg of a racemic mixture of 1(S) and 1(R) each day for 7 days. On day 4, the dose was 'spiked' with 40 nCi of labeled 1(S) or labeled 1(R). (Total dosage was still 25 mg of the racemic mixture, since the amount of labeled material was less than 0.1 mg so it did not materially affect the dosage.) FIG. 11 shows the pharmacokinetic profile for total radiolabeled material starting when the spiked material was administered on day 4, and continuing for several days thereafter.

Both compounds in this test quickly reached their maximum concentration values and began a steady decline of concentration in the bloodstream. After day 1, the amount of 1(R), about 500 neq/mL, is about one-fourth the concentration of 1(S), which is about 2,000 neq/mL. The more rapid decline of 1(R) in the blood compared to 1(S) is further evident at 50 hours from dosing, wherein the blood plasma concentration of compound 1(S) is between 500 to 1,000 neq/mL compared to concentration of 1(R) which is about 10-50 neq/mL. The concentration of 1(R) decreases more rapidly than the concentration of 1(S) as shown by the sharper slope of the 1(R) curve compared to the more gradual and gentle slope of 1(S) in FIG. 11.

Table 2 summarizes the half-life, $C_{max}$ and AUC values in human subjects for compounds 1(S) and 1(R) based on the data in FIG. 11. At nearly 64 hours, compound 1(S) has a half-life 6 times as long as the half-life of 1(R), which has a half-life of under 11 hours. The $C_{max}$ value for 1(S) is twice as long as that of 1(R), and the AUC value for 1(S) is over 4 times as that of 1(R). These results demonstrate that compound 1(S) has an unexpected and very different pharmacokinetic profile compared to compound 1(R) in human subjects after oral dosing. Compound 1(S) has a significantly longer half-life, as well as increased Cmax and AUC values; thus compound 1(S) produces greater exposure in humans compared to 1(R). Compound 1(S) therefore offers unexpected advantages over either 1(R) or a racemic mixture, and treatment of a human with 1(S) can provide a higher, more stable plasma level of active drug than treatment with 1(R) or the racemate, and simultaneously reduces exposure of the subject to other materials or metabolites of 1(R).

TABLE 2

|  | T½ [h] | Cmax [neq/mL] | AUClast [neq*h/mL] |
| --- | --- | --- | --- |
| Compound 1 | 69.9 ± 26.6 | 2780 ± 1163 | 51,032 ± 22,383 |
| Compound 1(S) | 63.9 | 3930 | 90511 |
| Compound 1(R) | 10.6 | 1946 | 21676 |

Without being bound to theory, the lowered exposure of 1(R) compared to 1(S) suggests a difference in absorption and elimination between the two compounds. According to measurements using LC-MS (liquid chromatography-mass spectrometry), 1(R) is preferentially eliminated in urine. Also, 1(R) has been shown to have a larger volume of distribution, $V_z$, and has a greater rate of excretion and lower rate of absorption than 1(S). 1(R) may also be metabolized faster than 1(S). Regardless of the reasons, 1(R) is far less available in plasma (circulation) than 1(S) when administered orally, and 1(S) provides a far more stable exposure to the drug and lower exposure to metabolites.

Another possible explanation for the difference in exposure is that 1(R) is interconverted to 1(S) over time. Following administration of 1(R), it appears that approximately 14% of 1(R) is converted to 1(S) in blood plasma within 4 hours, while administration of 1(S) resulted in less than 1% of 1(S) converting to 1(R) over 4 hours. However, this small amount of conversion should only account for a fraction of the difference in exposure rates in vivo and other factors, such as selective elimination of 1(R), are likely to play the major role in the lowered exposure rate of 1(R).

Figure 12A:
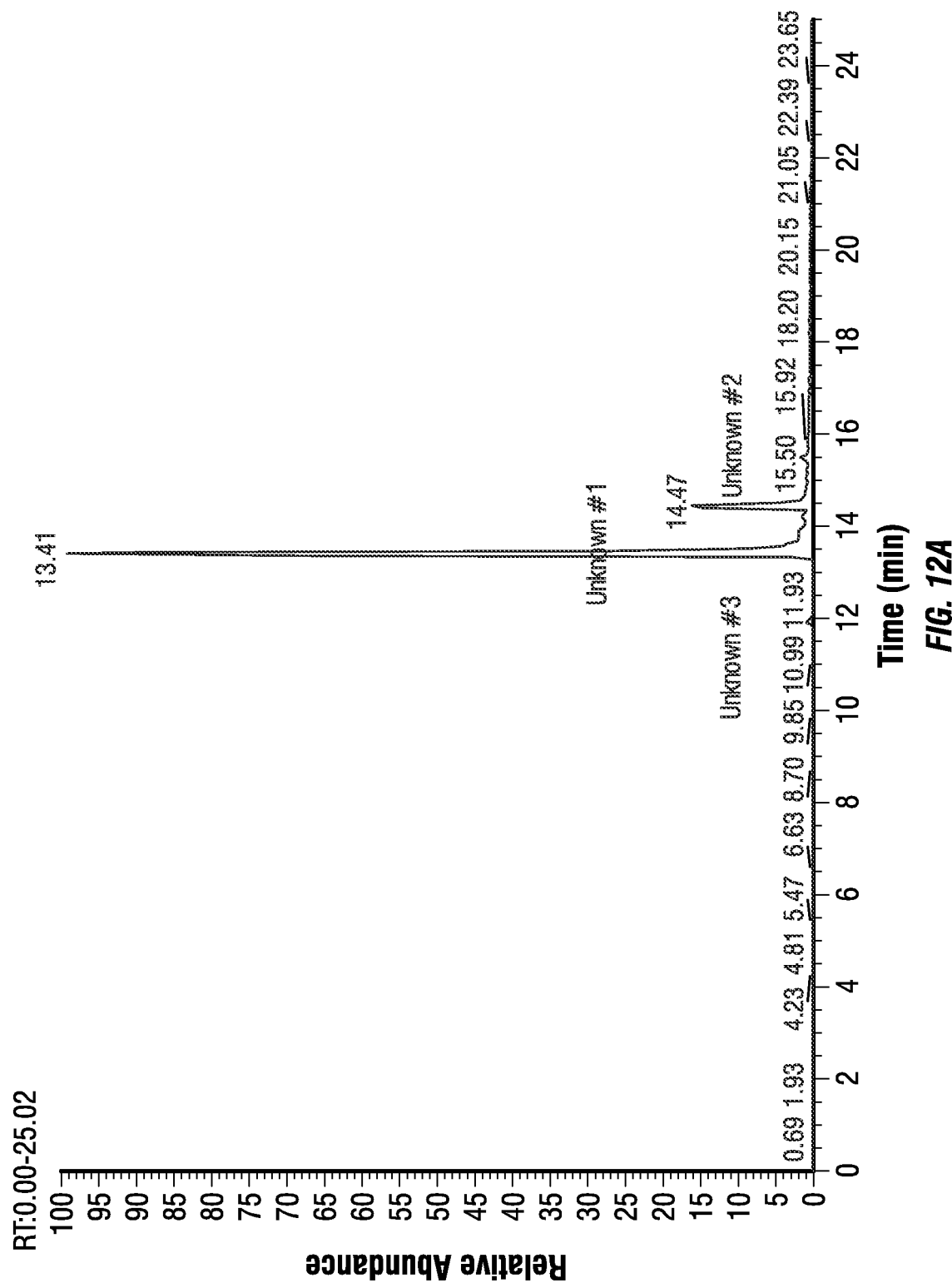
FIG. 12 shows LC-MS analytical traces of metabolites in rat urine after administration of atropisomer 1(S) (FIG. 12A) or atropisomer 1(R) (FIG. 12B).
Figure 12B:
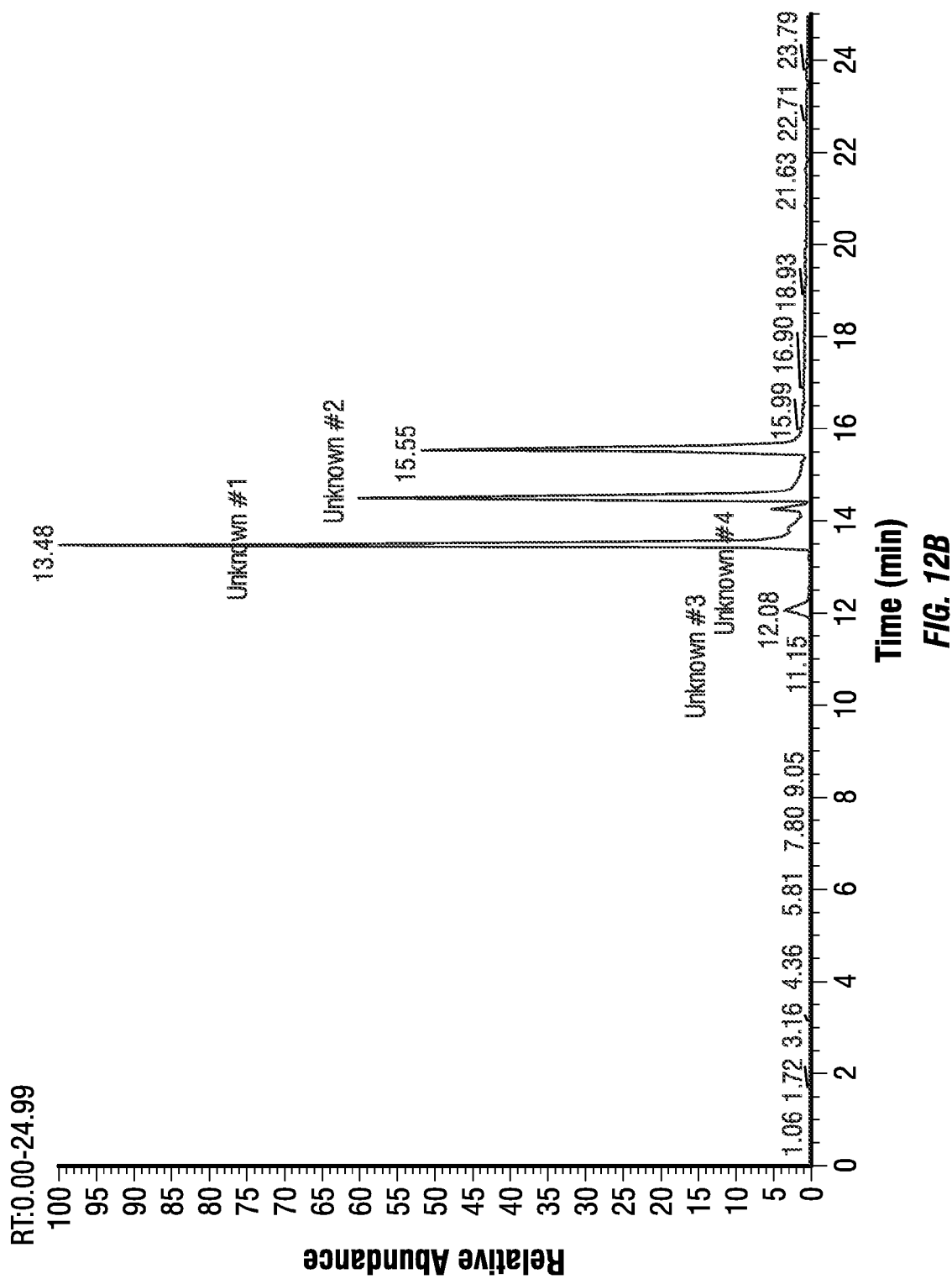

The in vivo differences between compounds 1(S) and 1(R) extend to the production of metabolic products. For example, after a single 50 mg/kg oral dose of either atropisomer 1(S) or 1(R), rat urine was sampled and analyzed for metabolites. FIGS. 12A and 12B show the LC-MS analysis results of the metabolites found in the urine. Rats which were exposed to 1(S) produced mainly one compound represented by a peak at 13.4 minutes and a second compound represented by a much smaller peak at 14.5 minutes. On the other hand, the analytical traces of urine from rats which were administered compound 1(R) are characterized by three main peaks at 13.5, 14.4, and 15.6 minutes, and a small peak at minute 12.1. This demonstrates that compound 1(R) is metabolized in vivo to produce more metabolic products compared to compound 1(S) and suggests that the two atropisomers are not metabolized by the body in exactly the same way.

FIGS. 13A-13D further illustrate the unexpected stability of 1(S) in vivo relative to 1(R). For these tests, either radiolabeled 1(S) or radiolabeled 1(R) was administered orally to a human subject. Samples of plasma from the subject were tested 1 hour and 72 hours after administration, and were analyzed for their radiolabeled content. The analysis used HPLC conditions that were known to separate 1(S) (eluting at about 21-22 minutes) from 1(R), so any interconversion between these species could be observed. It also resolves these two materials from the major metabolites formed from them in vivo.

Figure 13A:
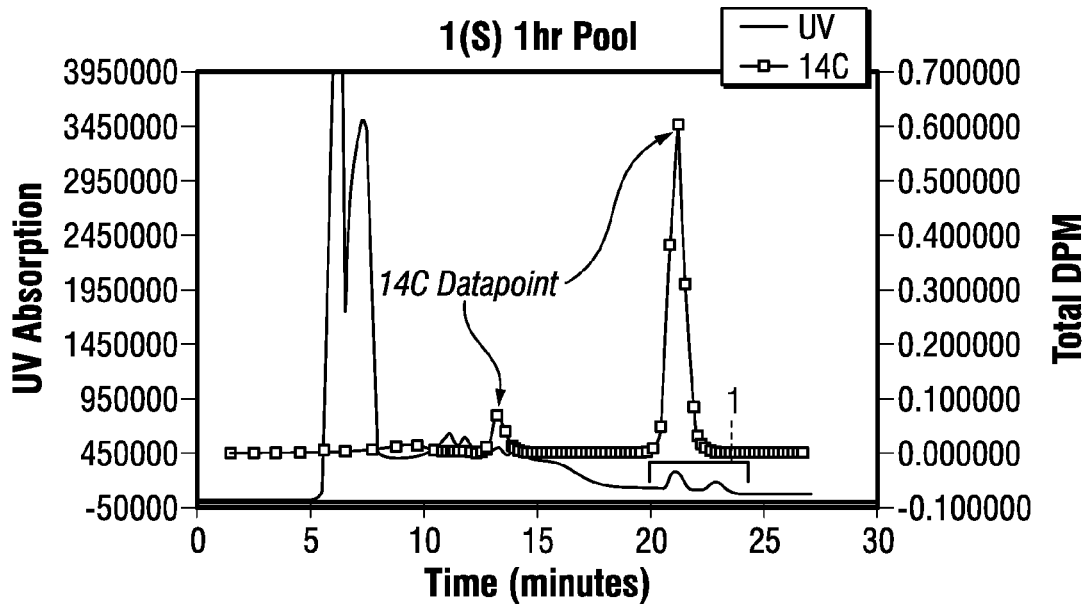
FIG. 13 shows analytical traces of metabolites in human plasma after administration of atropisomer 1(S) or atropisomer 1(R), tested 1 hour (FIG. 13A, 13B) or 72 hours (FIG. 13C, 13D) after oral administration.
Figure 13B:
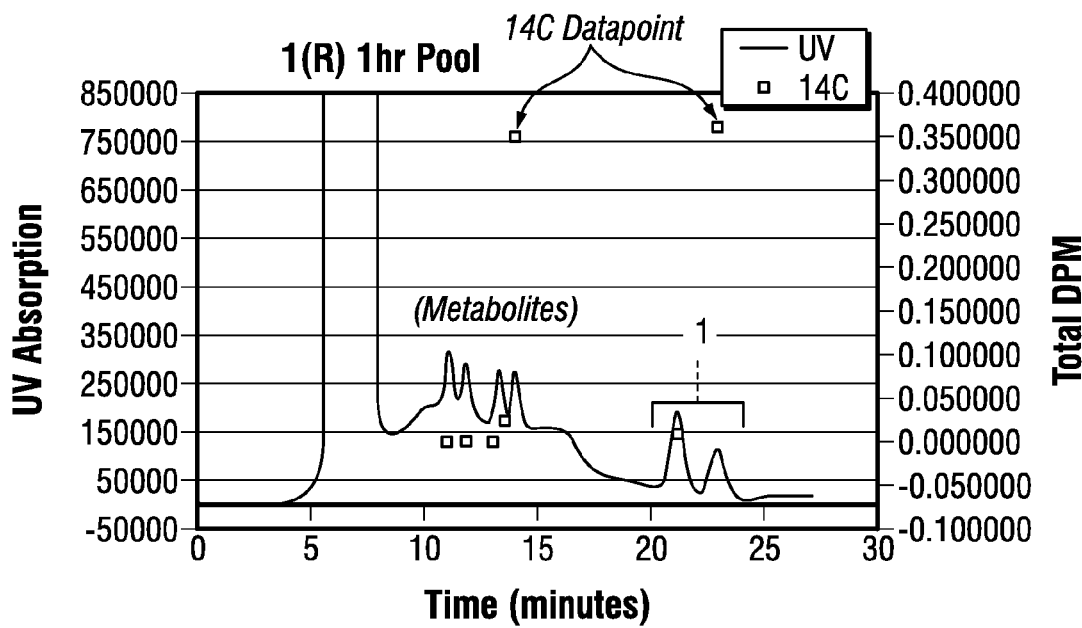
Figure 13C:
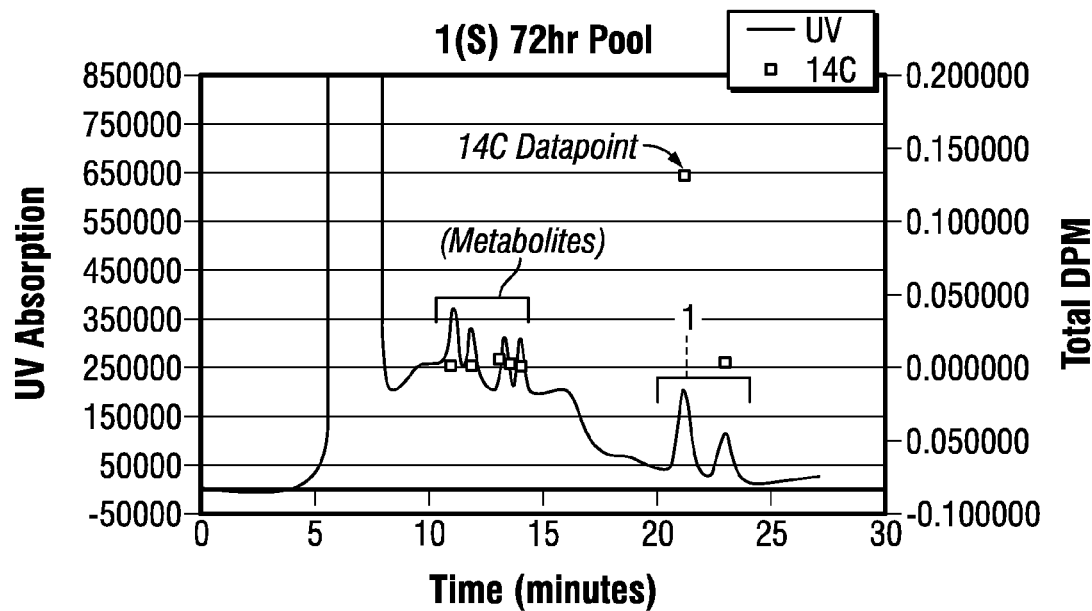
Figure 13D:
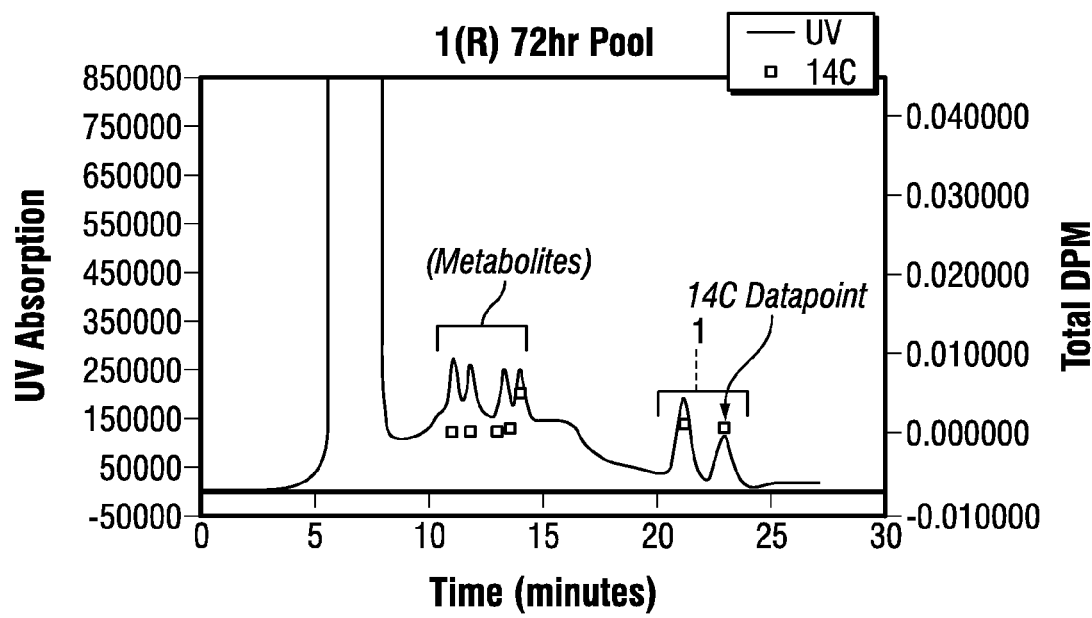

Radiolabeled compounds were separated from human blood plasma and analyzed by HPLC at 1 hour and 72 hours after administration of either radiolabeled compound as shown in FIG. 13A-13D. The UV trace in each spectrum is provided as a retention time standard to confirm the identity of the peaks, but the important data to observe is the C-14 radiolabel signal, which is represented by small squares at the retention time for 1(S), 1(R), and the known metabolites of these compounds. In FIG. 13A, there are two radiolabeled peaks observed, compound 1(S) (large peak at about 22 minutes) and a metabolite (small peak at about 14 minutes). In FIG. 13B, there are two dominant C-14 data points, 1(R) at 22 minutes, and a metabolite at 14 minutes. In this case, the metabolite level is nearly as large as the level of compound 1(R), even just one hour after administration of 1(R). Thus, compound 1(S) results in less metabolite formation than compound 1(R) in human plasma, and remains largely unmodified after 1 hr. At 72 hours, the amount of metabolites formed from 1(S) is still less than the amount of the parent compound 1(S), FIG. 13C. It appears that a small amount of 1(R) is present at this point in time, suggesting that some interconversion of 1(S) to 1(R) may occur in vivo. For 1(R) at 72 hours, primarily the metabolites are detected and very little of 1(R) is seen; indeed, it appears there may be more 1(S) than 1(R) present; again suggesting a small amount of interconversion may occur: see FIG. 13D.

Therefore, the abundance of metabolite after dosing with radiolabeled 1(R) suggests that compound 1(R) is metabolized by the human body relatively quickly. The much lower levels of metabolite in the plasma samples containing compound 1(S) suggests lower levels of metabolism, and the higher concentration of 1(S) 72 hours after administration shows this isomer provides longer exposure from a single dose.

Compound 1(S) offers the advantages of a longer half-life in vivo, reduced dosing amount and increased exposure in vivo. However, the pharmacokinetic characteristics of 1(R) also provide certain advantages for its use in some situations and subjects. The different pharmacokinetic profile of 1(R) provides a slower delivery of the 1(S), which has a longer half-life. For example, the interconversion of 1(R) to 1(S), as discussed previously, may provide a way to deliver a delayed exposure to compound 1(S), with a shortened exposure to high plasma concentration of active drug due to the short half-life of 1(R). Thus, the slower onset profile of compound 1(R) may be advantageous when a drug that has a greater area under the curve (AUC) profile is desired rather than a drug with a large $C_{max}$ value, or when relatively rapid elimination (short half-life) is desired. Accordingly, in certain embodiments, compounds, compositions, and methods of the invention comprise 1(R). Preferred embodiments, particularly for treatment of inflammatory conditions or hematological cancers, the compounds, compositions, and methods of the invention comprise 1(S).

Chiral resolution of enantiomers can be carried out by methods of high pressure liquid chromatography (HPLC), crystallization or the use of enzymes. Described herein are chiral resolution methods that employ HPLC to provide the compounds of the invention. For instance, mixtures of the atropisomers of formula 1 can be separated into compounds of the formulas 1(S) and 1(R). For purposes of discussion, resolved atropisomers of compound 1 that were isolated by normal phase chromatographic separation and eluted at time 8.7 min and 13.0 min as described in Example 3, will be referred to as atropisomers 1(S) and 1(R), respectively.

One of ordinary skill in the art will understand that many types of instruments, columns and eluents can be used to separate the individual atropisomers. Suitable HPLC instruments are configured according to methods well known to those of ordinary skill in the art. Such configuration invariably includes a pump, injection port and a detector.

Chromatographic columns may be characterized as 'normal phase' or 'reverse phase'. In general, normal phase columns have a polar stationary phase and reverse phase columns have a non-polar stationary phase. Suitable chiral columns can be purchased prepackaged or can be packed by one of ordinary skill in the art. Suitable chiral columns include chiral CHIRALPAK®IA, IB, AD-H, AS, AD-RH, AS-RH and IC columns as well as CHIRALCEL®OD-H, OB-H, OF, OG, OJ-RH and OJ which can be purchased from Chiral Technologies Inc., 730 Springdale Drive, PO Box 564, Exton, Pa. 19341. The packing composition for CHIRALPAK® IA columns is amylose tris(3,5-dimethylphenylcarbamate) immobilized on 5 µM silica-gel. One of ordinary skill in the art will appreciate that many other chiral columns, purchased from other vendors, would be adequate to separate the isomers of the invention. The packing material can also be purchased in different bead sizes. Suitable bead sizes for preparative separations are about 20 microns in diameter or less. Suitable bead sizes for analytical separation are about 10 microns in diameter or less.

One of ordinary skill in the art will understand that the appropriate mobile phase used in an HPLC method can be selected from various combinations and ratios of solvents. A suitable mobile phase is determined according to methods well known to those of ordinary skill in the art. The mobile phase may include organic solvents such as alkanes, alcohols, ethers, chlorinated solvents as water, and buffered water. Non-limiting examples of organic solvents include hexanes, n-hexane, methanol, ethanol, butanol, isobutanol, propanol, isopropanol (IPA), acetonitrile, N,N-dimethylformamide (DMF), tetrahydrofuran (THF), methyl-t-butyl ether, trichloromethane, dichlormethane, chloroform, 1,4-dioxane, toluene, acetone, methyl acetate and ethyl acetate. For basic or acidic samples, an additive may be incorporated into the mobile phase in order to optimize chiral separation. Primary amines, such as diethylamine (DEA), diisopropylamine, butyl amine, and triethylamine (TEA) may be used as bases. Non-limiting examples of acids include sulfuric acid, trifluoroacetic acid, hydrochloric acid, acetic acid, and formic acid. Other inorganic mobile phase additives may also be used, such as $KPF_6$, $NaClO_4$, $NaBF_4$, $NaH_2PO_4$. Non-limiting examples of mobile phase mixtures include 50:50:0.2 methanol/ethanol/DEA; 70:30:0.1 hexanes/ethanol/DEA; 70:30:0.1 hexanes/isopropanol/DEA; 40:60:0.06 hexanes/isopropanol/DEA; and 50:50, 60:40 or 70:30 water/acetonitrile. Non-limiting examples of mobile phases used for reverse phase screenings of basic compounds include 30:70 pH 9 borate/acetonitrile and 30:70 100 mM aqueous $KPF_6$/acetonitrile.

For a description of analytical or preparatory chromatographic methods, see Examples 2 and 3, respectively.

The relative efficacies of compounds as inhibitors of an enzyme activity (or other biological activity) can be established by determining the concentrations at which each compound inhibits the activity to a predefined extent, then comparing the results. Typically, the preferred determination is the concentration that inhibits 50% of the activity in a biochemical assay, i.e., the 50% inhibitory concentration or "IC50." IC50 determinations can be accomplished using conventional techniques known in the art. In general, an IC50 can be determined by measuring the activity of a given enzyme in the presence of a range of concentrations of the inhibitor under study. The experimentally obtained values of enzyme activity then are plotted against the inhibitor concentrations used. The concentration of the inhibitor that shows 50% enzyme activity (as compared to the activity in the absence of any inhibitor) is taken as the IC50 value. Analogously, other inhibitory concentrations can be defined through appropriate determinations of activity. For example, in some settings it can be desirable to establish a 90% inhibitory concentration, i.e., IC90.

"Treating" as used herein refers to preventing a disorder from occurring in an animal that can be predisposed to the disorder, but has not yet been diagnosed as having it; inhibiting the disorder, e.g., slowing or arresting its development; relieving the disorder, e.g., causing its regression or elimination; or ameliorating the disorder, i.e., reducing the severity of symptoms associated with the disorder. "Disorder" is intended to encompass medical disorders, diseases, conditions, syndromes, and the like, without limitation.

The methods of the invention embrace various modes of treating an animal subject, preferably a mammal, more preferably a primate, and still more preferably a human. Among the mammalian animals that can be treated are, for example, humans, companion animals (pets), including dogs and cats; farm animals, including cattle, horses, sheep, pigs, and goats; laboratory animals, including rats, mice, rabbits, guinea pigs, and nonhuman primates; and zoo specimens. Non-mammalian animals include, for example, birds, fish, reptiles, and amphibians. In general, any subject who would benefit from the compounds and compositions of the invention is appropriate for administration of the invention method.

Techniques for formulation and administration of pharmaceutical compositions can be found in *Remington's Pharmaceutical Sciences*, 18th Ed., Mack Publishing Co, Easton, Pa., 1990. The pharmaceutical compositions of the present invention can be manufactured using any conventional method, e.g., mixing, dissolving, granulating, dragee-making, levigating, emulsifying, encapsulating, entrapping, melt-spinning, spray-drying, or lyophilizing processes. An optimal pharmaceutical formulation can be determined by one of skill in the art depending on the route of administration and the desired dosage. Such formulations can influence the physical state, stability, rate of in vivo release, and rate of in vivo clearance of the administered agent. Depending on the condition being treated, these pharmaceutical compositions can be formulated and administered systemically or locally.

The pharmaceutical compositions are formulated to contain suitable pharmaceutically acceptable carriers, and optionally can comprise excipients and auxiliaries that facilitate processing of the active compounds into preparations that can be used pharmaceutically. The administration modality will generally determine the nature of the carrier. For example, formulations for parenteral administration can comprise aqueous solutions of the active compounds in water-soluble form. Carriers suitable for parenteral administration can be selected from among saline, buffered saline, dextrose, water, and other physiologically compatible solutions. Preferred carriers for parenteral administration are physiologically compatible buffers such as Hank's solution, Ringer's solution, or physiologically buffered saline. For tissue or cellular administration, penetrants appropriate to the particular barrier to be permeated are used in the formulation. Such penetrants are generally known in the art. For preparations comprising proteins, the formulation can include stabilizing materials, such as polyols (e.g., sucrose) and/or surfactants (e.g., nonionic surfactants), and the like.

Alternatively, formulations for parenteral use can comprise dispersions or suspensions of the active compounds prepared as appropriate oily injection suspensions. Suitable lipophilic solvents or vehicles include fatty oils, such as sesame oil, and synthetic fatty acid esters, such as ethyl oleate or triglycerides, or liposomes. Aqueous injection suspensions can contain substances that increase the viscosity of the suspension, such as sodium carboxymethylcellulose, sorbitol, or dextran. Optionally, the suspension also can contain suitable stabilizers or agents that increase the solubility of the compounds to allow for the preparation of highly concentrated solutions. Aqueous polymers that provide pH-sensitive solubilization and/or sustained release of the active agent also can be used as coatings or matrix structures, e.g., methacrylic polymers, such as the EUDRAGIT® series available from Röhm America Inc. (Piscataway, N.J.). Emulsions, e.g., oil-in-water and water-in-oil dispersions, also can be used, optionally stabilized by an emulsifying agent or dispersant (surface active materials; surfactants). Suspensions can contain suspending agents such as ethoxylated isostearyl alcohols, polyoxyethylene sorbitol and sorbitan esters, microcrystalline cellulose, aluminum metahydroxide, bentonite, agar-agar, gum tragacanth, and mixtures thereof.

Liposomes containing the active agent also can be employed for parenteral administration. Liposomes generally are derived from phospholipids or other lipid substances. The compositions in liposome form also can contain other ingredients, such as stabilizers, preservatives, excipients, and the like. Preferred lipids include phospholipids and phosphatidyl cholines (lecithins), both natural and synthetic. Methods of forming liposomes are known in the art. See, e.g., Prescott (Ed.), *Methods in Cell Biology*, Vol. XIV, p. 33, Academic Press, New York (1976).

Pharmaceutical compositions comprising the agent in dosages suitable for oral administration can be formulated using pharmaceutically acceptable carriers well known in the art. Preparations formulated for oral administration can be in the form of tablets, pills, capsules, cachets, dragees, lozenges, liquids, gels, syrups, slurries, elixirs, suspensions, or powders. To illustrate, pharmaceutical preparations for oral use can be obtained by combining the active compounds with a solid excipient, optionally grinding the resulting mixture, and processing the mixture of granules, after adding suitable auxiliaries if desired, to obtain tablets or dragee cores. Oral formulations can employ liquid carriers similar in type to those described for parenteral use, e.g., buffered aqueous solutions, suspensions, and the like.

Preferred oral formulations include tablets, dragees, and gelatin capsules. These preparations can contain one or excipients, which include, without limitation:

a) diluents, such as sugars, including lactose, dextrose, sucrose, mannitol, or sorbitol;
b) binders, such as magnesium aluminum silicate, starch from corn, wheat, rice, potato, etc.;
c) cellulose materials, such as methylcellulose, hydroxypropylmethyl cellulose, and sodium carboxymethylcellulose, polyvinylpyrrolidone, gums, such as gum arabic and gum tragacanth, and proteins, such as gelatin and collagen;
d) disintegrating or solubilizing agents such as cross-linked polyvinyl pyrrolidone, starches, agar, alginic acid or a salt thereof, such as sodium alginate, or effervescent compositions;
e) lubricants, such as silica, talc, stearic acid or its magnesium or calcium salt, and polyethylene glycol;
f) flavorants and sweeteners;
g) colorants or pigments, e.g., to identify the product or to characterize the quantity (dosage) of active compound; and
h) other ingredients, such as preservatives, stabilizers, swelling agents, emulsifying agents, solution promoters, salts for regulating osmotic pressure, and buffers.

Gelatin capsules include push-fit capsules made of gelatin, as well as soft, sealed capsules made of gelatin and a coating such as glycerol or sorbitol. Push-fit capsules can contain the active ingredient(s) mixed with fillers, binders, lubricants, and/or stabilizers, etc. In soft capsules, the active compounds can be dissolved or suspended in suitable fluids, such as fatty oils, liquid paraffin, or liquid polyethylene glycol with or without stabilizers. Dragee cores can be provided with suitable coatings such as concentrated sugar solutions, which also can contain gum arabic, talc, polyvinyl pyrrolidone, carbopol gel, polyethylene glycol, and/or titanium dioxide, lacquer solutions, and suitable organic solvents or solvent mixtures.

The pharmaceutical composition can be provided as a pharmaceutically acceptable salt of a compound of the invention. Salts are often more soluble in aqueous or other protonic solvents than the corresponding free acid or base forms. Pharmaceutically acceptable salts are well known in the art. Compounds that contain acidic moieties can form pharmaceutically acceptable salts with suitable cations. Suitable pharmaceutically acceptable cations include, for example, alkali metal (e.g., sodium or potassium) and alkaline earth (e.g., calcium or magnesium) cations.

Compounds of the invention that contain basic moieties can form pharmaceutically acceptable acid addition salts with suitable acids. For example, Berge, et al., *J Pharm Sci* (1977) 66:1, describe pharmaceutically acceptable salts in detail. The salts can be prepared in situ during the final isolation and purification of the compounds of the invention or separately by reacting a free base function with a suitable acid.

Representative acid addition salts include, but are not limited to, acetate, adipate, alginate, citrate, aspartate, benzoate, benzenesulfonate, bisulfate, butyrate, camphorate, camphorolsulfonate, cinnamate, digluconate, formate, glycerophosphate, hemisulfate, heptanoate, hexanoate, fumarate, hippurate, hydroxyacetate, hydrochloride, hydrobromide, hydroiodide, 2-hydroxyethanesulfonate (isothionate), lactate, maleate, malonate, mandelate, methanesulfonate or sulfate, nicotinate, 2-naphthalenesulfonate, oxalate, pamoate, pectinate, persulfate, 3-phenylpropionate, picrate, pivalate, propionate, pyruvate, succinate, tartrate, thiocyanate, phosphate or hydrogen phosphate, glutamate, bicarbonate, salicylate, p-toluenesulfonate, and undecanoate.

Examples of inorganic acids include, but are not limited to, hydrochloric acid, hydrobromic acid, sulfuric acid, nitric acid, and phosphoric acid.

Basic addition salts can be prepared in situ during the final isolation and purification of the compounds of the invention or separately by reacting a carboxylic acid-containing moiety with a suitable base such as the hydroxide, carbonate, or bicarbonate of a pharmaceutically acceptable metal cation, or with ammonia or organic primary, secondary, or tertiary amine. Pharmaceutically acceptable basic addition salts include, but are not limited to, cations based on alkali metals or alkaline earth metals such as lithium, sodium, potassium, calcium, magnesium, and aluminum salts and the like, and nontoxic quaternary ammonium and amine cations including ammonium, tetramethylammonium, tetraethylammonium, methylammonium, dimethylammonium, trimethylammonium, ethylammonium, diethylammonium, triethylammonium, and the like. Other representative organic amines useful for the formation of base addition salts include ethylenediamine, ethanolamine, diethanolamine, piperidine, piperazine, and the like.

Basic nitrogen-containing groups can be quaternized with such agents as lower alkyl halides such as methyl, ethyl, propyl, and butyl chlorides, bromides and iodides; dialkyl sulfates like dimethyl, diethyl, dibutyl, and diamyl sulfates; long chain alkyl halides such as decyl, lauryl, myristyl, and stearyl chlorides, bromides, and iodides; arylalkyl halides such as benzyl and phenethyl bromides; and others. Products having modified solubility or dispersibility are thereby obtained.

Solvates for the purposes of the invention refer to those forms of the compounds of the invention which in solid or liquid state form a complex through coordination with solvent molecules. Non-limiting examples of a solvent are water, acetone, methanol, ethanol and acetic acid.

The compounds of the invention may be prepared in the form of prodrugs, i.e., protected forms which release the compounds of the invention after administration to the subject. Typically, the protecting groups are hydrolyzed in body fluids such as in the bloodstream thus releasing the active compound or are oxidized or reduced in vivo to release the active compound. A discussion of prodrugs is found in Smith and Williams Introduction to the Principles of Drug Design, Smith, H.J.; Wright, 2nd ed., London (1988).

The formulation and route of administration chosen will be tailored to the individual subject, the nature of the condition to be treated in the subject, and generally, the judgment of the attending practitioner.

In some embodiments, the compounds of the invention are administered by injection most preferably by intravenous injection, but also by subcutaneous or intraperitoneal injection, and the like. Additional parenteral routes of administration include intramuscular and intraarticular injection. For intravenous or parenteral administration, the compounds are formulated in suitable liquid form with excipients as required. The compositions may contain liposomes or other suitable carriers. For injection intravenously, the solution is made isotonic using standard preparations such as Hank's solution.

Besides injection, other routes of administration may also be used. The compounds may be formulated into tablets, capsules, syrups, powders, or other suitable forms for administration orally. By using suitable excipients, these compounds may also be administered through the mucosa using suppositories or intranasal sprays. Transdermal administration can also be effected by using suitable penetrants and controlling the rate of release.

The compounds may be administered as a single dose, a dose over time, as in i.v. or transdermal administration, or in multiple dosages. Dosages may be higher when the compounds are administered orally or transdermally as compared to, for example, i.v. administration.

Suitable dosage ranges for the compounds of the invention vary according to these considerations, but in general, the compounds are administered in the range of about 0.1 µg/kg-5 mg/kg of body weight; preferably the range is about 1 µg/kg-300 µg/kg of body weight; more preferably about 10 µg/kg-100 µg/kg of body weight. For a typical 70-kg human subject, thus, the dosage range is from about 0.7 µg-350 mg; preferably about 700 µg-21 mg; most preferably about 700 µg-10 mg. In certain embodiments, the compound is administered in the range of 5-15 mg/kg of body weight. In certain embodiments, the compound is administered at a dose of less than 11 mg/kg of body weight. In certain embodiments, the compound is administered at a dose of 10 mg/kg of body weight. In certain embodiments, suitable dosage is an amount between 1-500 mg. In certain embodiments, suitable dosage is an amount between 1-250 mg. In certain embodiments, suitable dosage is an amount between 1-100 mg. In certain embodiments, suitable dosage is an amount between 1-50 mg. In certain embodiments, suitable dosage is an amount between 1-25 mg. In certain embodiments, suitable dosage is an amount selected from the group consisting of 10 mg, 17 mg, 50 mg, 75 mg, 100 mg, 125 mg, 200 mg, 250 mg, and 400 mg, recognizing that small departures (+/−<10%) are generally tolerated. In certain embodiments, the suitable dosage is administered orally.

Compositions comprising a compound of the invention formulated in a pharmaceutically acceptable carrier can be prepared, placed in an appropriate container, and labeled for treatment of an indicated condition. Accordingly, there also is contemplated an article of manufacture, such as a container comprising a dosage form of a compound of the invention and a label containing instructions for use of the compound. Kits also are contemplated. For example, a kit can comprise a dosage form of a pharmaceutical composition and a package insert containing instructions for use of the composition in treatment of a medical condition. In either case, conditions indicated on the label can include treatment of an inflammatory condition.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted.

The discussion of the general methods given herein is intended for illustrative purposes only. Other alternative methods and embodiments will be apparent to those of skill in the art upon review of this disclosure.

A group of items linked with the conjunction "or" should not be read as requiring mutual exclusivity among that group, but rather should also be read as "and/or" unless expressly stated otherwise. Although items, elements, or components of the invention may be described or claimed in the singular, the plural is contemplated to be within the scope thereof unless limitation to the singular is explicitly stated.

The following examples are offered to illustrate but not to limit the invention.

EXAMPLE 1

Preparation of 2-((6-amino-9H-purin-9-yl)methyl)-5-methyl-3-o-tolylquinazolin-4(3H)-one The synthetic scheme for the preparation of 2-((6-amino-9H-purin-9-yl)methyl)-5-methyl-3-o-tolylquinazolin-4(3H)-one, 1, is shown in FIG. 1. 2-amino-6-methylbenzoic acid, 1", is reacted with 2-chloroacetyl chloride to produce the 2-(-2-chloroacetamido)-6-methylbenzoic acid, 2". Reaction with o-toluidine and phosphoryl trichloride yields the cyclized intermediate, 3". Further reaction with diBOC-protected adenine give the BOC protected product, 4", which is deprotected resulting in 2-((6-amino-9H-purin-9-yl)methyl)-5-methyl-3-o-tolylquinazolin-4(3H)-one, 1.

The atropisomers of compound 1 may be resolved by high-pressure liquid chromatography (HPLC). Intermediate compounds 3" and 4" also contain atropisomers and resolution of either of these intermediates by HPLC can also be carried out prior to subsequent steps c and d, respectively.

EXAMPLE 2

Analytical HPLC Method Development for Separation of Atropisomers

This example describes the development of HPLC analytic methods for separating enantiomers of formula 1, 2-((6-amino-9H-purin-9-yl)methyl)-5-methyl-3-o-tolylquinazolin-4(3H)-one. In order to develop and optimize the separation of various atropisomers, a person having ordinary skill in the art can experiment with chromatographic parameters such as choice of column, mobile phase and flow rate. Methods for normal phase and reverse phase columns are described.

Normal phase. In this example, an enantiomeric mixture of compound 1 was initially screened across CHIRALPAK®IA, IB, AD-H, AS and IC columns as well as CHIRALCEL®OD-H and OJ and using 50:50:0.1 methanol/ethanol/DEA and 99.9:0.1 acetonitrile/DEA as polar organic mobile phases. A partial separation of atropisomers was observed on CHIRALPAK®AD-H using the mobile phase 50:50:0.1 methanol/ethanol/DEA. In order to determine if this partial separation could be improved, the column was eluted with ethanol/DEA. Complete separation was obtained using these conditions, with an alpha of 1.66 and a run time of approximately 20 minutes.

Figure 2A:
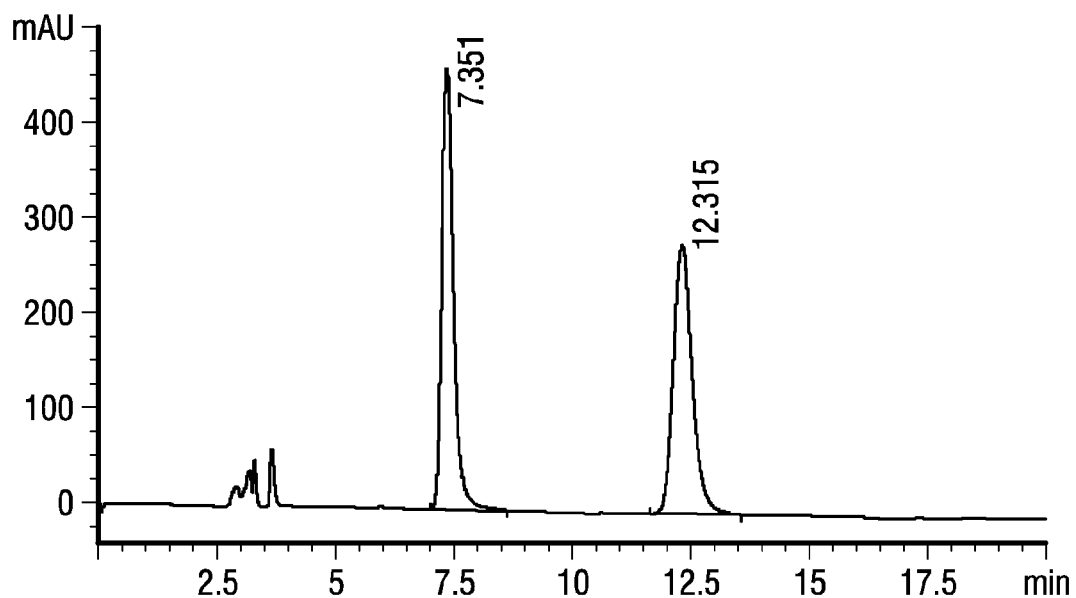
FIG. 2 shows HPLC traces of injected compound, 1, containing resolved atropisomers on normal phase (FIG. 2A) or reverse phase (FIG. 2B) chiral columns.

Screening was also done across the same set of columns, as well as CHIRALCEL®OB-H, OF, and OG using 70:30:0.1 hexanes/ethanol/DEA and 70:30:0.1 hexanes/isopropanol/DEA mobile phases. A promising separation appeared on the IA™ column with the 70:30:0.1 hexanes/isopropanol/DEA mobile phase; however, the run time of 28 minutes was a bit long. The run time was reduced to 15 minutes using a mobile phase of 40:60:0.06 hexanes/isopropanol/DEA. This separation was superior to the separation achieved on the AD-H column, using ethanol/DEA mobile phase. A chromatogram of atropisomers of compound 1 on the IA™ column is illustrated in FIG. 2a.

Thus, the final conditions to separate the enantiomeric mixture of compound 1 include using CHIRALPAK®IA™ column with dimensions of 250 mm L×4.6 mm ID. The sample was dissolved in ethanol and a mobile phase of 40:60:0.06 hexanes/isopropanol/diethylamine was used. Flow conditions were at a rate of 1.0 mL/min, at 25° C. and UV detection of the product was monitored at 215 nm. The run time was about 15 minutes. The two main peaks at 7.4 min and 12.3 min represent the first and second atropisomers of compound 1, 1(S) and 1(R), respectively.

Figure 2B:
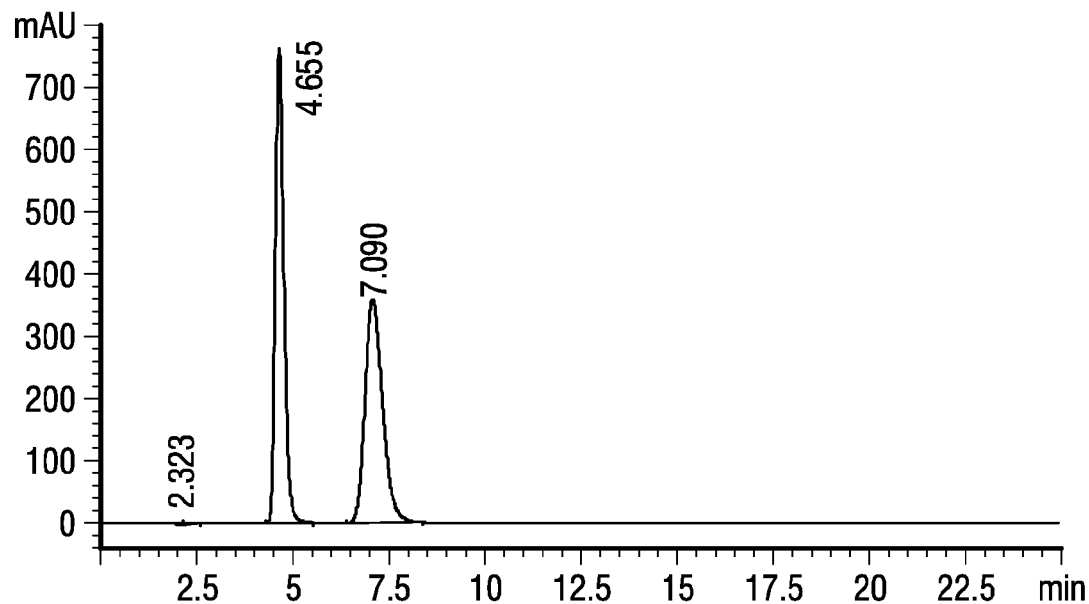

Reverse phase. A sample of an enantiomeric mixture of 2-((6-amino-9H-purin-9-yl)methyl)-5-methyl-3-o-tolylquinazolin-4(3H)-one, 1, was combined in acetonitrile and used for screening. The sample was screened with CHIRALPAK® AD-RH®, AS-RH®, IB™ IC™ and CHIRALCEL®OJ-RH® columns, eluted with 30:70 pH 9 borate/acetonitrile and 30:70 100 mM aqueous $KPF_6$/acetonitrile mobile phases. Partial separations were observed for the IC™ column with both mobile phases, and baseline separation was observed with both mobile phases using the OJ-RH® column. Efforts were made to improve the separation demonstrated on the OJ-RH® column. The column was eluted with 50:50, 60:40, and 70:30 water/acetonitrile. In these experiments, no buffer was added to the mobile phase in order to determine if such buffer was actually needed. It is apparent from the results that no buffer is needed for this separation, as all three of the water/acetonitrile mobile phases produced good separations on the OJ-RH® column. Of these conditions, the separation on the OJ-RH® column with 60:40 water/acetonitrile is recommended, although the separation with 50:50 water/acetonitrile acetonitrile was quite good, provided that there are no interfering peaks eluting close to the solvent front. A chromatogram of the separation of atropisomers on the OJ-RH® column using 60:40 water/acetonitrile is illustrated in FIG. 2b. The two main peaks at 4.7 min and 7.1 min represent the two atropisomers, of compound 1.

The enantiomeric mixture is fully resolved in both the normal phase and reverse phase methods (Normal phase: CHIRALPAK® IA, 250 mm L×4.6 mm ID, 40:60:0.06 hexanes/IPA/DEA, 1.0 mL/min, 25° C., 215 nm; Reverse phase: CHIRALCEL®OJ-RH, 150 mm L×4.6 mm ID, 61:40 water/acetonitrile, 0.8 mL/min, 25° C.; 230 nm). It is observed that the two peaks resolved in the normal phase method elute in reverse order in the reverse phase method. This was determined after the compound from the first peak, eluted at 7.4 minutes, on the normal phase was isolated and subjected to analysis on the reverse phase method. This isolated material eluted at a time corresponding to the second peak, 7.1 minutes, on the reverse phase method, FIG. 2b.

EXAMPLE 3

Preparatory HPLC Separation of Atropisomers and Absolute Stereochemical Configuration This example demonstrates the separation of the two atropisomers of compound 1 using HPLC.

Figure 3A:
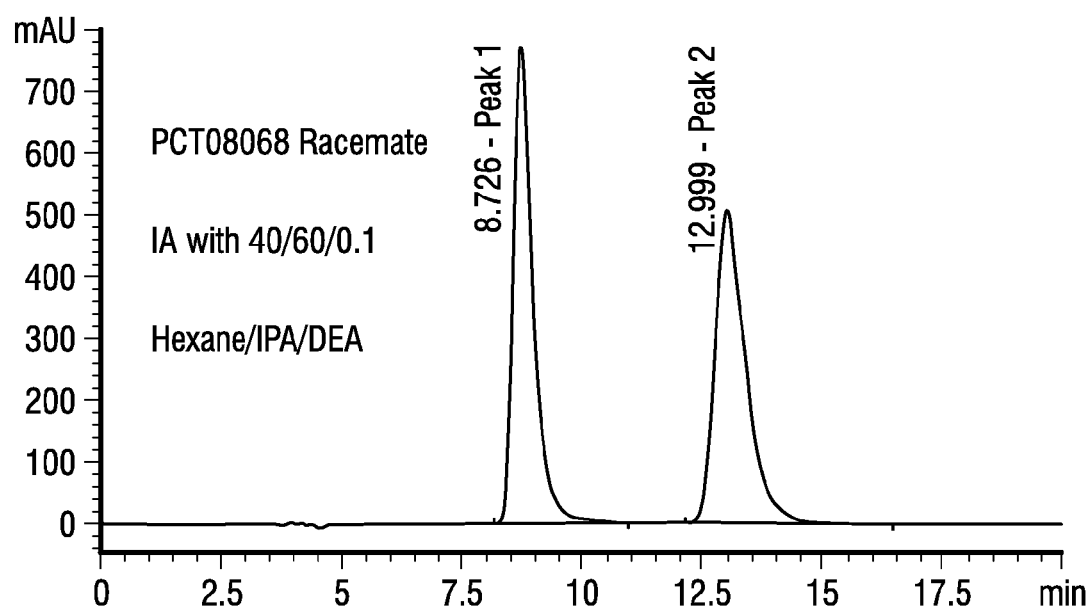
FIG. 3 shows HPLC traces of resolved injected compound, 1, prior to preparatory chromatographic separation (FIG. 3A), and isolated atropisomers peak 1 (FIG. 3B), 1(S), and peak 2 (FIG. 3C), 1(R), after separation using a normal phase column method.
Figure 3B:
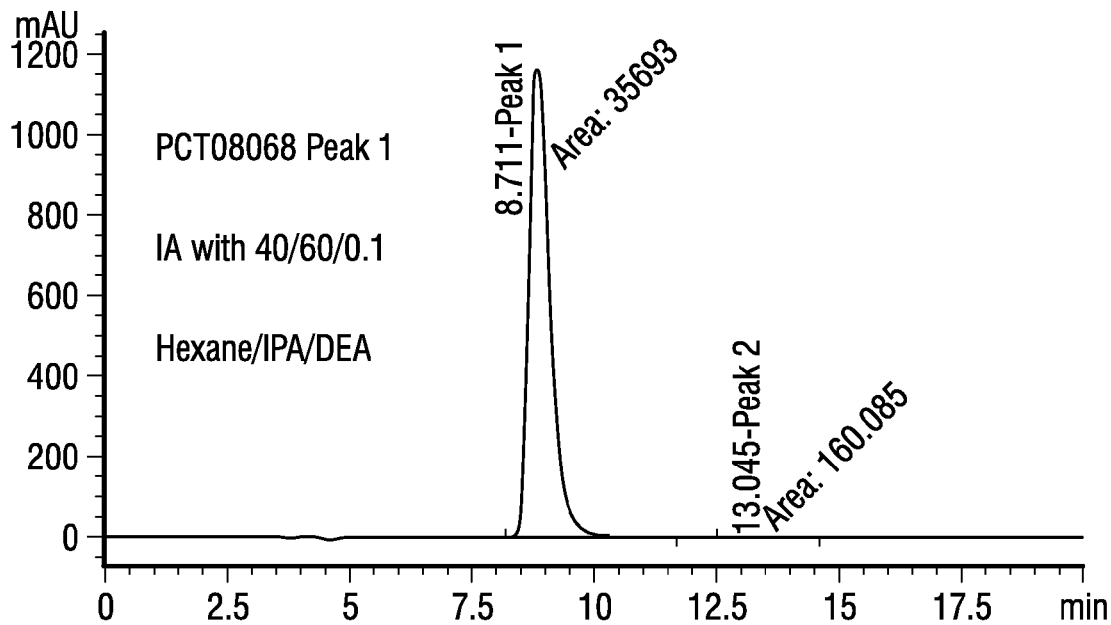
Figure 3C:
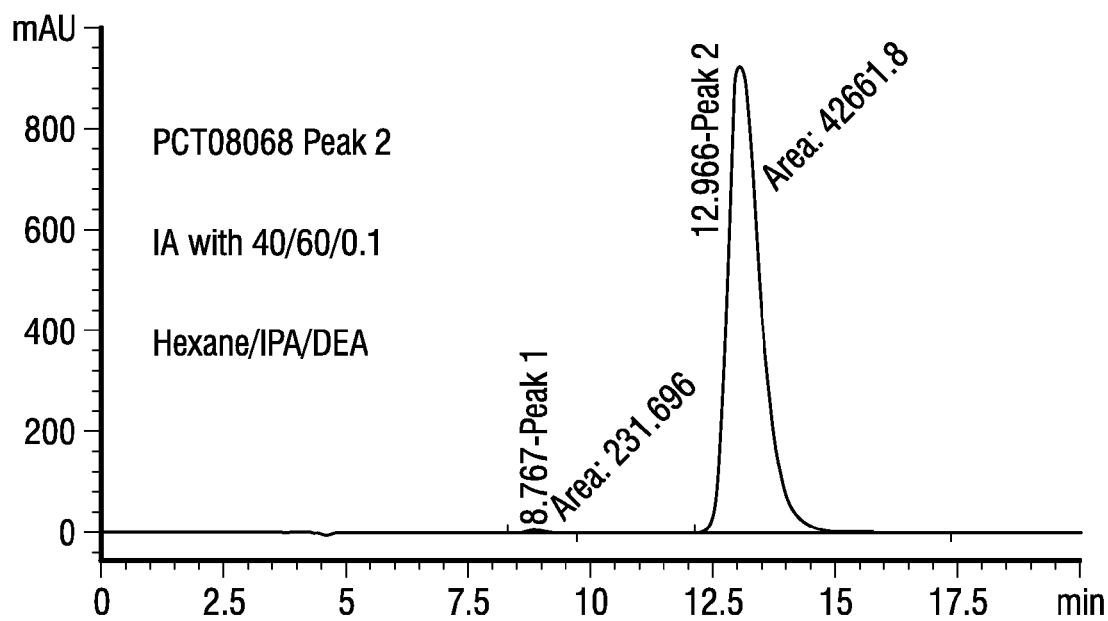

An analytical method was developed and a small sample of the enantiomeric mixture was dissolved in isopropanol at a concentration of 1.45 mg/mL and 5 µL injected into a normal phase column using the following conditions: CHIRAL-PAK® IA, 4.6 mm ID×250 mm L, 40/60/0.1 hexanes/IPA/DEA, 0.8 mL/min, 30° C. Two peaks are resolved at 8.7 min and 13.0 min (FIG. 3A). These analytical conditions and HPLC trace were used to identify the compositions of the separated products.

2.80 g of compound 1 was separated on a CHIRALPAK® IA preparative column using 40/60/0.1 hexanes/IPA/DEA mobile phase at room temperature and using a detection wavelength of 275 nm. Two enantiomers were isolated, 1(S) and 1(R), which correspond to the first and second eluting peaks from the column, respectively.

1.24 g of the first eluted enantiomer, atropisomer 1(S), was isolated and was analyzed under the analytical method described above (0.96 mg in 0.8 mL IPA). The HPLC trace, shown in FIG. 3B, has a major peak at 8.7 min and indicates 99.0% e.e.

1.38 g of the second eluted enantiomer, atropisomer 1(R), was isolated and was analyzed under the same analytical method (1.72 mg in 1 mL IPA) described above. The HPLC trace, shown in FIG. 3C, has a major peak at 13.0 min and indicates 98.8% e.e.

For purposes of discussion, resolved atropisomers of compound 1 that were isolated by normal phase chromatographic separation and eluted at time 8.7 min and 13.0 min as described in this example, will be referred to as atropisomers 1(S) and 1(R), respectively.

The absolute configuration of each isolated compound has been elucidated from x-ray crystallographic data. The first peak to elute has been assigned the S configuration, shown as compound 1(S), and the second peak to elute has been assigned the R configuration, shown as compound 1(R).

EXAMPLE 4

In Vitro Activity of 1, 1(S) and 1(R)

This example demonstrates the in vitro activity of 1, 1(S) and 1(R) against p110alpha, p110beta, p110 gamma and p110delta isoforms.

The in vitro activity of 1 and atropisomers, 1(S) and 1(R), have similar profiles in various isoforms of p110 inhibition as shown in FIGS. 5A and 5B. All three compounds exhibit selective p110δ inhibition in either biochemical (FIG. 5A) or cell-based assays (FIG. 5B). Although their in vitro potency appears to be similar, there are surprising in vivo differences observed between 1(S) and 1(R) as discovered in pharmacokinetic studies, mainly relating to the increased exposure of 1(S) and decreased exposure of 1(R) in the subject.

EXAMPLE 5

Blood Plasma Concentration of 1(S) and 1(R) in Rats, Dogs and Humans

This example follows the concentration of compound 1(S) and 1(R) in the blood plasma or rat, dog and human subjects over time.

In order to perform the pharmacokinetic studies, compound 1 was radiolabeled using $^{14}C$ at the ortho-methyl group of the phenyl at position 3 of the quinazolinone ring. Radiolabeled 1:

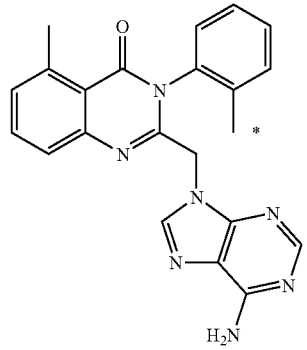

*denotes $^{14}C$ label

The tagged racemic mixture or separated atropisomers were administered in rats, dogs, and human subjects through oral and i.v. routes. The compounds were dissolved in PEG 100 such that any difference in dissolution rates would not play a role in the pharmacokinetic profile of the compounds. Modest solubility differences between compounds 1(S) and 1(R) were observed in a variety of aqueous solutions as summarized in FIG. 4. After administration of the compound, blood plasma of the subjects were sampled over time and evaluated by analytical HPLC methods developed to identify and measure concentrations of compound 1(S) or 1(R) present in the sample. It was observed that the most abundant isomer measured in the plasma is compound 1(S), which accounts for 70-80% of exposure to the subject.

FIG. 6 shows the blood plasma concentration of 1(S) and 1(R) over 24 hours after a single 50 mg/kg dose of racemic compound 1 was orally administered to female rats. 4 hours after dosing, the concentration of 1(S) steadily increases in the blood and 8 hours after dosing the average concentration of 1(R) is approximately one-fourth the concentration of 1(S). This demonstrates an in vivo difference in exposure between 1(S) and 1(R) when orally administered to rats, wherein the subject has increased exposure to 1(S) than 1(R).

FIG. 7 shows the blood plasma concentration of 1(S) and 1(R) over 24 hours after a single 50 mg/kg dose of racemic 1 was orally administered to female dogs. In approximately 1 hour after dosing the maximum concentration of compounds 1(S) and 1(R) is reached. At that point, the concentration of 1(R) is less than half the concentration of compound 1(S). This demonstrates an in vivo difference in exposure between compounds 1(S) and 1(R) when orally administered to dogs, wherein the subject has increased exposure to compound 1(S) than 1(R). These large differences in pharmacokinetic behavior were not predictable.

FIG. 8 shows the blood plasma concentration of compounds 1(S) and 1(R) over 72 hours after a single 100 mg dose of racemic compound 1 was orally administered to human subjects. Within 2 hours, the maximum concentration of compounds 1(S) and 1(R) is reached. At the maximum concentration point, the concentration of compound 1(R) is less than half the concentration of compound 1(S), which accounts for approximately 70% of the exposure in the animal. Although the concentrations of both compounds steadily decrease thereafter, at 72 hours post-dosing, the concentration of compound 1(S) is well over 10 times the concentration of compound 1(R). This demonstrates a surprising in vivo difference in exposure between compound 1(S) and 1(R) when orally administered to humans, wherein the subject has increased exposure to compound 1(S) relative to compound 1(R). Furthermore, it appears that the half-life of compound 1(S) is past the 72 hour time point. The half-life of compound 1(S) of several days in humans is greater than the half-life in dogs. By comparison, the half-life of 1(R) is around 9 hours. The long half-life of compound 1(S) in humans allows for a lower dosage of administration. Reduced administrative dosages may also reduce, if any, undesired side-effects of the compound in the subject and provides an advantage over administration of the racemic mixture, or over compound 1(R).

EXAMPLE 6

Oral Versus i.v. Administration of 1(S) and 1(R) in Rats

This example compares oral versus intravenous administration of compounds 1(S) and 1(R) in rats.

A single dose of 1(S) or 1(R) (1.5 mg/kg) was administered either via a single bolus i.v. dose (FIG. 9A) or an oral dose (FIG. 9B) to female rat subjects. The blood plasma concentration of either 1(S) or 1(R) was measured at different time points over a period of 24 hours after administration.

FIG. 9 shows the blood plasma concentration of 1(S) and 1(R) over a period of 24 hours after a single dose of 1(S) or 1(R) (1.5 mg/kg) administered either 1(S) a single bolus i.v. dose (FIG. 9A) or an oral dose (FIG. 9B) to female rat subjects. In the intravenously administered study at the 4 hour time point, the exposure level of 1(R) is approximately one-fifth the concentration of 1(S). At 24 hours, the concentration of both compounds is very low and within experimental error. The concentration of 1(S) in blood plasma of rats that were orally administered the compounds was shown to greatly exceed the concentration of 1(R) at the 12 hour time point. This demonstrates an in vivo difference in exposure between 1(S) and 1(R) when either intravenously or orally administered to rats, wherein the subject has increased exposure to 1(S) relative to 1(R).

EXAMPLE 7

Pharmacokinetic Parameters of 1(S) and 1(R) in Rats following Single i.v. Dose

This example compares the pharmacokinetic parameters of compounds 1(S) and 1(R) in female Sprague Dawley (SD) rats following a single i.v. dose. SD rats were administered a single bolus intravenous dose of 1(S) (1.5 mg/kg), 1(R) (1.5 mg/kg) or 1 (3 mg/kg) and the compound present in the subject was measured over time. Based on this data, pharmacokinetic parameters were calculated as summarized in Table 3.

Most notable is the half life of compound 1(R), which is about 2.8 times greater in rats than the half life of either atropisomer 1(S) or the racemic mixture 1. Compound 1(R) has a volume of the terminal phase (Vz) value of 14,833 mL/kg, which is about 2.6 times greater than the Vz for either 1(S) or the racemic mixture.

TABLE 3

| Parameter | Compound 1(S) (1.5 mg/kg) | Compound 1(R) (1.5 mg/kg) | Compound 1 (3 mg/kg) |
|---|---|---|---|
| T½ (hr) | 2.5 ± 1.6 | 7.0 ± 1.1 | 2.5 ± 0.7 |
| CL (ml/hr/kg) | 1838 ± 503 | 1476 ± 85 | 1560 ± 180 |
| Vz (ml/kg) | 5773 ± 2740 | 14883 ± 2034 | 5397 ± 1568 |
| AUCall (ng/ml × hr) | 865 ± 212 | 1010 ± 55 | 1971 ± 243 |

EXAMPLE 8

Pharmacokinetic Parameters of 1(S) and 1(R) in Humans following Single Oral Dose This example compares pharmacokinetic parameters of compounds 1(S) and 1(R) in humans following a single oral dose of a racemic mixture. Two dosing studies were performed. A single, 100 mg oral dose of racemic mixture 1 was orally administered to human subjects, and blood plasma concentration levels of each of the atropisomer compounds was measured over a period of 72 hours. In another study, a single, 10 mg oral dose of racemic mixture 1 was orally administered to human subjects, and blood plasma concentration levels of each of the atropisomer compounds was measured over a period of 120 hours.

FIGS. 10A and 10B show graphs of the blood plasma concentration of 1(S) and 1(R) plotted against a period of 72 hours after administration of a single, oral dose of 100 mg of the individual atropisomers. The maximum concentration of 1(S) is over 2 times as great as the maximum concentration for 1(R). Although the concentration of the compounds in the blood plasma decreases over the 72 hour period, the difference in concentration of the two compounds is maintained, if not further broadened. This difference in compound concentration in the blood appears to broaden because compound 1(S) decreases more gradually over time whereas compound 1(R) appears to be removed from the blood relatively more quickly.

Figure 10C:
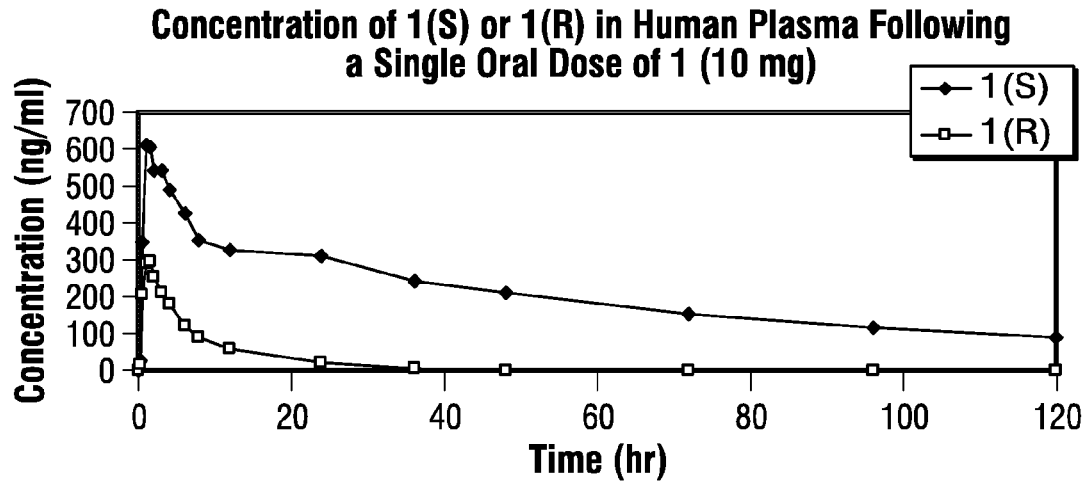
Figure 10D:
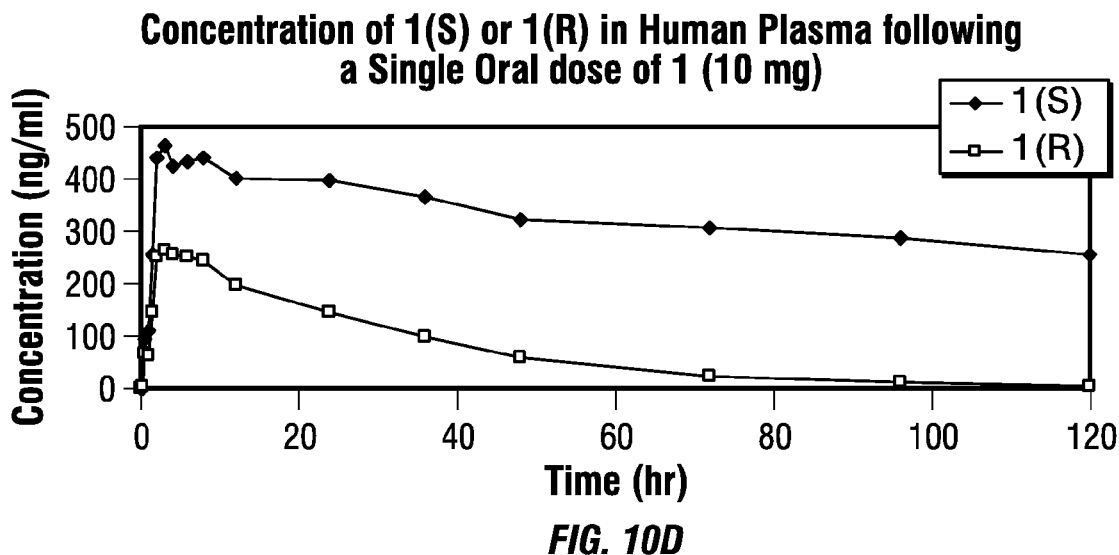

At a dose of 10 mg, the maximum blood plasma concentration of compound 1(S) is still about double the maximum concentration of compound 1(R), see FIGS. 10C and 10D.

EXAMPLE 9

Radiolabeled 1(S) and 1(R) in Human Plasma

This example compares the concentration of radiolabeled 1(S) and 1(R) in human plasma in the middle of a daily dosing regimen.

Human subjects were dosed with 25 mg of a racemic mixture of 1(S) and 1(R) each day for 7 days. On day 4, the dose was 'spiked' with 40 nCi of labeled 1(S) or labeled 1(R). (Total dosage was still 25 mg of the racemic mixture, since the amount of labeled material was less than 0.1 mg so it did not materially affect the dosage.) From this point, the blood plasma of the subject was sampled over time and the radiolabeled compound was detected and quantified.

FIG. 11 depicts the concentration of $^{14}$C radiolabeled compound 1(S) and 1(R) in total blood plasma. FIG. 11 shows the pharmacokinetic profile for total radiolabeled material starting when the spiked material was administered on day 4, and continuing for several days thereafter.

Both compounds in this test quickly reached their maximum concentration values and began a steady decline of concentrations in the bloodstream. After day 1, the amount of 1(R), about 500 neq/mL, drops to about one-fourth the concentration of 1(S), which is about 2000 neq/mL. The more rapid decline of 1(R) in the blood compared to 1(S) is further evident at 50 hours from dosing, wherein the blood plasma concentration of compound 1(S) is between 500 to 1000 neq/mL compared to concentration of 1(R) which is about 10-50 neq/mL. The concentration of 1(R) decreases more rapidly than the concentration of 1(S) as shown by the sharper slope of the 1(R) curve compared to the more gradual and gentle slope of 1(S) in FIG. 11.

Table 4 summarizes the half-life, $C_{max}$ and AUC values in human subjects for compounds 1(S) and 1(R) based on the data in FIG. 11. At nearly 64 hours, compound 1(S) has a half-life 6 times as long as the half-life of 1(R), which has a half-life of under 11 hours. The $C_{max}$ value for 1(S) is twice as long as that of 1(R), and the AUC value for 1(S) is over 4 times as that of 1(R). These results demonstrate that compound 1(S) has an unexpected and very different pharmacokinetic profile compared to compound 1(R) in human subjects after oral dosing. Compound 1(S) has a significantly longer half-life, as well as increased $C_{max}$ and AUC values; thus compound 1(S) produces greater exposure in humans compared to 1(R). Compound 1(S) therefore offers unexpected advantages over either 1(S) or a racemic mixture, and treatment of a human with 1(S) can provide a higher, more stable plasma level of active drug than treatment with 1(R) or the racemate, and simultaneously reduces exposure of the subject to other materials or metabolites of 1(R).

TABLE 4

|  | T½ [h] | Cmax [neq/mL] | AUClast [neq*h/mL] |
| --- | --- | --- | --- |
| Compound 1 | 69.9 ± 26.6 | 2780 ± 1163 | 51,032 ± 22,383 |
| Compound 1(S) | 63.9 | 3930 | 90511 |
| Compound 1(R) | 10.6 | 1946 | 21676 |

EXAMPLE 10

Metabolic Products formed from 1(S) and 1(R) in Rats

This example compares the formation of metabolic products in rats after administration of compounds 1(S) and 1(R).

A single 50 mg/kg oral dose of either atropisomer 1(S) or 1(R) was administered to rat subjects. The rat urine was subsequently sampled and analyzed using LC-MS instrumentation.

FIGS. 12A and 12B show LC-MS results of the metabolites found in the urine. Rats which were exposed to 1(S) produced mainly one compound represented by a peak at 13.4 minutes and a second compound represented by a much smaller peak at 14.5 minutes, FIG. 12A. On the other hand, the analytical traces of urine from rats which were administered compound 1(R) are characterized by three main peaks at 13.5, 14.4, and 15.6 minutes, and a small peak at minute 12.1, FIG. 12B. This demonstrates that compound 1(R) is metabolized in vivo to produce more metabolic products compared to compound 1(S) and suggests that the two atropisomers are not metabolized by the body in exactly the same way.

EXAMPLE 11

Metabolic Products Formed from 1(S) and 1(R) in Human Subjects

This example compares the formation of metabolic products in human subjects after administration of compounds 1(S) and 1(R).

For these tests, either radiolabeled 1(S) or radiolabeled 1(R) was administered orally to a human subject. Samples of plasma from the subject were tested 1 hour and 72 hours after administration, and were analyzed for their radiolabeled content. The analysis used HPLC conditions that were known to separate 1(S) (eluting at about 21-22 minutes) from 1(R), so any interconversion between these species could be observed. It also resolves these two materials from the major metabolites formed from them in vivo.

FIGS. 13A-13D further illustrate the unexpected stability of 1(S) in vivo relative to 1(R). The UV trace in each spectrum is provided as a retention time standard to confirm the identity of the peaks, but the important data to observe is the C-14 radiolabel signal, which is represented by small squares at the retention time for 1(S), 1(R), and the known metabolites of these compounds. In FIG. 13A, there are two radiolabeled peaks observed, compound 1(S) (large peak at about 22 minutes) and a metabolite (small peak at about 14 minutes). In FIG. 13B, there are two dominant C-14 data points, 1(R) at 22 minutes, and a metabolite at 14 minutes. In this case, the metabolite level is nearly as large as the level of compound 1(R), even just one hour after administration of 1(R). Thus, compound 1(S) results in less metabolite formation than compound 1(R) in human plasma, and remains largely unmodified after 1 hr. At 72 hours, the amount of metabolites formed from 1(S) is still less than the amount of the parent compound 1(S), FIG. 13C; so most of the detected $^{14}C$ detected label corresponds to the active drug. It appears that a small amount of 1(R) is present at this point in time, suggesting that some interconversion of 1(S) to 1(R) may occur in vivo. For 1(R) at 72 hours, primarily the metabolites are detected and very little of 1(R) is seen; indeed, it appears there may be more 1(S) than 1(R) present, again suggesting a small amount of interconversion may occur: see FIG. 13D.

Therefore, the abundance of metabolite after dosing with radiolabeled 1(R) suggests that compound 1(R) is metabolized by the human body relatively quickly. The low to nonexistent levels of metabolite in the plasma samples containing compound 1(S) suggests lower levels of metabolism, and the higher concentration of 1(S) 72 hours after administration shows this isomer provides longer exposure from a single dose.

EXAMPLE 12

Evidence for Superiority of a Single Atropisomer over the Racemic Mixture

This example compares the metabolic differences of the single 1(S) atropisomer over the racemic mixture. The atropisomer 1(S) was shown to have a greater exposure than the racemic mixture, 1, in humans, which can be attributed to the greater metabolism of the atropisomer 1(R) and the greater metabolic stability of atropisomer 1(5).

Human pharmacokinetic was obtained after both the racemic mixture and 1(S) were administered at 10 mg once daily.

The $C_{max}$ values for 1(S) were 30% greater than those of racemic mixture, while the $AUC_{0-24}$ values were increased 2.4-fold on Day 1 and 40% on Day 7. Since the dose is low and well absorbed, as evidenced by the determination of 100% bioavailability, it is likely that the 1(R) metabolism is greater. The greater extent and complexity of 1(R) metabolism was supported by studies on human and rat in vivo metabolism as well as in vitro studies of human liver microsomes and protein binding.

Urine was collected from humans dosed the racemic mixture and evaluated for possible metabolites using LC/MS/MS. Using authentic racemic standards in an achiral method, 5 metabolites were confirmed. Of the five confirmed metabolites, four are composed of racemic mixtures of atropisomers. Therefore, a total of 9 metabolites were observed in human urine. The figure below indicates approximate relative abundance using the thickness of the arrow.

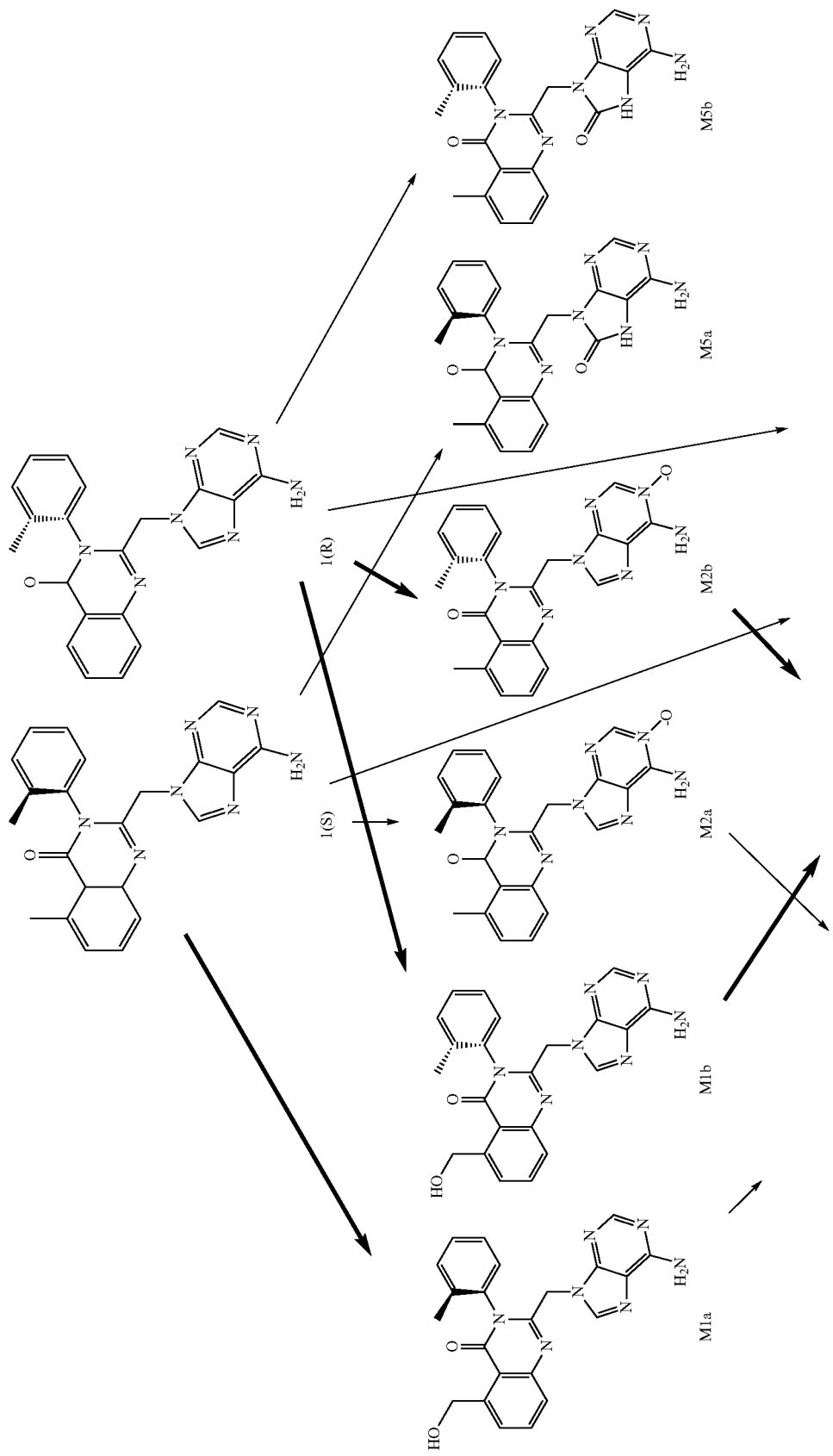

-continued
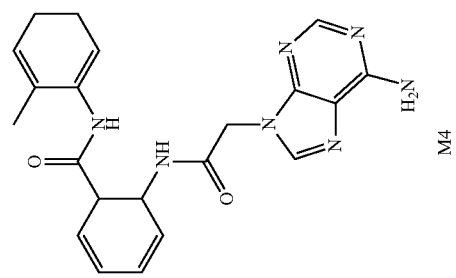
M4
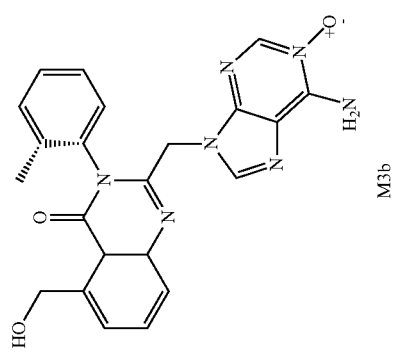
M3b
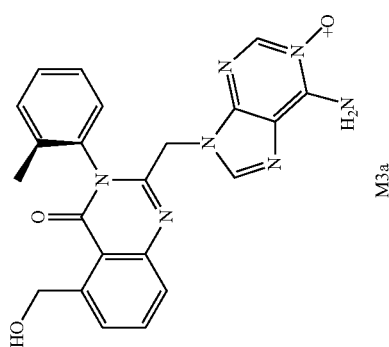
M3a
† indicates text missing or illegible when filed In addition, plasma from human subjects dosed with the racemic mixture was confirmed to contain 2 metabolites and the 2 atropisomers. One of the metabolites (M1b) was greater than 10% of the parent levels of the active test article. The figure below indicates approximate relative abundance using the thickness of the arrow.

metabolite, M1a was observed and it was at less than 10% of parent levels, presenting a lower risk and a simplified drug development path.

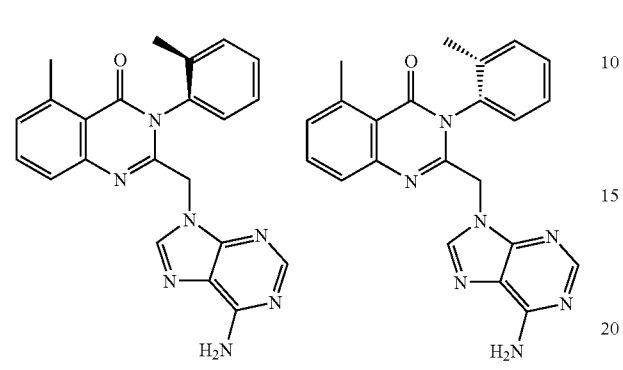

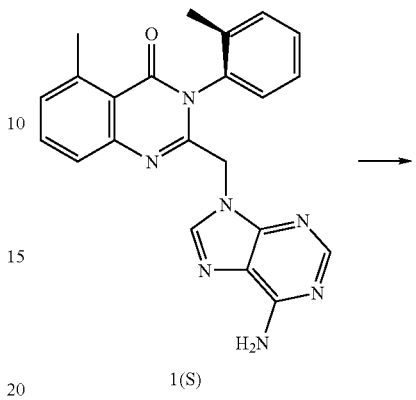

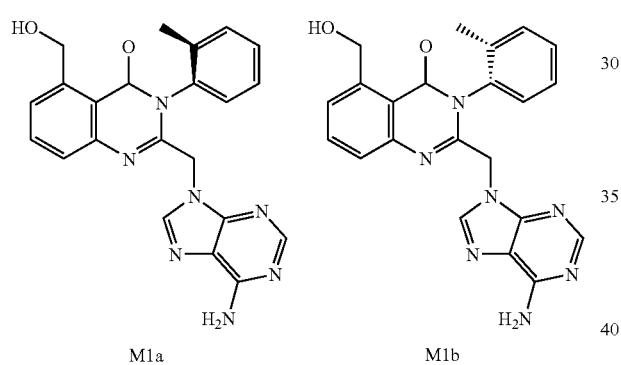

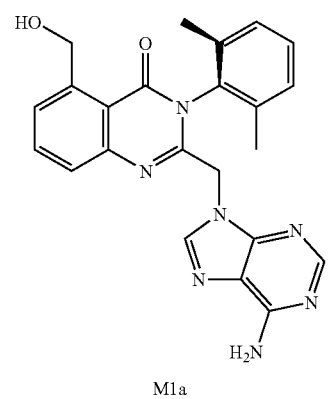

In contrast, because 1(S) is more metabolically stable, and it is a single entity, the plasma profile was simplified. In human plasma samples analyzed for metabolites, only one Based on the fact that conversion of the isomers has been shown to not isomerize the chiral center, the expected excreted metabolites of human subjects that were dosed with 1(S) are likely to be less complicated. It is anticipated to contain 5 total metabolites as opposed to 9 seen with the racemic mixture. The figure below indicates approximate relative abundance using the thickness of the arrow.

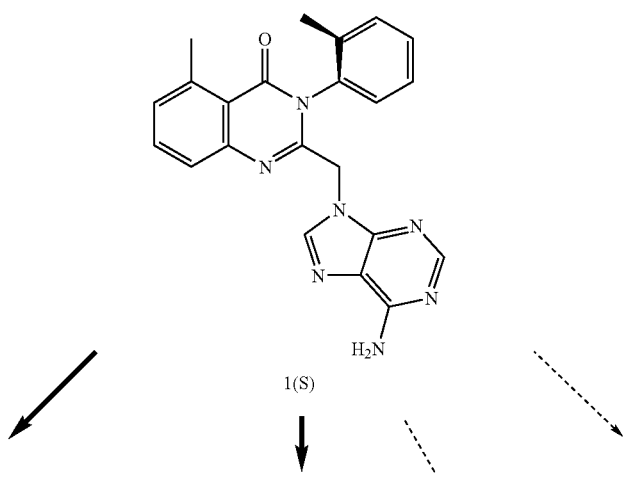

-continued

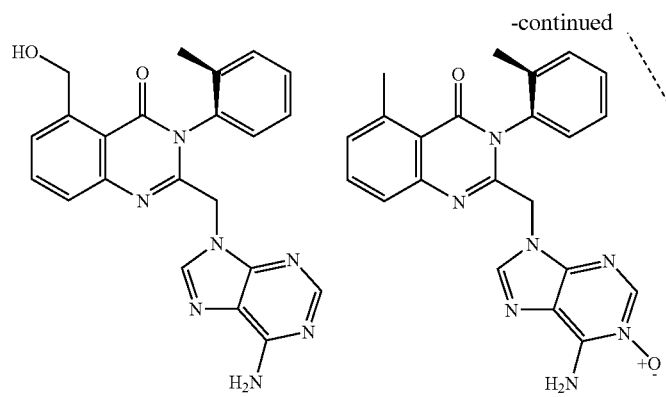

M1a    M2a

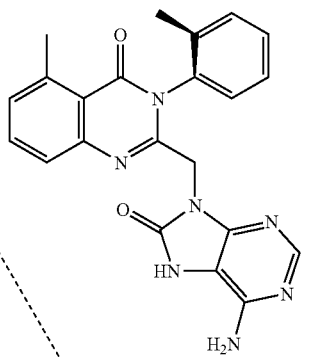

M5a

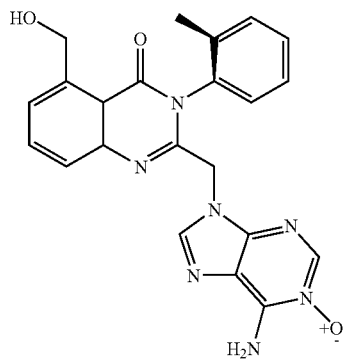

M3a

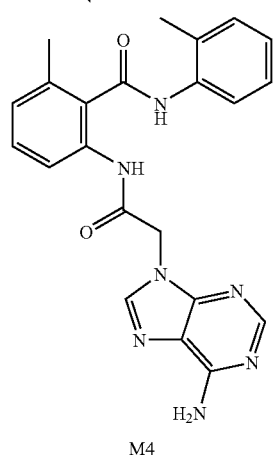

M4

EXAMPLE 13

Figure 14:
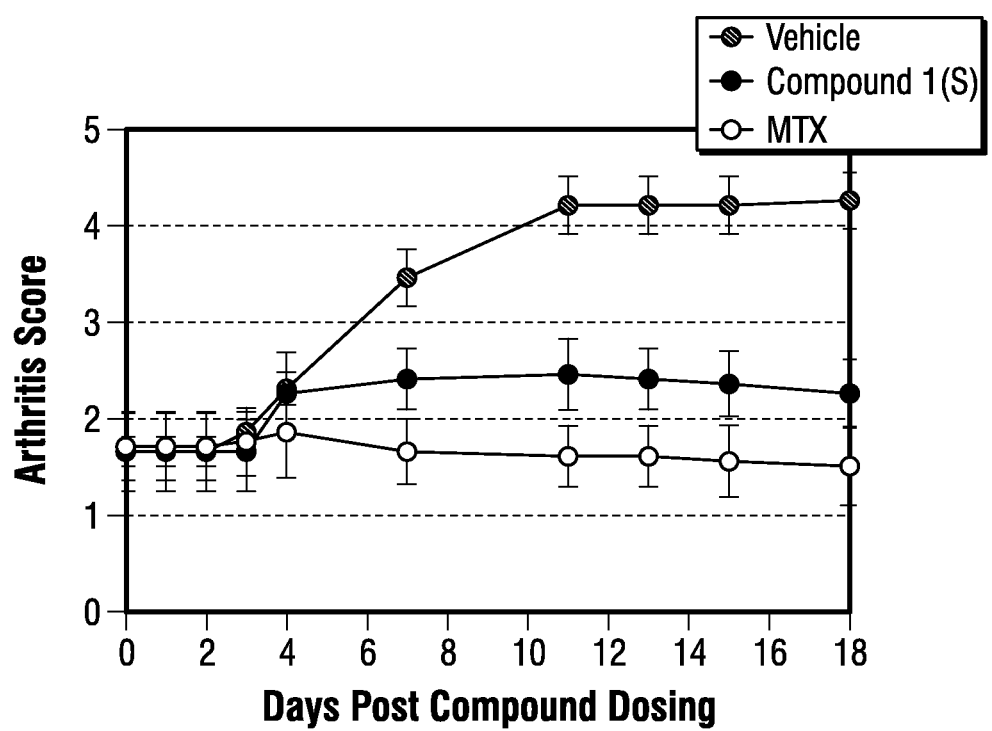
FIG. 14 shows a plot of arthritis scores plotted against days post compound dosing for 1(S) in collagen induced arthritis rat models.
Figure 15:
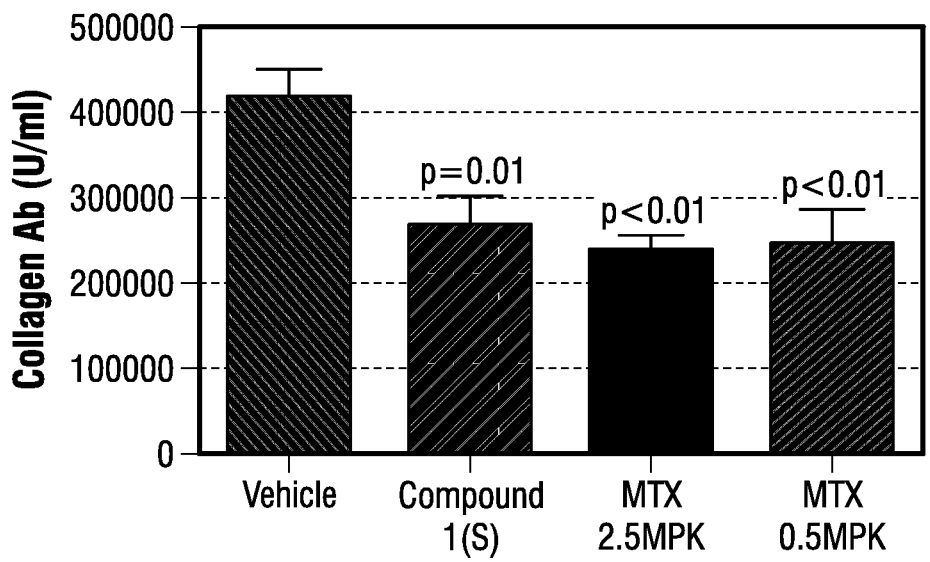
FIG. 15 shows a graph of anti-collagen antibody levels in rat after dosing the subjects with vehicle, 1(S) or methotrexate.
Figure 16:
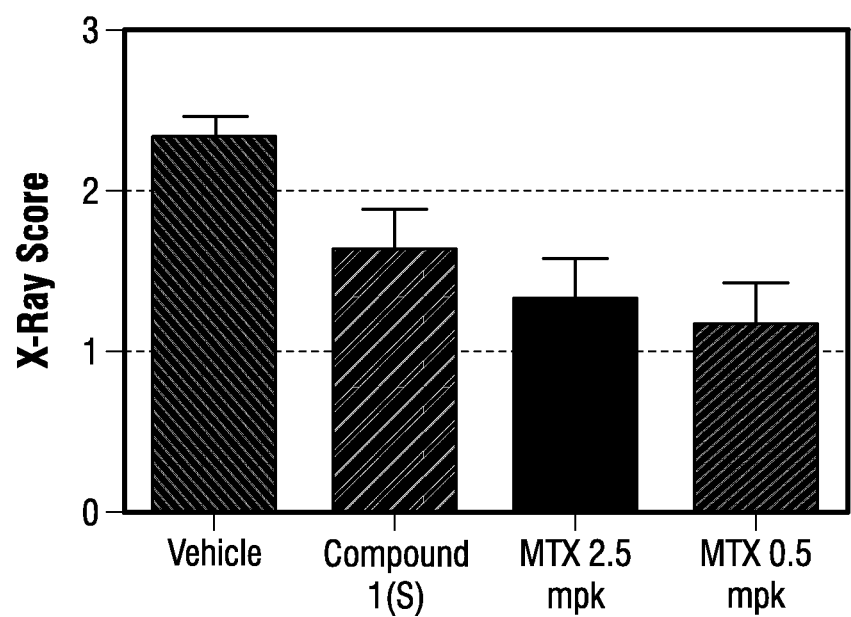
FIG. 16 shows a graph of X-ray score from a radiographic assessment of rats treated with either vehicle, 1(S), or methotrexate.
Figure 17B:
FIGS. 17A-D shows images from histopathology data from subjects treated with vehicle, 1(S), or methotrexate.
Figure 17D:
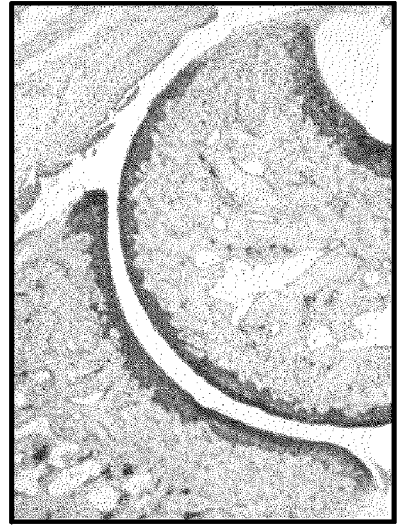
Figure 17A:
Figure 17C:

Evidence For Anti-Arthritic Activity Of Isomer 1(S) In Collagen Induced Arthritis Rats The effect of compound 1(S) in collagen induced arthritis (CIA) rats was measured and compared to subjects exposed to vehicle or methotrexate. FIG. 14 shows a graph that compares the effect of vehicle, compound 1(S) or MTX on the severity of CIA in vivo. The graph plots the arthritis score as a function of the days post compound dosing and shows that compound 1(S) has activity in reducing the severity of arthritis in rat models. FIG. 14 compares the effect of vehicle, compound 1(S), and varying levels of methotrexate on anti-collagen antibody levels in CIA rat models. In FIG. 15 we see additional evidence of anti-arthritic activity in vivo wherein rats that were administered compound 1(S) showed signs of reduction of collagen antibody levels in comparison to rats that were administered only vehicle. Radiographic assessments on CIA rat subject treated with the various compounds also show reduction in the X-ray score of subjects treated with compound 1(S), FIG. 16, compared to subjects treated with vehicle only. FIGS. 17A-D show images of tissue samples taken from CIA rats treated with vehicle, compound 1(S), or MTX (0.5 mg/kg and 2.5 mg/kg). The dark areas of the images is reduced in samples from subjects treated with compound 1(S) compared to the vehicle, and is similar to the images taken from subjects treated with MTX. These studies in CIA rat models of arthritis show that compound 1(S) has anti-inflammatory activity in vivo and can be used in treating inflammatory conditions such as arthritis.

The invention claimed is:

1. An optically active compound comprising an atropisomer of formula 1(S)

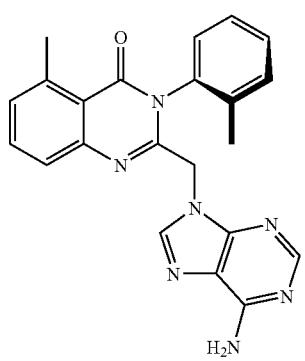

1(S)

or a pharmaceutically acceptable salt thereof;

wherein the atropisomer of formula 1(S) or a pharmaceutically acceptable salt thereof, is present in excess of its corresponding enantiomer or a pharmaceutically acceptable salt thereof.

2. The optically active compound according to claim 1, substantially free of the corresponding enantiomer or a pharmaceutically acceptable salt thereof.

3. An optically active compound comprising an atropisomer of formula 1(R)

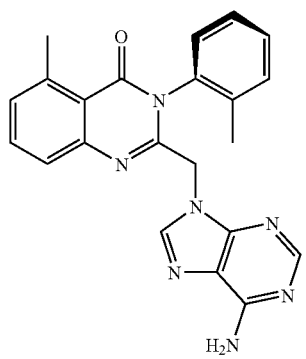

1(R)

or a pharmaceutically acceptable salt thereof;
wherein the atropisomer of formula 1(R) or a pharmaceutically acceptable salt thereof, is present in excess of its corresponding enantiomer or a pharmaceutically acceptable salt thereof.

4. The optically active compound according to claim 3, substantially free of the corresponding enantiomer or a pharmaceutically acceptable salt thereof.

5. A pharmaceutical composition comprising an optically active compound of formula 1(S),

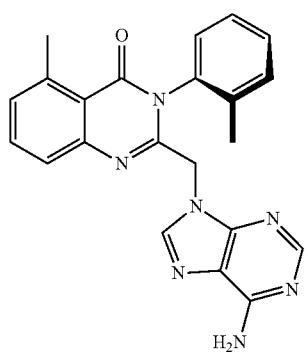

1(S)

or a pharmaceutically acceptable salt thereof, and
at least one pharmaceutically acceptable carrier.

6. A pharmaceutical composition comprising an optically active compound of formula 1(R)

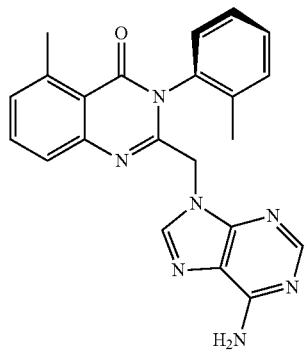

1(R)

or a pharmaceutically acceptable salt thereof, and
at least one pharmaceutically acceptable carrier.

7. A method of treating rheumatoid arthritis (RA) in a mammal, which comprises administering to a mammal in need thereof a therapeutically effective amount of the optically active compound according to claim 1.

8. A method of treating rheumatoid arthritis (RA) in a human,
which comprises administering to a human in need thereof a therapeutically effective amount of an optically active atropisomer having the formula

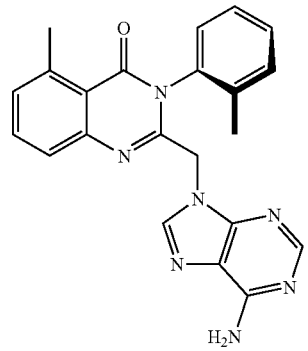

1(S)

or a pharmaceutically acceptable salt thereof.

9. An optically active compound obtained by separation of a racemic mixture of formula 1

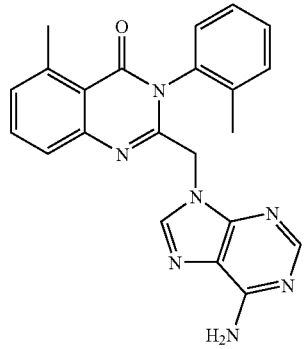

(1)

or a pharmaceutically acceptable salt thereof;

wherein the optically active compound comprises an atropisomer of formula 1 or a pharmaceutically acceptable salt thereof, in excess of its enantiomer or pharmaceutically acceptable salt thereof, and wherein the optically active compound is characterized by a shorter retention time on a normal phase chiral column compared to its enantiomer or a pharmaceutically acceptable salt thereof.

10. The compound according to claim 9, consisting of the compound of formula 1(S) or a pharmaceutically acceptable salt thereof, substantially free of the compound of formula 1(R), or a pharmaceutically acceptable salt thereof, wherein 1(S) and 1(R) are depicted below:

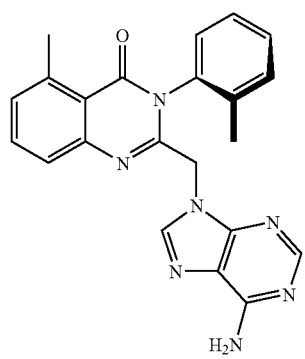

1(S)

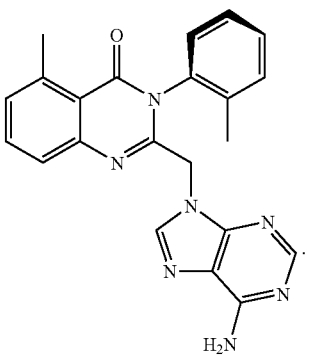

1(R)

11. The compound according to claim 9, consisting of the compound of formula 1(R) or a pharmaceutically acceptable salt thereof, substantially free of the compound of formula 1(S), or a pharmaceutically acceptable salt thereof, wherein 1(S) and 1(R) are depicted below:

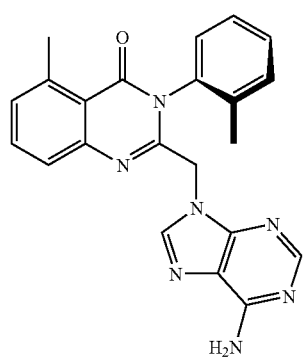

1(S)

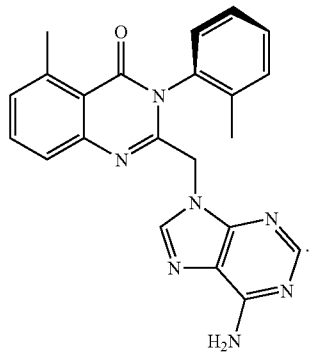

1(R)

12. An optically active compound obtained by separation of a racemic mixture of formula 1

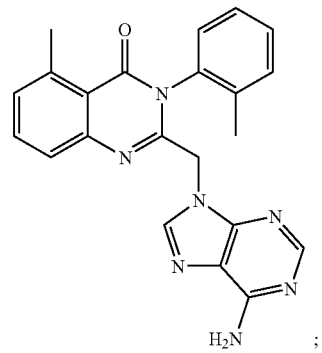

(1)

or a pharmaceutically acceptable salt thereof;

wherein the optically active compound comprises an atropisomer of formula 1 or a pharmaceutically acceptable salt thereof, in excess of its enantiomer or pharmaceutically acceptable salt thereof, and wherein the optically active compound is characterized by a longer retention time on a normal phase chiral column compared to its enantiomer or a pharmaceutically acceptable salt thereof.

13. The compound according to claim 12, consisting of the compound of formula 1(S) or pharmaceutically acceptable salt thereof, substantially free of the compound of formula 1(R), or a pharmaceutically acceptable salt thereof, wherein 1(S) and 1(R) are depicted below:
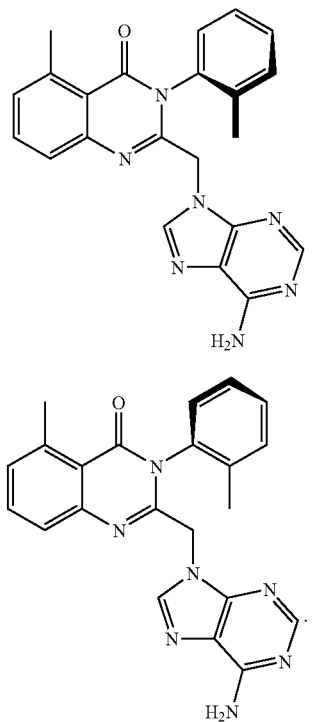
14. The compound according to claim 12, consisting of the compound of formula 1(R) or a pharmaceutically acceptable salt thereof, substantially free of the compound of formula 1(S) or a pharmaceutically acceptable salt thereof,
wherein 1(S) and 1(R) are depicted below:
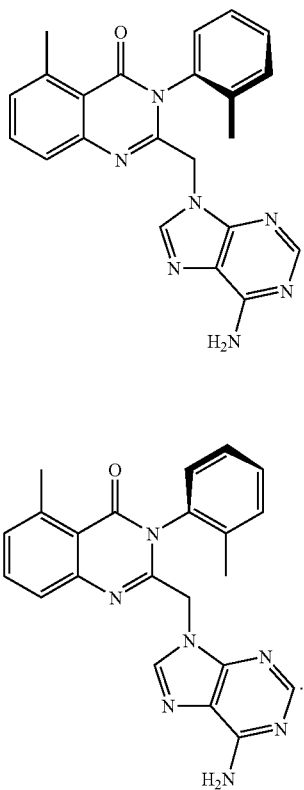
* * * * *